US008257928B2

(12) United States Patent
Weaver et al.

(10) Patent No.: US 8,257,928 B2
(45) Date of Patent: Sep. 4, 2012

(54) METHODS FOR PREDICTING AND TREATING TUMORS RESISTANT TO DRUG, IMMUNOTHERAPY AND RADIATION

(75) Inventors: Valerie M. Weaver, San Francisco, CA (US); Kun-Chih Kelvin Tsai, Taipei (TW)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/227,279

(22) Filed: Sep. 7, 2011

(65) Prior Publication Data
US 2012/0071341 A1 Mar. 22, 2012

Related U.S. Application Data

(63) Continuation of application No. 12/464,040, filed on May 11, 2009, now Pat. No. 8,093,000.

(60) Provisional application No. 61/052,139, filed on May 9, 2008.

(51) Int. Cl.
*C12Q 1/68* (2006.01)
(52) U.S. Cl. ........................................................ 435/6.1
(58) Field of Classification Search ........................ None
See application file for complete search history.

(56) References Cited

U.S. PATENT DOCUMENTS

| | | | |
|---|---|---|---|
| 7,171,311 B2 | 1/2007 | Dai et al. | |
| 2005/0176669 A1* | 8/2005 | Al-Murrani | 514/44 |
| 2005/0266420 A1 | 12/2005 | Pusztai et al. | |
| 2007/0105133 A1 | 5/2007 | Clarke et al. | |
| 2007/0172844 A1 | 7/2007 | Lancaster et al. | |

OTHER PUBLICATIONS

Bailey et al., "The Nuclear Receptor Corepressor N-CoR Regulates Differentitation: N-CoR Directly Interacts with MyoD," *Mol. Endocrinol.*, vol. 13, p. 1155-1168 (1999).
Croix et al., "Impact of the cyclin-dependent kinase inhibitor p27$^{Kip1}$ on resistance of tumor cells to anticancer agents," *Nature Med.*, vol. 2, No. 11, p. 1204-1210 (1996).
Desoize et al., "Multicellular resistance: a paradigm for clinical resistance?" *Crit. Ref. Oncol. Hematol.*, vol. 36, p. 193-207 (2000).
Esteller et al., "Inactivation of the DNA-Repair Gene MGMT and the Clinical Response of Gliomas to Alkylating Agents," *N. Engl. Journ. Med.*, vol. 343, p. 1350-1354 (2000).
Feinberg et al., "The epigenetic progenitor origin of human cancer," *Nat. Rev. Genet.*, vol. 7, p. 21-33 (2005).
Gifford et al., "The Acquisition of hMLH1 Methaylation in Plasma DNA after Chemotherapy Predicts Poor Survival of Ovarian Cancer Patients," *Clinical Cancer Res.*, vol. 10, p. 4420-4426 (2004).
Glasspool et al., "Epigenetics as a mechanism driving polygenic clinical drug resistance," *Br. J. Cancer*, vol. 94, p. 1087-1092 (2006).
Graham et al., "Thoughts on tamoxifen resistant breast cancer. Are coregulators the answer or just a red herring?" *J. Steroid Biochem Mol. Biol.*, 74(5), p. 255-259 (2000).
Green et al., "Adhesion-dependent multicellular drug resistance," *Anticancer Drug Des.*, vol. 14, No. 2, p. 153-168 (1999).
Hermanson et al., "N-CoR controls differentiation of neural stem cells into astrocytes," *Nature*, vol. 419, p. 934-939 (2002).
Jepsen et al., "SMRT-mediated repression of an H3K27 demethylase in progression from neural stem cell to neuron," *Nature*, vol. 450, p. 415-420 (2007).
Khabele et al., "Drug-Induced Inactivation or Gene Silencing of Class I Histone Deacetylases Suppresses Ovarian Cancer Cell Growth," *Cancer Biology & Therapy*, 6(5), p. 795-801 (2007).
Kobayashi et al., "Acquired multicellular-mediated resistance to alkylating agents in cancer," *Proc. Natl. Acad. Sci.*, vol. 90, p. 3294-3298 (1993).
Modlich et al., "Predictors of primary breast cancers responsiveness to preoperative Epirubicin/Cyclophosphamide-based chemotherapy: translation of microarray data into clinically useful predictive signatures," *Journal of Translational Medicine BoMed*, vol. 3, No. 32, p. 1-18 (2005).
Pearson et al., "PML regulates p53 acetylation and premature senescence induced by oncogenic Ras," *Nature*, vol. 406, p. 207-210 (2001).
Privalsky, Martin L., "The Role of Corepressors in Transcriptional Regulation by Nuclear Hormone Receptors," *Annual Rev. Physiol.* vol. 66, p. 315-360 (2004).
Teicher et al., "Tumor resistance to alkylating agents conferred by mechanisms operative only in Vivo," *Science*, vol. 247, p. 1457-1461 (1990).
Teodorisis et al., "CpG Island Methylation of DNA Damage Response Genes in Advanced Ovarian Cancer," *Cancer Re.*, vol. 65, No. 19, p. 8961-8967 (2005).

* cited by examiner

*Primary Examiner* — Christopher M. Babic
(74) *Attorney, Agent, or Firm* — Morgan, Lewis & Bockius LLP; Annette S. Parent

(57) ABSTRACT

The present invention relates to methods for prognosis, diagnosis, and treatment of malignant tumors that were treatment resistant. The present invention provides methods of prognosis and diagnosis of multidrug resistant tumors through detection of the expression levels of nuclear co-repressor 2 ("N-CoR2"), histone deacetylases 3 ("HDAC3"), and their associated gene expression biomarkers. The present invention also provides methods of sensitizing tumors to anti-tumor therapeutics by disrupting HDAC3 activation, abrogating the N-CoR2-HDAC3 interaction, inhibiting the activity of either protein, or by downregulating the expression of either protein.

25 Claims, 24 Drawing Sheets
(17 of 24 Drawing Sheet(s) Filed in Color)

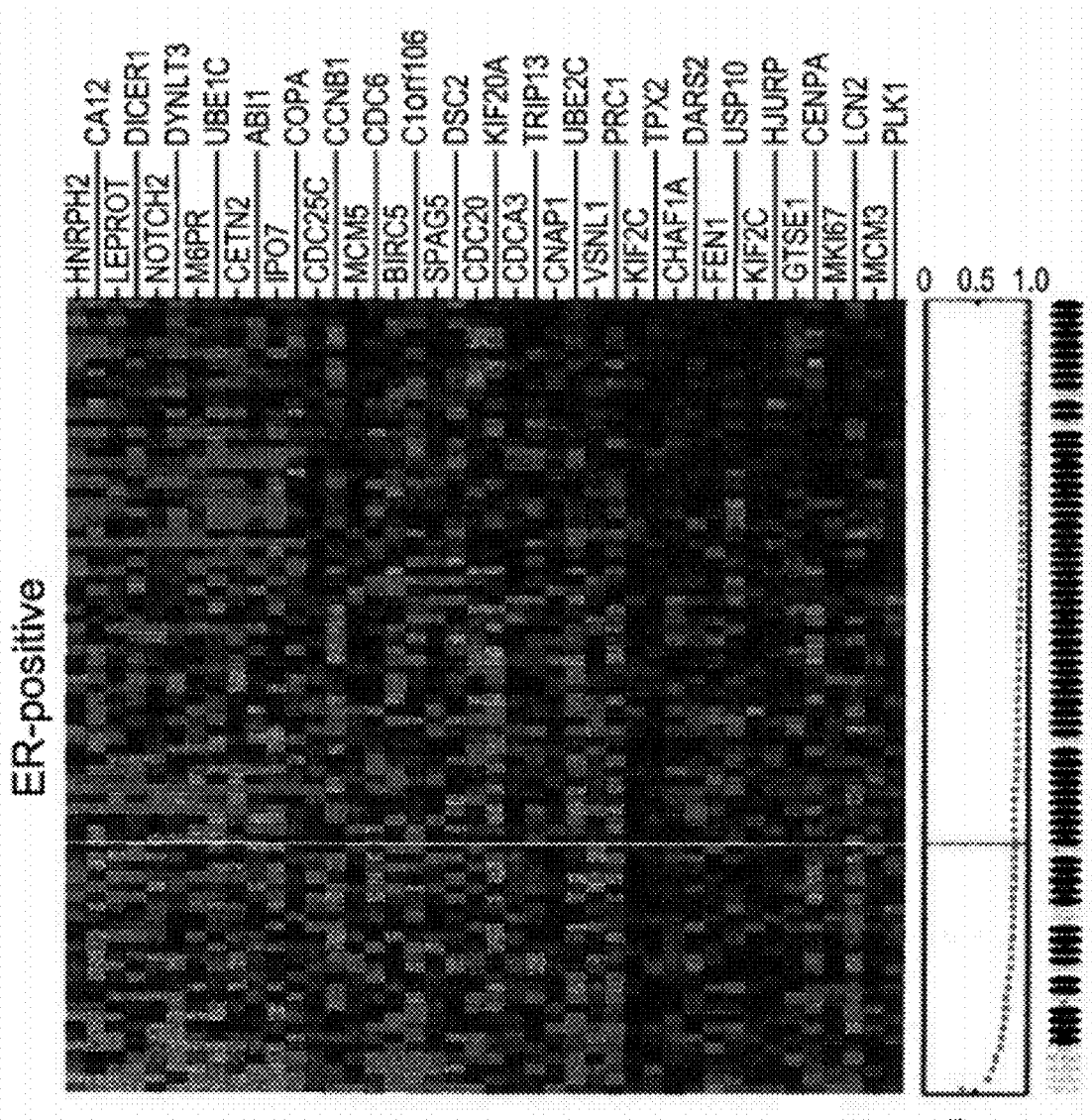
Fig. 9 (Sheet 1)

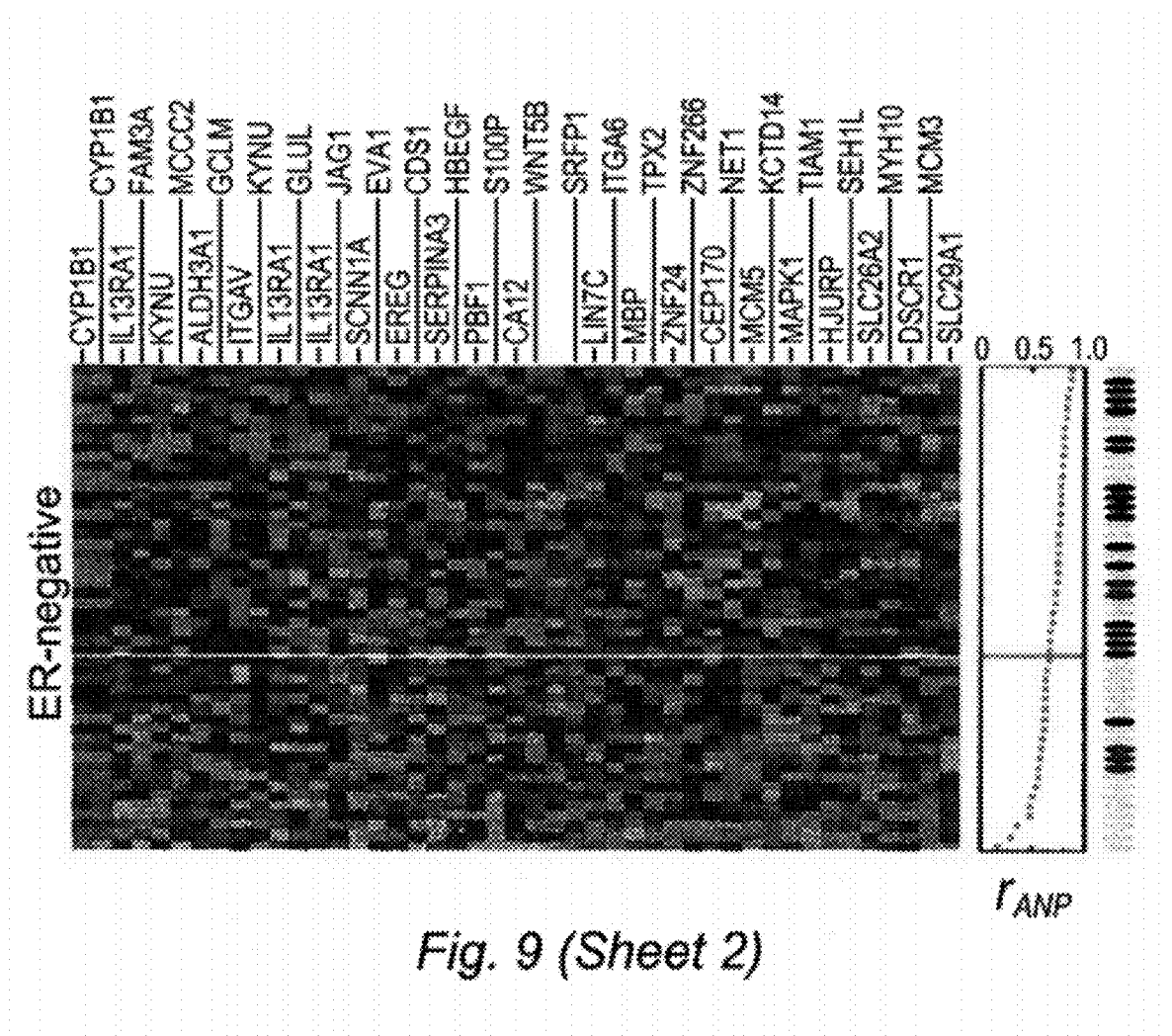
Fig. 9 (Sheet 2)

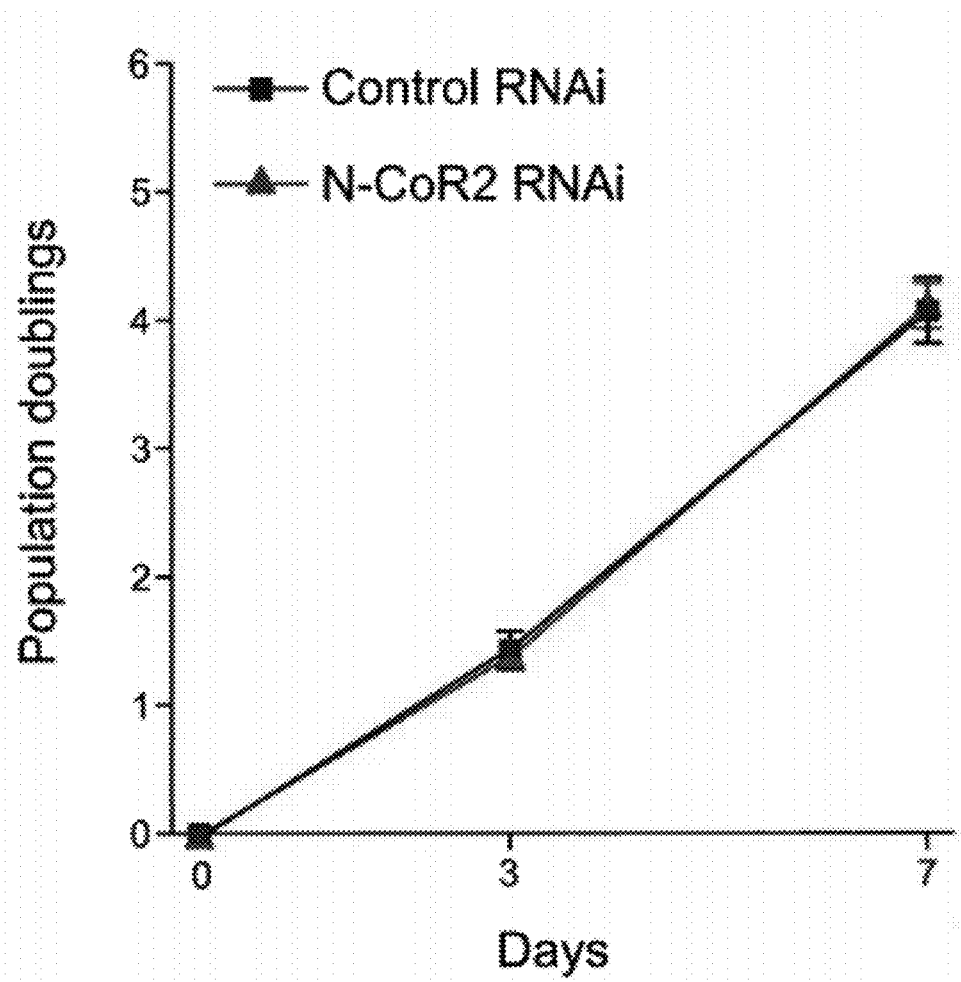
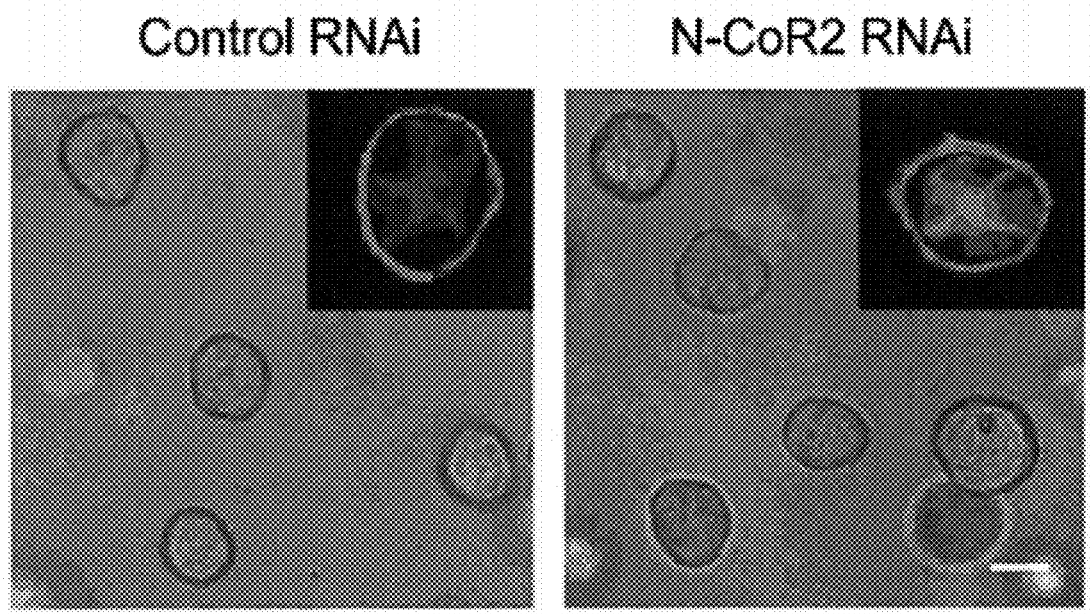
*Fig. 12*

METHODS FOR PREDICTING AND TREATING TUMORS RESISTANT TO DRUG, IMMUNOTHERAPY AND RADIATION

CROSS-REFERENCES TO RELATED APPLICATIONS

This application is a Continuation of U.S. patent application Ser. No. 12/464,040 (issued as U.S. Pat. No. 8,093,000) filed on May 11, 2009 which claims priority to U.S. Provisional Application No. 61/052,139 filed on May 9, 2008, both of which are incorporated herein by reference in their entireties.

STATEMENT AS TO RIGHTS TO INVENTIONS MADE UNDER FEDERALLY SPONSORED RESEARCH AND DEVELOPMENT

This invention was made in part with Governmental support under grant no. CA078731 awarded by the National Institute of Health. The Government has rights in this invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The development of intrinsic or acquired drug resistance by tumor cells significantly limits the efficacy of antineoplastic agents and is the major contributing factor to therapeutic failure of human malignancies. Drug resistance refers to progressive disease of the malignant tumors that occurs at doses associated with manageable toxicity of the drug. It is well known in the clinical practice that many malignant tumors are initially sensitive to chemotherapy, but the vast majority will eventually recur and develop broad resistance to conventional cytotoxic chemotherapeutic agents and radiotherapy (Nat. Rev. Cancer 3:502-516 (2003)).

Laboratory-based studies have identified a wide variety of genes and molecular pathways, such as MDR1 (P-glycoprotein) (Cancer Res. 53:747-754 (1993)) and p53 (Cell 74:957-967 (1993)), that can lead to increased resistance to treatments in malignant tumor cells. Nevertheless, significant discrepancies exist between drug resistance identified in experimental models and the multidrug resistance (MDR) phenotypes found in human malignant tumors (Br. J. Cancer 94:1087-1092 (2006)). For instance, acquisition of p53 mutations and gene amplification of MDR1 are rarely observed following chemotherapy in clinical human malignancies and so far there is little evidence demonstrating that single gene-mediated drug resistance individually correlated with treatment outcome of human malignancies (Nat. Rev. Cancer 3:502-516 (2003)).

The discrepancy between experimental and clinical drug resistance may partly stem from the distinct multicellular and spatial-dimensional contexts under which tumor drug resistance develops in vivo. Most of the current knowledge about the cellular responses to chemicals, toxins or radiation were gathered from studies using unicellular culture models, which lacked consideration of the heterotopic cell-cell interactions in the tumor-host interface (Nature 411:375-379 (2001)). Previously, it has been clearly shown that the drug resistance phenotype of tumor cells for alkylating agents only emerged in vivo mainly as a result of host-tumor interactions and could not be detected by unicellular culture models (Science 247:1457-1461 (1990)). The MDR phenotypes of cancers have only be recapitulated by culture models that incorporate elements mimicking in vivo tumor or tissue architectures instead of conventional monolayer cell cultures (Proc. Natl. Acad. Sci. U.S.A. 90, 3294-3298 (1993)). For instance, organization of tumor cells into three-dimensional (3D) multicellular spheroids endowed resistance to cytotoxic agents and radiation, which was reversible by disaggregation of the structures (Anticancer Drug Dev. 14:153-168 (1999); Crit. Rev. Oncol. Hematol. 36:193-207 (2000)).

A variety of mechanisms have been proposed for the development of MDR in tumor cells in 3D multicellular spheroids, including hypoxia, cellular attachment, cell cycle proteins such as KIP1, and cell surface signaling such as the phatidylinositol 3-kinase pathway (Nature Med. 2:1204-1210 (1996); Anticancer Drug Dev. 14:153-168 (1999); Anticancer Drug Dev. 14:169-177 (1999)). When maintained ex vivo with preserved tissue architecture, malignant tumors displayed differential sensitivities to cytotoxic drugs similar to those observed in vivo (Proc. Natl. Acad. Sci. U.S.A. 84:5029-5033 (1987)). The context-dependency of cell death sensitivity also holds true for non-neoplastic epithelial cells, as organization of mammary epithelial cells into 3D acinar architectures in response to reconstituted basement membrane (rBM) endowed them a MDR phenotype (Cancer Cell 2:205-216 (2002)).

Cell development and differentiation are governed by the hierarchical order of gene activation and repression controlled at the level of chromatin structures by epigenetic mechanisms. Epigenetic changes are heritable changes in gene expression that do not involve an alteration in the DNA sequence, which commonly involve changes in the patterns of modifications of DNA and histones, including methylation, acetylation, and phosphorylation, as well as in the architecture of the chromatin conformation (J. Cell Sci. 116:2117-2124 (2003)). Disruptions of the epigenetic regulation of chromatin structure, function, and gene expression therefore leads to the dysregulated of cell growth and differentiation, as well as cancer. Consistent with this view, there is now circumstantial evidence supporting the epigenetic progenitor model in favor of the classical clonal genetic model of cancer (Nat. Rev. Genet. 7:21-33 (2005)). Epigenetic alterations, such as global DNA hypomethylation and chromatin hyperacetylation, are found at very early stages of tumorigenesis. On the other hand, hypermethylation and chromatin hypoacetylation on selective promoters are common strategies which tumor use to silence selective tumor-suppressor genes, such as retinoblastoma 1 (RB1), p16 (CDKN2A), von Hippel-Lindau tumor suppressor (VHL), and MutL protein homologue 1 (MLH1).

Histone hypoacetylation can be caused by inactivation of histone acetylase (HAT) activity due to gene mutations, inhibitory action of viral oncoproteins, and chromosomal translocations. For instance, mutations in CBP and P300 are associated with cancer predisposition (Trends Genet. 14:178-183 (1998), Nat. Genet. 24:300-303 (2000)). Fusion proteins involving MLL (mixed-lineage leukemia) or MORF (monocytic-leukemia-zinc-finger-protein related factor) and p300 or CBP have been associated with acute myelogenous leukemia (AML) (Blood 92:2118-2122 (1998), Hum. Mol. Genet. 10:395-404 (2001)). Histone hypoacetylation and tumorigenesis can also be caused by altered histone deacetylase (HDAC) activities. For instance, chromosomal translocation events in acute promyelocytic leukemia (APL) produce fusion proteins that contain retinoid acid receptor (RAR)α and PML (promyelocytic leukemia protein), and RARα and PLZF (promyelocytic zinc finger), which recruit HDACs with high affinity and result in constitutive repression of RAR-targeted genes (Oncogene 20:7204-7215 (2001)). Moreover, the fusions proteins AML1-ETO and TEL-AML1, expressed in AML and acute lymphoblastic leukemia, recruit HDACs and repress the AML1 transcriptional factor (Oncogene 20:5660-5679 (2001)). Inappropriate transcriptional repression mediated by HDACs may also operate in the tumorigenesis of solid tumors, although the precise mechanisms remain incompletely understood.

Epigenetic alterations not only play important roles in tumor initiation but may also contribute to malignant progression. Phenotypic plasticity mediated by epigenetic mechanisms has now been recognized as an important source of cancer-cell heterogeneity driving phenotypic evolution of tumors. For example, DNA hypomethylation can drive genomic instability as a result of decondensation of centromeric heterochromatin and the formation of new centromeres (Hum. Genet. 67:257-263 (1984)). A reduction in heterochromatin-associated protein 1 ($HP1^{HS\alpha}$), a nonhistone chromosomal protein that mediates transcriptional repression, is directly associated with breast tumor cell invasion and metastasis (Cancer Res. 60:3359-3363 (2000)). Recently, the polycomb group protein EZH2, a histone methyltransferase that causes gene silencing, was found to be overexpressed in metastatic prostate cancer and invasive breast cancer and promotes the proliferation and invasion of tumor cells through its interaction with HDAC2 (Nature 419:624-629 (2002), Proc. Natl. Acad. Sci. USA 100:11606-11611 (2003)). EZH2 was also found to be an independent predictor of prostate and breast cancer recurrence and death. Moreover, it was reported that the gene expression pathway associated with Bmi-1, a component of the chromatin remodeling complex PRC1 (polycomb repressive complex 1), which mediates ubiquitination of histone H2A, strongly predicts recurrence, metastasis, and death in various types of human cancers (J. Clin. Invest. 115:1503-1521 (2005)). If epigenetic plasticity is a common strategy used by tumor cells to evolve into more advanced malignant states, it's likely that more epigenetic regulators will be identified as contributors to tumor progression.

Epigenetic changes alter the expression of a large number of genes and may lead to a higher and faster phenotypic plasticity, through which tumor cells can adapt to new environments such as cytotoxic drug therapy, than genetic changes. Consistent with this possibility, there is now increasing evidence suggesting that epigenetic changes of malignant tumor cells may be a crucial driving force behind the acquisition of drug resistance (Br. J. Cancer 94:1087-1092 (2006)). For instance, methylation of CpG islands in genes involved in DNA repair, including BRCA1, GSTP1, and MGMT, was associated with increased response to chemotherapy in human ovarian cancers (Cancer Res. 65:8961-8967 (2005); N. Engl. J. Med. 343:1350-1354 (2000)). In contrast, methylation and epigenetic inactivation of the proapoptotic gene APAF1 is common in metastatic melanoma and confer resistance to conventional chemotherapy (Nature 409:207-211 (2001)). Similarly, a subset of patients with ovarian cancer acquired methylation of the DNA mismatch repair protein hMLH1 during chemotherapy, which was associated with poor overall survival (Clin. Cancer Res. 10:4420-4426 (2004)).

As mentioned, inappropriate transcriptional repression by altered HDAC activities is a common epigenetic mechanism used by oncoproteins and plays a significant role in tumorigenesis (Nat. Rev. Drug Disc. 1:287-299 (2002)). Currently, compounds that bind and inhibit a broad genus of HDACs are in phase I and II clinical trials for their potentials as antitumor agents (Nat. Rev. Cancer 6:38-51 (2006)). These HDAC inhibitors induce histone hyperacetylation, reactivate suppressed genes, and have pleiotropic cellular effects. Most promisingly, HDAC inhibitors has been shown to induce apoptosis in MDR tumor cells and to sensitize them to chemotherapeutic agents or ionizing radiation through activation of both the death-receptor and intrinsic apoptotic pathways (Int. J. Cancer 104:579-586 (2003); Cancer Res. 63:4460-4471 (2003); Oncogene 24:4609-4623 (2005); Nat. Rev. Drug Disc. 1:287-299 (2002)).

HDACs alone or in combination with DNA-demethylating agents have been shown to increase sensitivity to chemotherapeutic agents in cell line models (Anticancer Drugs 13:869-874 (2002)) and are currently being assessed for their potentials as chemosensitizers in clinical trials. However, the key cellular targets of HDAC inhibitors, as well as patients and tumor types that most likely respond to HDAC inhibitors, remain unknown. Moreover, the inhibitors currently in clinical trials do not demonstrate specificity for individual HDACs. This is a significant problem, as individual HDACs have differential substrate specificities and functions. Determining which of these activities most readily effects tumorogenesis is critical for the efficient targeting of individual molecules. Thus, the use of HDAC inhibitors in clinical studies has very limited success to date (Nat. Rev. Drug Disc. 1:287-299 (2002)).

Given the pleiotropic effects of HDAC inhibitors on a wide variety of histone and non-histone substrates (Nat. Rev. Cancer 6:38-51 (2006)), it is unlikely that a single surrogate marker, such as the genomic level of histone acetylation, can serve as a predictor for drug efficacy. As HDAC inhibition can induce alterations in the transcription of a large number (up to 20% of known genes) of genes (Mol. Cancer. Ther. 2:151-163 (2003); Proc. Natl. Acad. Sci. USA 101:540-545 (2004); Proc. Natl. Acad. Sci. USA 102:3697-3702 (2005)), transcriptional profiles associated with HDAC mutation or inhibition may show particular promise in the prediction of response to HDAC inhibitors.

The Nuclear Corepressor 2 (N-CoR2) (gene symbol: NCOR2; NCBI RefSeq #NM_006312; UniGene ID Hs.137510) and its paralog N-CoR (gene symbol: NCOR1; NCBI RefSeg #NM_006311; UniGene ID Hs.462323) are epigenetic regulators that mediate transcriptional repression by recruiting and activating various histone deacetylases (HDACs) (Annu. Rev. Physiol. 66:315-360 (2004)). N-CoR2 and N-CoR were originally identified as transcriptional corepressors of unliganded nuclear receptors, such as retinoic acid and thyroid hormone receptors (Nature 377:454-457 (1995)). It has become increasingly evident that N-CoR2 and N-CoR also mediate repression of a wide array of non-receptor transcriptional factors, including the myogenic specific bHLH protein MyoD (Mol. Endocrinol. 13:1155-1168 (1999)), B-Myb (Mol. Cell. Biol. 22, 3663-3673 (2002)), the Pbx family of homeobox genes (Mol. Cell. Biol. 19:8219-8225 (1999)), the signal transducers and activators of transcription-5 (STAT5) (EMBO J. 20:6836-6844 (2001)), the oncoproteins PLZF-RAR (Nature 391:811-814 (1998)) and LAZ3/BCL6 (Proc. Natl. Acad. Sci. U.S.A. 94:10762-10767 (1997)), scrum response factor (SRF), activating protein-1 (AP-1), and nuclear factor-κB (NFκB) (J. Biol. Chem. 275: 12470-12474 (2000)).

Biochemical purification of the N-CoR2/N-CoR complexes demonstrated that both N-CoR2 and N-CoR exist in large protein complexes comprising GPS2 (G-protein pathway suppressor 2), which mediates inhibition of the JNK pathway (Cell 9:611-623 (2002)), TBL-1 (transducin β-like protein 1) and TBL-R1, which serve as E3 ligases that recruit the ubiquitin conjugating/19S proteosome complex and thereby degrades the N-COR2/N-CoR complex (Gene Dev. 14:1048-1057 (2000), Cell 116:511-526 (2004)), and HDAC3, which exhibits histone deacetylase activities. Interestingly, the purified N-CoR2—HDAC3 complex possesses deacetylase activity, whereas HDAC3 alone does not function as a HDAC, suggesting that N-CoR2 or N-CoR not only serves as the adaptor but also the activator of the HDAC3 enzymatic activity (Mol. Cell. Biol. 21:6091-6101 (2001)). Biochemistry studies have further shown that a particular deacetylase activation domain of N-CoR2 is required for the activation of the otherwise inert HDAC3 (Proc. Natl. Acad. Sci. USA 102:6009-6014 (2005)).

To date, most of the studies on N-CoR or N-CoR2 have been focused on protein biochemistry and their role in hormone receptor signaling and much less was known about their other biological functions. Recently, aside form its nuclear receptor corepressor functions, N-CoR has been found to play important roles in differentiation (Mol. Endocrinol. 13:1155-1168 (1999)) and stem cell maintenance (Nature 419:934-939 (2002)). Similarly, N-CoR2 was also found to be involved in forebrain development and in maintenance of the neural stem cell state in mice (Nature 450:415-420 (2007)).

Recent advances in high-throughput analytical tools that can measure the expression of a large number of genes have enabled molecular profiling of human malignant tumors. This has greatly enhanced tumor classification and allows for prediction of disease progression and clinical outcome. For instance, unsupervised hierarchical clustering on gene expression data allowed the classification of breast cancers into several distinct subgroups or molecular subtypes (Proc. Natl. Acad. Sci. USA 100:8418-8423 (2003)). In a second study, a 32-gene molecular classifier was used to place human bladder cancers into subclasses with prognostic significance (Nat. Genet. 33:90-96 (2003)). Gene expression profiling in another study allowed the classification of high-grade gliomas with higher accuracy and reproducibility (Cancer Res. 63:1602-1607 (2003)). Molecular profiling of childhood medulloblastomas demonstrated their distinct molecular and clinical features from other types of brain tumors (Nature 415:436-442 (2002)). A 133-gene signature accurately predicted survival among patients with acute myeloid leukemia (N. Engl. J. Med. 350:1605-1616 (2004)). Furthermore, a 70-gene or 76-gene prognostic signature has been developed which successfully predicts survival in patients with breast cancer (N. Engl. J. Med. 347:1999-2009 (2002); Lancet 365: 671-679 (2005)). Gene expression signatures have also successfully predicted clinical outcome of prostate cancers (J. Clin. Invest. 113:913-923 (2004)). A more "universal" signature comprising 128 genes have been developed, which could distinguish primary and metastatic adenocarcinomas of diverse origin and primary tumors carrying the signature were associated with metastasis and poor clinical outcome (Nat. Genet. 33:49-54 (2003)).

Aside from the predictive value for long-term disease outcome, it is increasingly recognized that molecular characteristics, such gene expression profiles, of malignant tumors also affect their sensitivity to adjuvant (post-operative) or neo-adjuvant (pre-operative) chemotherapy (Nat. Clin. Pract. Oncol. 3:621-632 (2006)). To this end, several multigene signatures have been developed to predict patient response to preoperative chemotherapy in breast cancers based on the gene expression profiles of tumor biopsies (J. Clin. Oncol. 24:4236-4244 (2006); J. Clin. Oncol. 22:2284-2293 (2004); J. Clin. Oncol. 23:7265-7277 (2005); J. Transnational Med. 3:32 (2005)). Of note, these signatures were extracted by combining mathematical and statistical methods and none of them were directly related to a cellular pathway that is involved in the process of cell death, stress response, or drug metabolism. As such, a rationale approach to treat resistant malignant tumors based on the gene expression signatures has been hampered by the lack of biological relevance thereof. Recently, Nevins et al. have developed gene expression signatures that reflect the patterns of oncogenic pathway deregulation, which can be used to predict the sensitivity to therapeutic agents that target the deregulated pathway identified (Nature 439:353-357 (2006); Nat. Med. 12:1294-1300 (2006)). An experimentally derived gene-expression signature of the interferon (INF)-related DNA damage signaling pathway was found to be a therapy-predictive marker of adjuvant chemotherapy or radiation in breast cancer (Proc. Natl. Acad. Sci. U.S.A. 105:18490-18495 (2008)). It is conceivable that gene expression signatures associated with particular cellular pathways like these examples can offer a better opportunity to guide the use of pathway-specific drugs and is of considerable value in a more rationalized design of chemotherapies for human malignancies.

The current invention satisfies a need in the art for such a gene expression signature associated with multidrug resistance and HDAC activity in tumor cells.

BRIEF SUMMARY OF THE INVENTION

The current invention relates to the identification of the epigenetic regulators N-CoR2 and HDAC3 as biomarkers for the diagnosis and prognosis of malignant tumors resistant to anti-tumor therapeutics Also identified herein are additional marker genes associated with N-CoR2 and HDAC3, which are useful in the diagnosis and prognosis of treatment resistant tumors. The transcript or protein expression levels of the markers identified in the present invention can be used to distinguish malignant tumors with higher probabilities of not responding to multiple anti-tumor therapeutics, such as chemotherapy, immunotherapy, hormone therapy, and radiotherapy, from those tumors with lower probabilities of treatment resistance.

The present invention also provides methods of sensitizing treatment resistant tumors to anti-cancer therapeutics. In one embodiment, these methods comprise the downregulation of N-CoR2 and/or HDAC3 gene expression or inhibition of protein activity or synergy. Also embodied in the current invention are methods of identifying compounds useful for the treatment of treatment resistant tumors. These methods include in vivo, in vitro, and ex vivo identification of compounds that downregulate the expression level of N-CoR2, HDAC3, or associated signature marker genes as well as compounds that inhibit protein function, activation, or interaction.

Methods for identifying biomarkers associated with the gene signature of histone deacetylases (HDACs) are also disclosed herein. Marker genes identified by the methods of the invention are useful for the diagnosis and prognosis of multidrug resistant tumors.

The invention further provides a method for predicting responsiveness of a malignant tumor to one or more modalities of anti-tumor therapeutics and clinical prognosis comprising steps of: (a) obtaining one or more samples of a tumor from a patient with a malignant tumor; (b) determining mRNA or protein expression levels of at least one biomarker selected from the group consisting of N-CoR2, HDAC3, and a those listed in Table 1 in said tumor sample; (c) comparing the expression levels of said at least one biomarker in said tumor sample to one or a plurality of threshold reference levels; and (d) assigning the malignant tumor a treatment response or clinical prognosis group based on the comparison(s) in (c). Said threshold reference levels are determined by a method comprising steps of: (e) obtaining samples of tumors from a large number of patients with the same type of said malignant tumor and whose clinical prognosis data are available; (f) determining the expression levels of at least one biomarker in said samples; (g) rank ordering in descending order said large number of patients according to the expression levels of said at least one biomarker; and (h) determining one or a plurality of threshold reference levels wherein said malignant tumor patients whose tumors have expression levels of said at least one biomarker above said threshold reference level(s) are predicted as having a higher risk of non-responsiveness to said anti-tumor therapy and/or a higher risk of poor clinical prognosis than those with expression levels below said threshold reference level(s).

The invention further provides an alternative method for predicting responsiveness of a malignant tumor to one or more modalities of anti-tumor therapy or clinical prognosis comprising steps of: (a) obtaining one or more samples of a tumor from a patient with a malignant tumor, (b) determining expression levels of at least one biomarker selected from the group consisting of N-CoR2, HDAC3, and those found in Table 1 in said tumor samples, (c) determining the similarity levels between the expression levels of said markers in said tumor sample and a multidrug resistance signature, (d) comparing said similarity level in said tumor sample to one or a plurality of threshold similarity level(s), and (e) assigning the malignant tumor a treatment response or clinical prognosis group based on the comparisons in (d).

Threshold similarity levels may be determined by a method comprising steps of: (a) obtaining samples of tumors from a large number of patients with the same type of said malignant tumor and whose clinical follow-up and prognosis data are available; (b) determining expression levels of at least one biomarker selected from the group consisting of N-CoR2, HDAC3, and those found in Table 1, in said samples; (c) determining the similarity levels between expression levels of said markers in said tumor sample from said large number of patients; (d) rank ordering in descending order said large number of patients according to said similarity levels; and (e) determining one or a plurality of said threshold similarity level(s) wherein said malignant tumor patients whose tumors have similarity levels associated with N-CoR2HDAC3 above said threshold similarity level(s) are predicted as having a higher risk of non-responsiveness to said anti-tumor therapy and/or a higher risk of poor clinical prognosis than those with similarity levels below said threshold similarity level(s).

In a specific embodiment of the above method, determining the similarity levels between marker expressions comprises the use of a statistical algorithm, including Pearson's, Spearman's or Kendall's correlation coefficient determination method or the like.

The invention further provides a method for assessing the ability of a candidate compound to increase the sensitivity of a malignant tumor cell to one or more modalities of anti-tumor therapy comprising steps of: (a) contacting a mammalian cell with a compound; (b) determining the nuclear deacetylase activity of HDAC3 or the mRNA or protein levels of a biomarker selected from the group consisting of N-CoR2, HDAC3, and those listed in Table 1, in said first mammalian cell and in a second mammalian cell that is not contacted with the compound; (c) comparing the deacetylase activity of HDAC3 or the expression levels of said biomarkers in said mammalian cells; (d) classifying the compound as having a ability to increase the sensitivity to an anti-tumor therapy if the deacetylase activity or the expression levels of said biomarkers in said first mammalian cell are different than those in said second mammalian cell.

In certain embodiments of the invention, the sensitivity of a malignant tumor to anti-tumor therapy is assessed by methods including measuring the size, the number of living tumor cells, or the extent of vascularization of said tumor after said anti-tumor therapy, or evaluating the number and the size of local recurrent tumors or local or distant metastasis thereof at varying lengths of time after said anti-tumor therapy.

In a particular embodiment of the invention, increasing the sensitivity of a malignant tumor to anti-tumor therapy comprises local or systemic administration of a therapeutically effective amount of a mutant N-CoR2 protein that is deficient in its physical interaction with HDAC3 or unable to activate its deacetylase activity in the host of said malignant tumor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 The expression profile of the gene probes in NCOR2-42 from the 80 estrogen receptor (ER)-positive breast tumors (upper panel sheet 1) and those in NCOR2-45 from the 50 ER negative breast tumors (lower panel sheet 2) in the M.D. Anderson Cancer Center data set. In each subset, the tumors are ranked descendingly according to $r_{ANP}$ (right panels) and those with correlation coefficients higher than a cut-off value (solid line) is assigned to the non-responder group while that with a correlation coefficient lower than the cut-off value is assigned to the responder group. Yellow circles, responders; black circles, non-responders.

FIG. 12 Growth rates and 3D acini formation of HMT3522 S1 cells with stable downregulation of N-CoR2 expression and their control cells. Bar, 500 µm.

DETAILED DESCRIPTION OF THE INVENTION

Figure 1A:
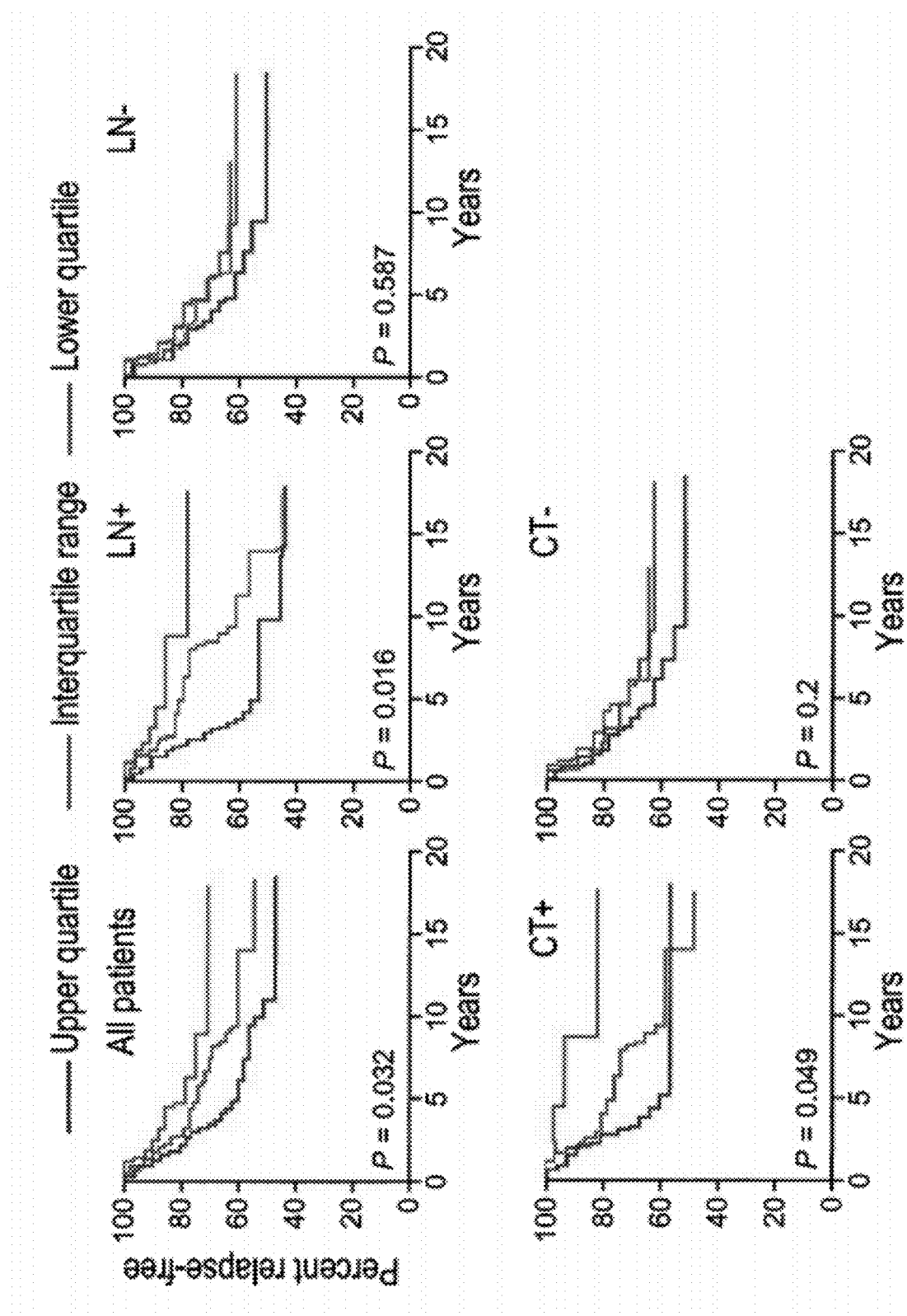
FIG. 1 The probability of remaining relapse-free (FIG. 1A) or survive (FIG. 1B) as a function of time from diagnosis among 295 breast cancer patients in the Netherlands Cancer Institute data set. The patients were grouped into quartiles according to the expression levels of N-CoR2. The patients were further stratified according to their LN status and whether or not they received adjuvant systemic chemotherapy (CT). Patients in each group were stratified according to N-CoR2 gene expression quartiles.

The present invention relates to methods for diagnosing, predicting, and treating malignant tumors that are resistant to anti-tumor therapeutics including chemotherapy, immunotherapy, hormone therapy, and radiation. The present invention provides novel methods of using the deacetylase activity or expression levels of nuclear co-repressor 2 ("N-CoR2"), histone deacetylases 3 ("HDAC3"), or associated gene expression markers and profiles to predict or diagnose the presence of multidrug resistant malignant tumors. In addition, the present invention also provides methods of increasing the sensitivity of malignant tumors to anti-tumor therapeutics by inhibiting N-CoR2, HDAC3, or associated gene expression markers or by disrupting the interaction between N-CoR2 and HDAC3.

In one embodiment, the methods of diagnosing or providing a prognosis for multidrug resistant tumors comprise the identification of the differential expression of one or more of the biomarkers identified herein. Methods embraced in the identification of expression levels include RT-PCR, qRT-PCR, microarray hybridization, mass spectroscopy, ELISA, and immunochemistry. In some embodiments, the cancer is breast cancer, malignant gliomas, ovarian cancer, or any other well known cancer.

The present invention provides kits for the diagnosis or prognosis of multigene resistant tumors. These kits comprise one or more probes for the detection of biomarkers identified by the present invention. In certain embodiments, the kits provided by the current invention comprise probes for the identification of any 1, 2, 3, 4, 5, 10, 15, 20, 25, or more biomarkers selected from the group consisting of N-CoR2, HDAC3, and those listed in Table 1. In another embodiment, the kit comprises probes for the identification of N-CoR2, HDAC3, and those genes listed in Table 1. In some embodiments, the kit comprises a microarray. In other embodiments, the kit comprises an ELISA assay or cocktail of antibodies. In yet other embodiments, the kit comprises reagents for the RT-PCR or qRT-PCR identification of marker gene expression. In particular embodiments, the diagnosis or prognosis is further generated by a computer or provided by a computer generated print out.

Probes useful in the methods and kits of the present invention include nucleic acids, such as oligonucleotides of DNA, RNA, and analogs thereof, as well as antibodies and immunoreactive fragments thereof.

This present invention also provides methods of identifying marker genes associated with N-CoR2, HDAC3, or a histone deacetylase, that are useful in the prognosis or diagnosis of malignant tumors resistant to anti-tumor therapeutics. The invention also relates to the identification and use in diagnosis or prognosis of sets of marker genes that are regulated by N-CoR2, HDAC3, a histone deacetylase, or combinations thereof in normal or malignant cells. The transcription or protein expression levels of biomarkers identified herein, or identified by the methods described herein, can further be used to distinguish or classify malignant tumors with high or low probabilities of responding to multiple anti-tumor therapies. In one embodiment, the methods for identifying biomarkers comprise cell growth in a 3D culture matrix. In a particular embodiment, the method comprises cell growth on a reconstituted basement membrane.

Compounds useful for treating or sensitizing multidrug resistant tumors are provided in the current invention. In one embodiment, these compounds down-regulate markers including N-CoR2, HDAC3, and those found in Table 1. In other embodiments, these compounds inhibit the activity, activation, or coordination of N-CoR2, HDAC3, markers listed in Table 1, and combinations thereof. Compounds of the invention include, nucleic acids, antisense oligonucleotides, siRNAs, shRNAs, microRNAs, ribozymes, proteins, peptides, antibodies, immuno-reactive fragments, small organic molecules and the like. The present invention also provides methods of treating multi drug resistant tumors or cancers through use of the compounds identified in the present invention.

This invention further provides methods for identifying compounds useful in treating or increasing the sensitivity of a tumor cell to anti-tumor therapeutics and methods for increasing the sensitivity of a tumor to an anti-tumor therapeutics by inhibiting the activity of N-CoR2, HDAC3, the N-Cor2/HDAC3 protein complex, or associated biomarkers. In one embodiment, these methods comprise in vivo, in vitro, or ex vivo assays to identify compounds that alter the expression of N-CoR2, HDAC3, or any gene listed in Table 1. In other embodiments, the methods comprise in vivo, in vitro, or ex vivo assays to identify compounds that inhibit the function, activation, or interaction of N-CoR2, HDAC3, or any gene listed in Table 1.

The present invention provides methods of diagnosing a multidrug resistant tumor in a subject. In one embodiment, the method comprises the steps of first analyzing a tumor sample from the subject with an assay that specifically detects a marker selected from the group consisting of N-CoR2, HDAC3, and those listed in Table 1, then determining whether or not the marker is differentially expressed (over or under expressed), and finally determining if the differential expression correlates with a multidrug resistance signature, thereby providing a diagnosis for a mulitidrug resistant tumor.

Particular embodiments of the present invention provide methods of providing a prognosis for a metastatic cancer. In one embodiment, the method comprises the steps of analyzing a tumor sample from a subject with an assay that specifically detects a marker selected from the group consisting of N-CoR2, HDAC3, and those listed in Table 1, then determining whether or not the marker is differentially expressed (over or under expressed), and finally determining if the differential expression correlates with a multidrug resistance signature, thereby providing a prognosis for a metastatic cancer. In one embodiment, a positive correlation with a multidrug resistance signature indicates a poor prognosis. In another embodiment, the subject is a mammal, such as a rat, mouse, hamster, cow, pig, horse, sheep, or human. In one particular embodiment, the prognosis is expressed as a probability that the patient would remain relapse-free or survive for a given number of years after being diagnosed with cancer.

Methods of identifying a compound useful for the treatment or sensitization of multidrug resistant tumors are embodied by the present invention. In one particular embodiment, the method comprises the steps of first contacting a multi drug resistant tumor cell with a compound and then determining the expression level of N-CoR2 or HDAC3 in said contacted cell relative to the expression level of N-CoR2 or HDAC3 in a reference tumor cell not contacted by said compound, wherein downregulation of N-CoR2 or HDAC3 in the contacted cell relative to the reference cell indicates that the compound is useful for the treatment of multidrug resistant tumors. In other embodiments, the marker or markers being detected comprise one or more genes listed in Table 1.

In another embodiment, the method comprises the steps of contacting a mixture of N-CoR2 and HDAC3 proteins with a compound and then determining the extent of the interaction between N-CoR2 and HDAC3, wherein a reduced interaction between N-CoR2 and HDAC3 after contacting the mixture with the compound indicates that the compound is useful for the treatment of multidrug resistant tumors. In other embodiments, the method further comprises the use of a biomarker listed in Table 1.

In yet another embodiment, the method comprises the steps of contacting an HDAC3 protein with a compound and determining the activity of said HDAC3 protein, wherein a reduced activity of said HDAC3 protein indicates that the compound is useful for the treatment of multidrug resistant tumors. In another embodiment, the protein being contacted is selected from the group consisting of N-CoR2, those listed in Table 1, and an HDAC.

The current invention also provides methods for identifying biomarkers useful for the diagnosis or prognosis of multidrug resistant tumors. In one embodiement, the method comprises the steps of identifying multidrug resistant tumors differentially expressing a histone deacetylase (HDAC), and identifying marker genes differentially expressed in said multidrug resistant tumor, thereby identifying biomarkers useful for the diagnosis or prognosis of multidrug resistant tumors. In one particular embodiment, the HDAC is a class I, class II, class III, or class IV enzyme. In another embodiment, the HDAC is an ATP-dependent or NAD-dependent enzyme.

DEFINITIONS

As used herein, "multi-drug resistance" or "multidrug resistant" refers to a classification in which a tumor is not responsive to more than one anti-tumor therapeutic. Anti-tumor therapeutics are well known in the art and include, but are not limited to, cytotoxic drugs, hormone therapy, biologics such as antibodies or fragments thereof, chemotherapy, and radiation therapy.

A "multidrug resistance signature" or "multidrug resistance gene (or marker or biomarker) signature" refers to the transcriptional profile of one or more associated marker genes as it is differentially expressed in a multidrug resistant cell or tumor. In this fashion, a marker that is overexpressed would correspond to a multidrug resistance signature if said gene was previously shown to be overexpressed in a multidrug resistant tumor or cell.

Histone deacetylases (HDACs) are enzymes which deacetylate the amino-terminal tails of histones, regulating chromatin assembly, mRNA transcription and other nuclear events. A number of human HDACs are well known in the art and include, but are not limited to, class 1 deacetylases, including HDAC1, HDAC2, HDAC3, and HDAC8, class II deacetylases, including HDAC4, HDAC5, HDAC6, HDAC7A, HDAC9, and HDAC10, class III deacetylases, including ScSir2 homologues, SIRT1, SIRt2, SIRT3, SIRT4, SIRT5, SIRT6, and SIRT7, and class IV deacetylases, including HDAC11. HDAC can be NAD-dependent or ATP-dependent enzymes.

"N-CoR2", "HDAC3", and other biomarkers recited herein, including those found in Table 1, refer to nucleic acids, e.g., gene, pre-mRNA, mRNA, and polypeptides, polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 60% nucleotide sequence identity, 65%, 70%, 75%, 80%, 85%, 90%, preferably 91%, 92%, 93%, 94%, 95%, 96%, 97%, 98% or 99% or higher nucleotide sequence identity, preferably over a region of at least about 10, 15, 20, 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

"Cancer" refers to mammalian cancers, especially human cancers, and carcinomas, sarcomas, adenocarcinomas, lymphomas, leukemias, etc., including solid and lymphoid cancers, kidney, breast, lung, kidney, bladder, colon, ovarian, prostate, pancreas, stomach, brain, head and neck, skin, uterine, testicular, esophagus, and liver cancer, including hepatocarcinoma, lymphoma, including non-Hodgkin's lymphomas (e.g., Burkitt's, Small Cell, and Large Cell lymphomas) and Hodgkin's lymphoma, leukemia, and multiple myeloma. Cancers embraced in the current application include both metastatic and non-metastatic cancers.

"Therapeutic treatment" and "cancer therapies" refers to chemotherapy, hormonal therapy, radiotherapy, and immunotherapy.

"Sensitize" or "sensitizing" refers to the effect of rendering a cell, usually a cancer or multidrug resistant cancer cell or tumor in the context of the present invention, more susceptible to an anti-proliferative or anti-cancer treatment. In this fashion, a sensitizing activity is the effect of use of an agent that if used alone would not demonstrate significant anti-tumor effects but would improve the anti-tumor effects of an anti-proliferative or anti-cancer agent in a more than additive fashion than the use of the anti-proliferative agent by itself.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins)

The terms "overexpress", "overexpression", "overexpressed", "up-regulate", or "up-regulated" interchangeably refer to a biomarker that is transcribed or translated at a detectably greater level, usually in a cancer cell or a multidrug resistant cancer cell, in comparison to a non-cancer cell or cancer cell that is not multidrug resistant. The term includes overexpression due to transcription, post transcriptional processing, translation, post-translational processing, cellular localization (e.g, organelle, cytoplasm, nucleus, cell surface), and RNA and protein stability, as compared to a non-cancer cell. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold 5, 6, 7, 8, 9, 10, or 15-fold or more higher levels of transcription or translation in comparison to a non-cancer cell.

The terms "underexpress," "underexpression", "underexpressed" or "downregulated" interchangeably refer to a protein or nucleic acid that is transcribed or translated at a detectably lower level usually in a cancer cell or a multidrug resistant cancer cell, in comparison to a non-cancer cell or a cancer cell that does not have multidrug resistance. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-fold, 2-fold, 3-fold, 4-fold or more lower levels of transcription or translation in comparison to a control.

The term "differentially expressed" or "differentially regulated" refers generally to a protein or nucleic acid that is overexpressed (upregulated) or underexpressed (downregulated) in one sample compared to at least one other sample, generally in a cancer cell that has multidrug resistance, in comparison to a cell or patient without cancer or in a cancer cell that is not multidrug resistant, in the context of the present invention.

The terms "cancer-associated antigen", "tumor-specific marker", "tumor marker", "maker", or "biomarker" interchangeably refer to a molecule (typically protein or nucleic acid such as RNA) that is differentially expressed in the cell, expressed on the surface of a cancer cell or secreted by a cancer cell in comparison to a non-cancer cell, and which is useful for the diagnosis of cancer, for providing a prognosis, and for preferential targeting of a pharmacological agent to the cancer cell. Oftentimes, a cancer-associated antigen is a molecule that is overexpressed or underexpressed in a cancer cell in comparison to a non-cancer cell, for instance, 1-fold over expression, 2-fold overexpression, 3-fold overexpression or more in comparison to a non-cancer cell or, for instance, 20%, 30%, 40%, 50% or more underexpressed in comparison to a non-cancer cell. Oftentimes, a cancer-associated antigen is a molecule that is inappropriately synthesized in the cancer cell, for instance, a molecule that contains deletions, additions or mutations in comparison to the molecule expressed in a non-cancer cell. Oftentimes, a cancer-associated antigen will be expressed exclusively on the cell surface of a cancer cell and not synthesized or expressed on the surface of a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal. Other times, a cancer-associated antigen will be expressed primarily not on the surface of the cancer cell.

It will be understood by the skilled artisan that markers may be used singly or in combination with other markers for any of the uses, e.g., diagnosis or prognosis of multidrug resistant cancers, disclosed herein.

"Biological sample" includes sections of tissues such as biopsy and autopsy samples, and frozen sections taken for histologic purposes. Such samples include breast cancer tissues, blood and blood fractions or products (e.g., serum, plasma, platelets, red blood cells, and the like), sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., breast, etc.), the size and type of the tumor, among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy", or a "fine-needle aspiration biopsy" which generally obtains a suspension of cells from within a target tissue. Biopsy techniques are discussed, for example, in *Harrison's Principles of Internal Medicine*, Kasper, et al., eds., 16th ed., 2005, Chapter 70, and throughout Part V.

The terms "identical" or percent "identity", in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 15 amino acids or nucleotides in length, or more preferably over a region that is 20, 25, 50-100 or more amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr. Madison, Wis.), or by manual alignment and visual inspection (see, e.g., *Current Protocols in Molecular Biology* (Ausubel et al., eds. 1987-2005, Wiley Interscience)).

An example of an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., *J Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, $Proc.\ Natl.\ Acad.\ Sci.\ USA$ 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., $Nucleic\ Acid\ Res.$ 19:5081 (1991); Ohtsuka et al., $J.\ Biol.\ Chem.$ 260:2605-2608 (1985); Rossolini et al., $Mol.\ Cell.\ Probes$ 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer biomarkers. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of antibodies, e.g., recombinant, monoclonal, or polyclonal antibodies, many technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., Nature 321:522-525 (1986); Riechmann et al., Nature 332: 323-327 (1988); Verhoeyen et al., Science 239:1534-1536 (1988) and Presta, Curr. Op. Struct. Biol. 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

Predictive, Diagnostic, and Prognostic Methods

The present invention provides methods of diagnosing a multidrug resistant cancer by examining cancer biomarkers (either the protein or the RNA encoding the protein) such as N-CoR2, HDAC3, and those found in Table 1, or a combination thereof in tissues suspected of being or known to be cancerous, e.g. breast cancer tissue, including wild-type, truncated or alternatively spliced forms. Diagnosis involves determining the level of a polypeptide or polynucleotide of the invention in a patient and then comparing the level to a baseline or range. Typically, the baseline value is representative of a polypeptide or polynucleotide of the invention in a person or tissue not suffering from multidrug resistant cancer, as measured using a tissue sample or biopsy or other biological sample such a serum or blood. Variation of levels of a polypeptide or polynucleotide of the invention from the baseline range (either up or down) indicates that the patient has a multidrug resistant cancer or is at risk of developing a multidrug resistant cancer.

As used herein, the term "providing a prognosis" refers to providing a prediction of the probable course or outcome of a cancer such as breast cancer, including prediction of metastasis, multidrug resistance, disease free survival, overall survival, recurrence, etc. The methods can also be used to devise a suitable therapy for cancer treatment, e.g., by indicating whether or not the cancer is still at an early stage or if the cancer had advanced to a stage where aggressive therapy would be ineffective. The methods can also be used to determine whether or not a tumor or cancer will be responsive or unresponsive to a variety of cancer treatments.

Antibody reagents can be used in assays to detect expression levels of N-CoR2, HDAC3, and markers found in Table 1 in patient samples using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., *Curr. Opin. Biotechnol.,* 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., *Electrophoresis,* 18:2184-93 (1997); Bao, *J. Chromatogr. B. Biomed. Sci.,* 699:463-80 (1997). Liposome immunoassays, such as flow-injection liposome immunoassays and liposome immunosensors, are also suitable for use in the present invention. See, e.g., Rongen et al., *J. Immunol. Methods,* 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, C A; Kit #449430) and can be performed using a Behring Nephelometer Analyzer (Fink et al., *J. Clin. Chem. Clin. Biochem.,* 27:261-276 (1989)).

Specific immunological binding of the antibody to nucleic acids can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), in the physical form of sticks, sponges, papers, wells, and the like. An assay strip can be prepared by coating the antibody or a plurality of antibodies in an array on a solid support. This strip can then be dipped into the test sample and processed quickly through washes and detection steps to generate a measurable signal, such as a colored spot.

Alternatively, nucleic acid binding molecules such as probes, oligonucleotides, oligonucleotide arrays, and primers can be used in assays to detect differential RNA expression of N-CoR2, HDAC3, and markers found in Table 1 in patient samples, e.g., RT-PCR. In one embodiment, RT-PCR is used according to standard methods known in the art. In another embodiment, PCR assays such as Taqman® assays available from, e.g., Applied Biosystems, can be used to detect nucleic acids and variants thereof. In other embodiments, qPCR and nucleic acid microarrays can be used to detect nucleic acids. Reagents that bind to selected cancer biomarkers can be prepared according to methods known to those of skill in the art or purchased commercially.

Analysis of nucleic acids can be achieved using routine techniques such as Southern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression From Experiments to Data Analysis and Modeling," Cambridge University Press, 2002.

Analysis of nucleic acid markers and their variants can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques,* 13:626-633 (1992)), solid-phase sequencing (Zimmerman et al., *Methods Mol. Cell. Biol.,* 3:39-42 (1992)), sequencing with mass spectrometry such as matrix-assisted laser desorption/ionization time-of-flight mass spectrometry (MALDI-TOF/MS; Fu et al., *Nat. Biotechnol.,* 16:381-384 (1998)), and sequencing by hybridization. Chee et al., *Science,* 274:610-614 (1996); Drmanac et al., *Science,* 260:1649-1652 (1993); Drmanac et al., *Nat. Biotechnol.,* 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE) and pyrosequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Useful physical formats comprise surfaces having a plurality of discrete, addressable locations for the detection of a plurality of different markers. Such formats include microarrays and certain capillary devices. See, e.g., Ng et al., *J. Cell Mol. Med.,* 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection. Other useful physical formats include sticks, wells, sponges, and the like.

Analysis can be carried out in a variety of physical formats. For example, the use of microliter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to patient samples immobilized on microscope slides. The resulting antibody staining or in situ hybridization pattern can be visualized using any one of a variety of light or fluorescent microscopic methods known in the art.

Analysis of the protein or nucleic acid can also be achieved, for example, by high pressure liquid chromatography (HPLC), alone or in combination with mass spectrometry MALDI/MS, MALDI-TOF/MS, tandem MS, etc.).

Compositions, Kits and Integrated Systems

The invention provides compositions, kits and integrated systems for practicing the assays described herein using antibodies specific for the polypeptides or nucleic acids specific for the polynucleotides of the invention.

Kits for carrying out the diagnostic assays of the invention typically include a probe that comprises an antibody or nucleic acid sequence that specifically binds to polypeptides or polynucleotides of the invention, and a label for detecting the presence of the probe. The kits may include several antibodies or polynucleotide sequences encoding polypeptides of the invention, e.g., a cocktail of antibodies that recognize N-CoR2, HDAC3, and markers found in Table 1.

Treatment, Compounds for Treatment, and Methods of Identifying Compounds Effective for Treatment A variety of methods may be used to identify compounds that prevent, treat, or sensitize multidrug resistant cancers. Typically, an assay that provides a readily measured parameter is adapted to be performed in the wells of multi-well plates in order to facilitate the screening of members of a library of test compounds as described herein. Thus, in one embodiment, an appropriate number of cells can be plated into the cells of a multi-well plate, and the effect of a test compound on the expression of a biomarker can be determined.

The compounds to be tested can be any small chemical compound, or a macromolecule, such as a protein, sugar, nucleic acid or lipid. Typically, test compounds will be small chemical molecules and peptides. Essentially any chemical compound can be used as a test compound in this aspect of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one embodiment, high throughput screening methods are used which involve providing a combinatorial chemical or peptide library containing a large number of potential therapeutic compounds. Such "combinatorial chemical libraries" or "ligand libraries" are then screened in one or more assays, as described herein, to identify those library members (particular chemical species or subclasses) that display a desired characteristic activity. In this instance, such compounds are screened for their ability to reduce or increase the expression of the biomarkers of the invention.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries are well known to those of skill in the art. Such combinatorial chemical libraries include, but are not limited to, peptide libraries (see, e.g., U.S. Pat. No. 5,010,175, Furka, Int. J. Pept. Prot. Res., 37:487-493 (1991) and Houghton et al., *Nature,* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *PNAS USA,* 90:6909-6913 (1993)), vinylogous polypeptides (Hagihara et al., *J. Amer. Chem. Soc.,* 114:6568 (1992)), nonpeptidal peptidomimetics with glucose scaffolding (Hirschmann et al., *J.*

*Amer. Chem. Soc.,* 114:9217-9218 (1992)), analogous organic syntheses of small compound libraries (Chen et al., *J. Amer. Chem. Soc.,* 116:2661 (1994)), oligocarbamates (Cho et al., *Science,* 261:1303 (1993)), and/or peptidyl phosphonates (Campbell et al., *J. Org. Chem.,* 59:658 (1994)), nucleic acid libraries (see Ausubel, Berger and Sambrook, all supra), peptide nucleic acid libraries (see, e.g., U.S. Pat. No. 5,539, 083), antibody libraries (see, e.g., Vaughn et al., *Nature Biotechnology,* 14(3):309-314 (1996) and PCT/US96/10287), carbohydrate libraries (see, e.g., Liang et al., *Science,* 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, R U, 3D Pharmaceuticals, Exton, Pa., Martek Biosciences, Columbia, Md., etc.).

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100—about 1500 different compounds. It is possible to assay many plates per day; assay screens for up to about 6,000, 20,000, 50,000, or 100,000 or more different compounds is possible using the integrated systems of the invention.

The phrase "functional effects" in the context of assays for testing or identifying compounds that modulate a marker protein includes the determination of a parameter that is indirectly or directly under the influence of a biomarker of the invention, e.g., a chemical or phenotypic parameter. A functional effect therefore includes ligand binding activity, histone deacetylation activity, transcriptional activation or repression, the ability of cells to proliferate, the ability to migrate, among others. "Functional effects" include in vitro, in vivo, and ex vivo activities.

By "determining the functional effect" is meant assaying for a compound that increases or decreases a parameter that is indirectly or directly under the influence of a biomarker of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the marker; measuring changes in enzymatic activity; the ability to increase or decrease cellular proliferation, apoptosis, cell cycle arrest, measuring changes in cell surface markers, measuring histone deacetylation activity, etc. The functional effects can be evaluated by many means known to those skilled in the art, e.g., microscopy for quantitative or qualitative measures of alterations in morphological features, measurement of changes in RNA or protein levels for other genes expressed in placental tissue, measurement of RNA stability, identification of downstream or reporter gene expression (CAT, luciferase, ÿ-gal, GFP and the like), e.g., via chemiluminescence, fluorescence, colorimetric reactions, antibody binding, inducible markers, measuring historic acetylation, etc.

"Inhibitors," "activators," and "modulators" of the markers are used to refer to activating, inhibitory, or modulating molecules identified using in vitro and in vivo assays of cancer biomarkers. Inhibitors are compounds that, e.g., bind to, partially or totally block activity, decrease, prevent, delay activation, inactivate, desensitize, or down regulate the activity or expression of cancer biomarkers. "Activators" are compounds that increase, open, activate, facilitate, enhance activation, sensitize, agonize, or up regulate activity of cancer biomarkers, e.g., agonists. Inhibitors, activators, or modulators also include genetically modified versions of cancer biomarkers, e.g., versions with altered activity, as well as naturally occurring and synthetic ligands, antagonists, agonists, antibodies, peptides, cyclic peptides, nucleic acids, antisense molecules, ribozymes, RNAi and siRNA molecules, microRNA, shRNA, small organic molecules and the like. Such assays for inhibitors and activators include, e.g., expressing cancer biomarkers in vitro, in cells, or cell extracts, applying putative modulator compounds, and then determining the functional effects on activity, as described above.

Samples or assays comprising cancer biomarkers that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of cancer biomarkers is achieved when the activity value relative to the control is about 80%, preferably 50%, more preferably 25-0%. Activation of cancer biomarkers is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, microRNA, polynucleotide, oligonucleotide, etc., to be tested for the capacity to directly or indirectly modulate cancer biomarkers. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Methods to Inhibit Marker Protein Expression Using Nucleic Acids

A variety of nucleic acids, such as antisense nucleic acids, siRNAs, shRNAs, microRNAs, or ribozymes, may be used to inhibit the function of the markers of this invention. Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. In addition, ribozymes possess highly specific endoribonuclease activity, which autocatalytically cleaves the target sense mRNA.

With regard to antisense, siRNA, shRNA, microRNA, or ribozyme oligonucleotides, phosphorothioate oligonucleotides can be used. Modifications of the phosphodiester linkage as well as of the heterocycle or the sugar may provide an increase in efficiency. Phosphorothioate is used to modify the phosphodiester linkage. An N3'-P5' phosphoramidate linkage has been described as stabilizing oligonucleotides to nucleases and increasing the binding to RNA. Peptide nucleic acid (PNA) linkage is a complete replacement of the ribose and phosphodiester backbone and is stable to nucleases, increases the binding affinity to RNA, and does not allow cleavage by RNAse H. Its basic structure is also amenable to modifications that may allow its optimization as an antisense component. With respect to modifications of the heterocycle, certain heterocycle modifications have proven to augment antisense effects without interfering with RNAse H activity. An example of such modification is C-5 thiazole modification. Finally, modification of the sugar may also be considered. 2'-O-propyl and 2'-methoxyethoxy ribose modifications stabilize oligonucleotides to nucleases in cell culture and in vivo.

Inhibitory oligonucleotides can be delivered to a cell by direct transfection or transfection and expression via an expression vector. Appropriate expression vectors include mammalian expression vectors and viral vectors, into which has been cloned an inhibitory oligonucleotide with the appropriate regulatory sequences including a promoter to result in expression of the antisense RNA in a host cell. Suitable promoters can be constitutive or development-specific promoters. Transfection delivery can be achieved by liposomal transfection reagents, known in the art (e.g., Extreme transfection reagent, Roche, Alameda, Calif.; Lipofectamine formulations, Invitrogen, Carlsbad, Calif.). Delivery mediated by cationic liposomes, by retroviral vectors and direct delivery are efficient. Another possible delivery mode is targeting using antibody to cell surface markers for the target cells.

For transfection, a composition comprising one or more nucleic acid molecules (within or without vectors) can comprise a delivery vehicle, including liposomes, for administration to a subject, carriers and diluents and their salts, and/or can be present in pharmaceutically acceptable formulations. Methods for the delivery of nucleic acid molecules are described, for example, in Gilmore, et al., *Curr Drug Delivery* (2006) 3:147-5 and Patil, et al., *AAPS Journal* (2005) 7:E61-E77, each of which are incorporated herein by reference. Delivery of siRNA molecules is also described in several U.S. Patent Publications, including for example, 2006/0019912; 2006/0014289; 2005/0239687; 2005/0222064; and 2004/0204377, the disclosures of each of which are hereby incorporated herein by reference. Nucleic acid molecules can be administered to cells by a variety of methods known to those of skill in the art, including, but not restricted to, encapsulation in liposomes, by iontophoresis, by electroporation, or by incorporation into other vehicles, including biodegradable polymers, hydrogels, cyclodextrins (see, for example Gonzalez et al., 1999, *Bioconjugate Chem.*, 10, 1068-1074; Wang et al., International PCT publication Nos. WO 03/47518 and WO 03/46185), poly(lactic-co-glycolic) acid (PLGA) and PLCA microspheres (see for example U.S. Pat. No. 6,447,796 and US Patent Application Publication No. 2002/130430), biodegradable nanocapsules, and bioadhesive microspheres, or by proteinaceous vectors (O'Hare and Normand, International PCT Publication No. WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

Examples of liposomal transfection reagents of use with this invention include, for example: CellFectin, 1:1.5 (M/M) liposome formulation of the cationic lipid N,NI,NII,NIII-tetramethyl-N,NI,NII,NIII-tetrapalmit-γ-spermine and dioleoyl phosphatidylethanolamine (DOPE) (GIBCO BRL); Cytofectin GSV, 2:1 (M/M) liposome formulation of a cationic lipid and DOPE (Glen Research); DOTAP (N-[1-(2,3-dioleoyloxy)-N,N,N-tri-methyl-ammoniummethylsulfate) (Boehringer Manheim); Lipofectamine, 3:1 (M/M) liposome formulation of the polycationic lipid DOSPA and the neutral lipid DOPE (GIBCO BRL); and (5) siPORT (Ambion); HiPerfect (Qiagen); X-treme GENE (Roche); RNAicarrier (Epoch Biolabs) and TransPass (New England Biolabs).

In some embodiments, antisense, siRNA, shRNAs, microRNA, or ribozyme sequences are delivered into the cell via a mammalian expression vector. For example, mammalian expression vectors suitable for siRNA expression are commercially available, for example, from Ambion (e.g., pSilencer vectors), Austin, Tex.; Promega (e.g., GeneClip, siSTRIKE, SiLentGene), Madison, Wis.; Invitrogen, Carlsbad, Calif.; InvivoGen, San Diego, Calif.; and Imgenex, San Diego, Calif. Typically, expression vectors for transcribing siRNA molecules will have a U6 promoter.

In some embodiments, antisense, siRNA, shRNA, microRNA, or ribozyme sequences are delivered into cells via a viral expression vector. Viral vectors suitable for delivering such molecules to cells include adenoviral vectors, adeno-associated vectors, and retroviral vectors (including lentiviral vectors). For example, viral vectors developed for delivering and expressing siRNA oligonucleotides are commercially available from, for example, GeneDetect, Bradenton, Fla.; Ambion, Austin, Tex.; Invitrogen, Carlsbad, Calif.; Open BioSystems, Huntsville, Ala.; and Imgenex, San Diego, Calif.

EXAMPLES

Example 1

This example describes the identification of genetic markers associated with N-CoR2.

HMT3522 T4-2 malignant human breast epithelial cells, developed by Dr. O. W. Peterson (Cancer Res. 52:1210-1217, 1992), were used as a model. HMT3522 T4-2 cells were derived from an epidermal growth factor (EGF)-dependent breast epithelial HMT3522 S-1 cells and an EGF-independent HMT3522 S-2 cells that spontaneously became malignant when injected into nude mice. HMT3522 T4-2 cells were propagated as monolayers on type I collagen-coated plastic surface in chemically defined medium consisting of DMEM:F12 medium (Invitrogen GIBCO), containing 250 ng/ml insulin (Boehringer Mannheim), 10 µg/ml transferrin (Sigma, St. Louis, Mo.), 2.6 ng/ml sodium splenetic (Collaborative Research), $10^{-10}$ M estradiol (Sigma), $1.4 \times 10^{-6}$ M hydrocortisone (Collaborative Research), and 5 µg/ml prolactin (Sigma), as described in J. Cell Biol. 137:231-245 (1997).

HMT3522 T4-2 cells that stably overexpress N-CoR2 were generated by retrovirus-mediated gene transduction. Briefly, the retroviral construct inducibly expressing HA- and EGFP-epitope tagged N-CoR2 was prepared by subcloning murine NCOR2 cDNA (e isoform, NCBI RefSeq #NM_011424) from pCMX-FLAG-NCOR2 (provided by professor M. A. Lazar, University of Pennsylvania) (Proc. Natl. Acad. Sci. USA 96:3519-3524 (1999)) into pBluescriptII KS+ (Stratagene) for the addition of a N-terminal HA-epitope tag and then recloned into a modified hybrid Epstein-Barr virus/retroviral vector pLZRS-MFG-tet-EGFP that contains a tetracycline regulated promoter and allows stable multicopy episomal replication in the retroviral packaging lines (Hum. Gene Ther. 7:1405-1413 (1996)) to generate the final expression construct pLZRS-MFG-tet-HA-EGFP-NCOR2.

Amphotropic retrovirus was produced in modified 293 cells or in Phoenix ampho cells (provided by Professor G. Nolan, Stanford Medical Center) with packaging vectors pCgp and pVSVG to boost viral titer. Cells were spin infected with retrovirus carrying N-CoR2 or an empty retroviral vector, followed by infection with a high titer MFG virus expressing the tetracycline-controlled transcriptional transactivator produced in the packaging cell line 293GPG as described (Proc. Natl. Acad. Sci. USA 93:11400-11406 (1996)). To obtain a polyclonal population of cells in which the majority of cells inducibly expressed N-CoR2 or its mutant these transduced cells were first expanded in the presence of tetracycline at 1 µg/mL and then N-CoR2 expression was induced by withdrawal of tetracycline for 2 to 4 days, followed by FAC sorting for EGFP positive cells. Sorted cells were expanded again in the presence of tetracycline. As the overexpressed N-CoR2 protein underwent gradual degradation in monolayer cultures, we did not activate the tetracycline-regulated expression of N-CoR2 in HMT3522 T4-2 cells until being cultured in reconstituted basement membrane.

To profile the gene expressions of HMT3522 T4-2 cells that stably expressed N-CoR2 or an empty vector, the cells were grown in a reconstituted basement membrane (rBM) culture according to the procedures described in U.S. Pat. No. 6,123,941 and Nat. Method. 4:359-365 (2007). rBM is a specific 3D culture matrix isolated from mouse Englebreth-Holm-Swarm (EHS) tumors (commercially available as Matrigel, BD Biosciences) and is made of about 80% laminin, about 10% type IV collagen, about 10% proteoglycans and growth factors. To increase the yield of RNA for transcriptional profiling experiments, we grew $2 \times 10^5$ cells on top of rBM in a 60-mm tissue culture dish. As described, cells grown on top of rBM formed 3D cellular aggregates similar to those embedded in rBM. Four replicate cultures were established for each of the 2 experiment groups, including those using HMT3522 T4-2 cells that stably expressed N-CoR2 (T4-2 N-CoR2 cells) and those expressing the empty vector (T4-2 vector cells). The cultures were maintained for 6 days before the collection of RNA samples.

Total RNA was extracted from monolayer culture or 3D culture by a modified TR1 reagent procedure as described (Biotechniques 19:942-945 (1995)) and purified using an RNeasy Mini Kit (Qiagen). Gene expression analysis was performed on an Affymetrix Human Genome U133A 2.0 GeneChip platform containing 22,283 probes according to the manufacturer's protocol (Affymetrix). Twenty micrograms of total RNA from each sample was processed to produce biotinylated cRNA targets. After hybridization, washing and staining arrays were scanned using a confocal scanner (Affymetrix). The hybridization intensity data was processed using the GeneChip Operating software (Affymetrix). Affymetrix .cel files (probe intensity files) were processed with ArrayAssist Lite (v3.4, Stratagene). The files were imported and processed with the GC-RMA algorithm to yield probe set intensities and additionally, Affymetrix Preset, Absent, Marginal flags were computed. These values were exported in .chp files, which were subsequently imported into the Partek Genomics Suite software (v6.2, Partek). The genes were filtered based on the Affymetrix P/A/M flags to retain only those genes that were present in at least 2 of the 8 samples.

To select genes in HMT3522 T4-2 cells that are differentially induced or repressed upon overexpression of N-CoR2, the GC-RMA expression values of all the 8 transcriptomes were log 2 transformed and pairwise contrasts were performed using Student's t test.

A list of 304 genes (represented by 350 Affymetrix probe sets) were identified from the microarray experiments based on their expression levels significantly different (fold change $\geq 2$ and a cutoff P-value <0.05 by Student's t test) between T4-2-N-CoR2 cells and the vector control cells. These genes are hereinafter designated as "NCOR2-350". Functional annotations of NCOR2-350 suggested that N-CoR2 mainly regulated the transcription of genes involved in extracellular matrix assembly and remodeling (e.g., FN1, SDC2, TIMP3, MMP1, COL4A1, THBS1, TAGLN, TNC, COL6A2, ITGA6, ITGB4), inflammation (e.g., IL6, TREM1, C3AR1, FOS, MAPK1, CXCL3, CXCL10), growth and differentiation (e.g., SFRP1, TGFA, CCNG2, CNAP1, EGFR, NOTCH2, NRG1, EREG), and cytoskeleton and cell-cell adhesion (e.g., TPX2, SPOCK1, ARHGAP1, PAK1, WASL, DSC2, DSG3). Table 1 provides a detailed list of the 304 genes that were differentially expressed in response to N-CoR2 overexpression in HMT3522 T4-2 cells. The genes (probe sets) are ranked in descending order according to the ratio between the mean hybridization intensity of each probe in T4-2 vector cells (V) and that in T4-2 N-CoR2 cells (N).

TABLE 1

The 304 genes (350 Affymetrix probe sets or NCOR2-350) that are differentially expressed in response to N-CoR2 overexpression in HMT3522 T4-2 cells.

| AFFYMETRIX PROBE SET ID | GENE SYMBOL | REFSEQ TRANSCRIPT ID | MEAN INTENSITY (V) | MEAN INTENSITY (N) | RATIO (V/N) |
|---|---|---|---|---|---|
| 210119_at | KCNJ15 | NM_002243/ NM_170736/ NM_170737 | 136.33 | 11.06 | 12.33 |
| 211806_s_at | KCNJ15 | NM_002243/ NM_170736/ NM_170737 | 43.15 | 4.82 | 8.94 |
| 211719_x_at | FN1 | NM_002026/ NM_054034/ NM_212474/ NM_212475/ NM_212476/ NM_212478/ NM_212482 | 7290.69 | 1237.54 | 5.89 |
| 216442_x_at | FN1 | NM_002026/ NM_054034/ NM_212474/ NM_212475/ NM_212476/ NM_212478/ NM_212482 | 4490.64 | 781.95 | 5.74 |
| 214701_s_at | FN1 | NM_002026/ NM_054034/ NM_212474/ NM_212475/ NM_212476/ NM_212478/ NM_212482 | 34.32 | 6.00 | 5.72 |
| 210495_x_at | FN1 | NM_002026/ NM_054034/ NM_212474/ NM_212475/ NM_212476/ NM_212478/ NM_212482 | 4478.15 | 790.08 | 5.67 |
| 205207_at | IL6 | NM_000600 | 421.76 | 79.36 | 5.31 |
| 212464_s_at | FN1 | NM_002026/ NM_054034/ NM_212474/ NM_212475/ NM_212476/ NM_212478/ NM_212482 | 3877.24 | 730.91 | 5.30 |
| 214336_s_at | COPA | NM_004371 | 41.88 | 7.94 | 5.27 |
| 219434_at | TREM1 | NM_018643 | 275.64 | 54.65 | 5.04 |
| 212154_at | SDC2 | NM_002998 | 517.35 | 117.88 | 4.39 |
| 211981_at | COL4A1 | NM_001845 | 55.16 | 13.20 | 4.18 |
| 217859_s_at | SLC39A9 | NM_018375 | 80.47 | 21.36 | 3.77 |
| 201107_s_at | THBS1 | NM_003246 | 411.89 | 112.11 | 3.67 |
| 206184_at | CRKL | NM_005207 | 26.61 | 7.52 | 3.54 |
| 212158_at | SDC2 | NM_002998 | 88.69 | 25.07 | 3.54 |
| 209136_s_at | USP10 | NM_005153 | 111.34 | 32.25 | 3.45 |
| 205547_s_at | TAGLN | NM_001001522/ NM_003186 | 187.92 | 54.58 | 3.44 |
| 203925_at | GCLM | NM_002061 | 469.78 | 136.88 | 3.43 |
| 200879_s_at | EPAS1 | NM_001430 | 272.67 | 79.80 | 3.42 |
| 202037_s_at | SFRP1 | NM_003012 | 81.81 | 24.36 | 3.36 |
| 201150_s_at | TIMP3 | NM_000362 | 64.52 | 19.75 | 3.27 |
| 212142_at | MCM4 | NM_005914/ NM_182746 | 32.67 | 10.00 | 3.27 |
| 211559_s_at | CCNG2 | NM_004354 | 16.67 | 5.11 | 3.26 |
| 209456_s_at | FBXW11 | NM_012300/ NM_033644/ NM_033645 | 66.57 | 20.42 | 3.26 |
| 210735_s_at | CA12 | NM_001218/ NM_206925 | 190.16 | 58.46 | 3.25 |
| 210052_s_at | TPX2 | NM_012112 | 691.71 | 216.33 | 3.20 |
| 204764_at | FNTB | NM_002028 | 95.95 | 30.47 | 3.15 |
| 209906_at | C3AR1 | NM_004054 | 23.28 | 7.46 | 3.12 |
| 201774_s_at | CNAP1 | NM_014865 | 467.66 | 149.85 | 3.12 |
| 211966_at | COL4A2 | NM_001846 | 52.83 | 17.44 | 3.03 |
| 201147_s_at | TIMP3 | NM_000362 | 43.90 | 14.52 | 3.02 |
| 201830_s_at | NET1 | NM_005863 | 122.64 | 40.69 | 3.01 |

TABLE 1-continued

The 304 genes (350 Affymetrix probe sets or NCOR2-350) that are differentially expressed in response to N-CoR2 overexpression in HMT3522 T4-2 cells.

| AFFYMETRIX PROBE SET ID | GENE SYMBOL | REFSEQ TRANSCRIPT ID | MEAN INTENSITY (V) | MEAN INTENSITY (N) | RATIO (V/N) |
|---|---|---|---|---|---|
| 206363_at | MAF | NM_001031804/ NM_005360 | 415.48 | 137.94 | 3.01 |
| 209401_s_at | SLC12A4 | NM_005072 | 53.10 | 17.66 | 3.01 |
| 204475_at | MMP1 | NM_002421 | 192.36 | 64.09 | 3.00 |
| 217445_s_at | GART | NM_000819/ NM_175085 | 224.08 | 75.91 | 2.95 |
| 208853_s_at | CANX | NM_001024649/ NM_001746 | 237.89 | 81.66 | 2.91 |
| 211519_s_at | KIF2C | NM_006845 | 97.80 | 33.68 | 2.90 |
| 211964_at | COL4A2 | NM_001846 | 486.47 | 167.64 | 2.90 |
| 219213_at | JAM2 | NM_021219 | 15.53 | 5.45 | 2.85 |
| 211607_x_at | EGFR | NM_005228/ NM_201282/ NM_201283/ NM_201284 | 463.55 | 163.46 | 2.84 |
| 210984_x_at | EGFR | NM_005228/ NM_201282/ NM_201283/ NM_201284 | 475.74 | 170.80 | 2.79 |
| 210756_s_at | NOTCH2 | NM_024408 | 328.26 | 118.38 | 2.77 |
| 203798_s_at | VSNL1 | NM_003385 | 90.05 | 32.73 | 2.75 |
| 209189_at | FOS | NM_005252 | 1156.59 | 420.66 | 2.75 |
| 210892_s_at | GTF2I | NM_001518/ NM_032999/ NM_033000/ NM_033001 | 95.29 | 34.75 | 2.74 |
| 205729_at | OSMR | NM_003999 | 89.57 | 32.83 | 2.73 |
| 203967_at | CDC6 | NM_001254 | 14.73 | 5.41 | 2.72 |
| 202240_at | PLK1 | NM_005030 | 367.26 | 134.92 | 2.72 |
| 221530_s_at | BHLHB3 | NM_030762 | 66.58 | 24.51 | 2.72 |
| 211249_at | GPR68 | NM_003485 | 16.79 | 6.20 | 2.71 |
| 202363_at | SPOCK1 | NM_004598 | 55.22 | 20.40 | 2.71 |
| 218115_at | ASF1B | NM_018154 | 123.19 | 45.68 | 2.70 |
| 212022_s_at | MKI67 | NM_002417 | 383.86 | 143.95 | 2.67 |
| 211980_at | COL4A1 | NM_001845 | 550.91 | 206.88 | 2.66 |
| 212190_at | SERPINE2 | NM_006216 | 668.64 | 252.62 | 2.65 |
| 202444_s_at | SPFH1 | NM_006459 | 102.12 | 38.60 | 2.65 |
| 208351_s_at | MAPK1 | NM_002745/ NM_138957 | 92.19 | 35.08 | 2.63 |
| 201755_at | MCM5 | NM_006739 | 93.87 | 36.11 | 2.60 |
| 221901_at | KIAA1644 | XM_376018/ XM_936510 | 111.78 | 43.02 | 2.60 |
| 204318_s_at | GTSE1 | NM_016426 | 114.61 | 44.39 | 2.58 |
| 52837_at | KIAA1644 | XM_376018/ XM_936510 | 69.64 | 27.20 | 2.56 |
| 209098_s_at | JAG1 | NM_000214 | 212.90 | 83.59 | 2.55 |
| 209347_s_at | MAF | NM_001031804/ NM_005360 | 24.86 | 9.79 | 2.54 |
| 204879_at | PDPN | NM_001006624/ NM_001006625/ NM_006474/ NM_198389 | 329.72 | 129.96 | 2.54 |
| 207357_s_at | GALNT10 | NM_017540/ NM_198321 | 212.98 | 84.03 | 2.53 |
| 208852_s_at | CANX | NM_001024649/ NM_001746 | 333.80 | 131.78 | 2.53 |
| 40837_at | TLE2 | NM_003260 | 107.13 | 42.69 | 2.51 |
| 221520_s_at | CDCA8 | NM_018101 | 200.88 | 80.78 | 2.49 |
| 205015_s_at | TGFA | NM_003236 | 34.75 | 14.02 | 2.48 |
| 210543_s_at | PRKDC | NM_006904 | 157.63 | 63.61 | 2.48 |
| 219093_at | FLJ20701 | NM_017933 | 403.42 | 162.82 | 2.48 |
| 209758_s_at | MFAP5 | NM_003480 | 44.75 | 18.23 | 2.45 |
| 204962_s_at | CENPA | NM_001809 | 219.28 | 90.09 | 2.43 |
| 210082_at | ABCA4 | NM_000350 | 11.46 | 4.77 | 2.40 |
| 214686_at | ZNF266 | NM_006631/ NM_198058 | 17.77 | 7.41 | 2.40 |
| 206429_at | F2RL1 | NM_005242 | 38.12 | 16.02 | 2.38 |
| 210105_s_at | FYN | NM_002037/ NM_153047/ NM_153048 | 35.10 | 14.78 | 2.37 |
| 218073_s_at | TMEM48 | NM_018087 | 76.98 | 33.03 | 2.33 |
| 218365_s_at | DARS2 | NM_018122 | 56.42 | 24.32 | 2.32 |
| 204147_s_at | TFDP1 | NM_007111 | 108.10 | 46.74 | 2.31 |

TABLE 1-continued

The 304 genes (350 Affymetrix probe sets or NCOR2-350) that are differentially expressed in response to N-CoR2 overexpression in HMT3522 T4-2 cells.

| AFFYMETRIX PROBE SET ID | GENE SYMBOL | REFSEQ TRANSCRIPT ID | MEAN INTENSITY (V) | MEAN INTENSITY (N) | RATIO (V/N) |
|---|---|---|---|---|---|
| 218717_s_at | LEPREL1 | NM_018192 | 196.30 | 85.17 | 2.30 |
| 212372_at | MYH10 | NM_005964 | 80.32 | 34.96 | 2.30 |
| 202954_at | UBE2C | NM_007019/ NM_181799/ NM_181800/ NM_181801/ NM_181802/ NM_181803 | 3038.31 | 1325.26 | 2.29 |
| 221004_s_at | ITM2C | NM_001012514/ NM_001012516/ NM_030926 | 96.07 | 42.05 | 2.28 |
| 217010_s_at | CDC25C | NM_001790/ NM_022809 | 15.92 | 6.98 | 2.28 |
| 209408_at | KIF2C | NM_006845 | 270.75 | 119.13 | 2.27 |
| 216033_s_at | FYN | NM_002037/ NM_153047/ NM_153048 | 11.66 | 5.15 | 2.27 |
| 202779_s_at | UBE2S | NM_014501/ XM_941060 | 2736.53 | 1214.09 | 2.25 |
| 207850_at | CXCL3 | NM_002090 | 106.06 | 47.22 | 2.25 |
| 215253_s_at | DSCR1 | NM_004414/ NM_203417/ NM_203418 | 25.11 | 11.19 | 2.24 |
| 201645_at | TNC | NM_002160 | 304.33 | 136.18 | 2.23 |
| 215942_s_at | GTSE1 | NM_016426 | 36.42 | 16.31 | 2.23 |
| 202479_s_at | TRIB2 | NM_021643 | 77.65 | 34.81 | 2.23 |
| 204033_at | TRIP13 | NM_004237 | 286.45 | 128.65 | 2.23 |
| 202870_s_at | CDC20 | NM_001255 | 2583.94 | 1160.70 | 2.23 |
| 219928_s_at | CABYR | NM_012189/ NM_138643/ NM_138644/ NM_153768/ NM_153769/ NM_153770 | 58.24 | 26.32 | 2.21 |
| 217080_s_at | HOMER2 | NM_004839/ NM_199330/ NM_199331/ NM_199332 | 107.14 | 48.48 | 2.21 |
| 212016_s_at | PTBP1 | NM_002819/ NM_031990/ NM_031991/ NM_175847 | 763.83 | 348.48 | 2.19 |
| 209156_s_at | COL6A2 | NM_001849/ NM_058174/ NM_058175 | 12.80 | 5.88 | 2.18 |
| 211194_s_at | TP73L | NM_003722 | 65.03 | 29.89 | 2.18 |
| 200641_s_at | YWHAZ | NM_003406/ NM_145690 | 1891.11 | 870.58 | 2.17 |
| 201529_s_at | RPA1 | NM_002945 | 112.68 | 51.92 | 2.17 |
| 217173_s_at | LDLR | NM_000527 | 332.27 | 153.20 | 2.17 |
| 215177_s_at | ITGA6 | NM_000210 | 806.65 | 372.47 | 2.17 |
| 204768_s_at | FEN1 | NM_004111 | 205.73 | 95.00 | 2.17 |
| 218755_at | KIF20A | NM_005733 | 341.77 | 158.10 | 2.16 |
| 203865_s_at | ADARB1 | NM_001033049/ NM_001112/ NM_015833/ NM_015834 | 177.68 | 82.32 | 2.16 |
| 209395_at | CHI3L1 | NM_001276 | 145.15 | 67.32 | 2.16 |
| 212021_s_at | MKI67 | NM_002417 | 181.65 | 84.26 | 2.16 |
| 203676_at | GNS | NM_002076 | 15.58 | 7.23 | 2.15 |
| 213562_s_at | SQLE | NM_003129 | 492.91 | 229.04 | 2.15 |
| 209645_s_at | ALDH1B1 | NM_000692 | 116.91 | 54.64 | 2.14 |
| 216969_s_at | KIF22 | NM_007317 | 158.72 | 74.29 | 2.14 |
| 209278_s_at | TFPI2 | NM_006528 | 50.76 | 23.81 | 2.13 |
| 214536_at | SLURP1 | NM_020427 | 38.09 | 17.87 | 2.13 |
| 202718_at | IGFBP2 | NM_000597 | 201.29 | 94.69 | 2.13 |
| 221436_s_at | CDCA3 | NM_031299 | 195.39 | 91.95 | 2.12 |
| 209896_s_at | PTPN11 | NM_002834 | 17.55 | 8.26 | 2.12 |
| 208782_at | FSTL1 | NM_007085 | 210.15 | 98.97 | 2.12 |
| 215357_s_at | POLDIP3 | NM_032311/ NM_178136 | 116.88 | 55.07 | 2.12 |

TABLE 1-continued

The 304 genes (350 Affymetrix probe sets or NCOR2-350) that are differentially expressed in response to N-CoR2 overexpression in HMT3522 T4-2 cells.

| AFFYMETRIX PROBE SET ID | GENE SYMBOL | REFSEQ TRANSCRIPT ID | MEAN INTENSITY (V) | MEAN INTENSITY (N) | RATIO (V/N) |
|---|---|---|---|---|---|
| 217202_s_at | GLUL | NM_001033044/ NM_001033056/ NM_002065 | 79.13 | 37.34 | 2.12 |
| 200900_s_at | M6PR | NM_002355 | 316.05 | 149.12 | 2.12 |
| 204589_at | NUAK1 | NM_014840 | 194.88 | 92.30 | 2.11 |
| 218009_s_at | PRC1 | NM_003981/ NM_199413/ NM_199414 | 337.52 | 159.87 | 2.11 |
| 201984_s_at | EGFR | NM_005228/ NM_201282/ NM_201283/ NM_201284 | 2124.37 | 1007.51 | 2.11 |
| 210935_s_at | WDR1 | NM_005112/ NM_017491 | 559.44 | 265.33 | 2.11 |
| 211905_s_at | ITGB4 | NM_000213/ NM_001005619/ NM_001005731 | 1052.93 | 500.01 | 2.11 |
| 216689_x_at | ARHGAP1 | NM_004308 | 222.84 | 106.03 | 2.10 |
| 201801_s_at | SLC29A1 | NM_004955 | 64.64 | 30.82 | 2.10 |
| 203145_at | SPAG5 | NM_006461 | 99.59 | 47.51 | 2.10 |
| 214710_s_at | CCNB1 | NM_031966 | 1404.09 | 670.35 | 2.09 |
| 209615_s_at | PAK1 | NM_002576 | 78.62 | 37.63 | 2.09 |
| 218726_at | DKFZp762E1312 | NM_018410 | 60.36 | 28.91 | 2.09 |
| 211804_s_at | CDK2 | NM_001798/ NM_052827 | 103.89 | 50.00 | 2.08 |
| 203976_s_at | CHAF1A | NM_005483 | 38.07 | 18.35 | 2.07 |
| 211162_x_at | SCD | NM_005063 | 1184.84 | 572.31 | 2.07 |
| 58916_at | KCTD14 | NM_023930 | 28.95 | 14.00 | 2.07 |
| 218308_at | TACC3 | NM_006342 | 202.69 | 98.40 | 2.06 |
| 200796_s_at | MCL1 | NM_021960/ NM_182763 | 34.79 | 16.94 | 2.05 |
| 209624_s_at | MCCC2 | NM_022132 | 26.63 | 13.00 | 2.05 |
| 209396_s_at | CHI3L1 | NM_001276 | 100.75 | 49.24 | 2.05 |
| 212614_at | ARID5B | NM_032199 | 18.89 | 9.26 | 2.04 |
| 204140_at | TPST1 | NM_003596 | 164.97 | 80.90 | 2.04 |
| 215739_s_at | TUBGCP3 | NM_006322 | 94.67 | 46.43 | 2.04 |
| 201555_at | MCM3 | NM_002388 | 304.81 | 149.69 | 2.04 |
| 204508_s_at | CA12 | NM_001218/ NM_206925 | 121.17 | 59.66 | 2.03 |
| 210301_at | XDH | NM_000379 | 245.51 | 120.99 | 2.03 |
| 207821_s_at | PTK2 | NM_005607/ NM_153831 | 283.60 | 140.15 | 2.02 |
| 200644_at | MARCKSL1 | NM_023009 | 166.24 | 82.36 | 2.02 |
| 212949_at | BRRN1 | NM_015341 | 28.66 | 14.21 | 2.02 |
| 202095_s_at | BIRC5 | NM_001012270/ NM_001012271/ NM_001168 | 473.20 | 235.27 | 2.01 |
| 202058_s_at | KPNA1 | NM_002264 | 187.66 | 93.38 | 2.01 |
| 221029_s_at | WNT5B | NM_030775/ NM_032642 | 47.71 | 23.74 | 2.01 |
| 203963_at | CA12 | NM_001218/ NM_206925 | 1086.47 | 540.99 | 2.01 |
| 208539_x_at | SPRR2B | NM_001017418 | 5343.04 | 2670.07 | 2.00 |
| 207655_s_at | BLNK | NM_013314 | 122.03 | 244.59 | 0.50 |
| 209533_s_at | PLAA | NM_001031689/ NM_004253 | 63.38 | 127.13 | 0.50 |
| 202219_at | SLC6A8 | NM_005629 | 356.75 | 718.43 | 0.50 |
| 213510_x_at | LOC220594 | NM_145809 | 12.83 | 25.89 | 0.50 |
| 221568_s_at | LIN7C | NM_018362 | 21.41 | 43.29 | 0.49 |
| 213082_s_at | SLC35D2 | NM_007001 | 79.26 | 160.33 | 0.49 |
| 210580_x_at | SULT1A3 | NM_001017387/ NM_001017389/ NM_001017390/ NM_001017391/ NM_003166/ NM_177552 | 53.48 | 108.19 | 0.49 |
| 205660_at | OASL | NM_003733/ NM_198213 | 193.82 | 393.43 | 0.49 |
| 202357_s_at | CFB | NM_001710 | 94.01 | 191.29 | 0.49 |
| 212989_at | TMEM23 | NM_147156 | 40.03 | 81.72 | 0.49 |
| 204686_at | IRS1 | NM_005544 | 118.07 | 241.06 | 0.49 |
| 214329_x_at | TNFSF10 | NM_003810 | 44.20 | 90.28 | 0.49 |
| 209422_at | PHF20 | NM_016436 | 77.62 | 158.60 | 0.49 |

TABLE 1-continued

The 304 genes (350 Affymetrix probe sets or NCOR2-350) that are differentially expressed in response to N-CoR2 overexpression in HMT3522 T4-2 cells.

| AFFYMETRIX PROBE SET ID | GENE SYMBOL | REFSEQ TRANSCRIPT ID | MEAN INTENSITY (V) | MEAN INTENSITY (N) | RATIO (V/N) |
|---|---|---|---|---|---|
| 202869_at | OAS1 | NM_001032409/ NM_002534/ NM_016816 | 126.11 | 258.43 | 0.49 |
| 218446_s_at | FAM18B | NM_016078 | 47.24 | 96.87 | 0.49 |
| 219424_at | EBI3 | NM_005755 | 19.66 | 40.35 | 0.49 |
| 208841_s_at | G3BP2 | NM_012297/ NM_203504/ NM_203505 | 81.38 | 167.15 | 0.49 |
| 204454_at | LDOC1 | NM_012317 | 953.41 | 1959.60 | 0.49 |
| 203909_at | SLC9A6 | NM_006359 | 35.79 | 73.82 | 0.48 |
| 222158_s_at | C1orf121 | NM_016076 | 14.79 | 30.54 | 0.48 |
| 208801_at | SRP72 | NM_006947 | 57.96 | 119.73 | 0.48 |
| 49452_at | ACACB | NM_001093 | 29.49 | 60.95 | 0.48 |
| 200994_at | IPO7 | NM_006391 | 39.24 | 81.14 | 0.48 |
| 203247_s_at | ZNF24 | NM_006965 | 12.43 | 25.73 | 0.48 |
| 203446_s_at | OCRL | NM_000276/ NM_001587 | 51.08 | 105.81 | 0.48 |
| 201828_x_at | CXX1 | NM_003928 | 1810.05 | 3750.20 | 0.48 |
| 219503_s_at | TMEM40 | NM_018306 | 20.04 | 41.54 | 0.48 |
| 219628_at | WIG1 | NM_022470/ NM_152240 | 26.58 | 55.17 | 0.48 |
| 218042_at | COPS4 | NM_016129 | 19.22 | 39.94 | 0.48 |
| 202854_at | HPRT1 | NM_000194 | 409.07 | 851.08 | 0.48 |
| 209565_at | RNF113A | NM_006978 | 158.91 | 330.99 | 0.48 |
| 201904_s_at | CTDSPL | NM_001008392/ NM_005808 | 167.47 | 349.18 | 0.48 |
| 205483_s_at | ISG15 | NM_005101 | 469.58 | 979.50 | 0.48 |
| 204897_at | PTGER4 | NM_000958 | 15.27 | 31.87 | 0.48 |
| 204014_at | DUSP4 | NM_001394/ NM_057158 | 78.05 | 162.95 | 0.48 |
| 221514_at | UTP14A | NM_006649 | 156.08 | 326.84 | 0.48 |
| 203007_x_at | LYPLA1 | NM_006330 | 48.47 | 101.55 | 0.48 |
| 213883_s_at | TM2D1 | NM_032027 | 46.96 | 98.40 | 0.48 |
| 201921_at | GNG10 | NM_001017998/ NM_004125/ XM_929619/ XM_940579 | 368.56 | 775.54 | 0.48 |
| 207847_s_at | MUC1 | NM_001018016/ NM_001018017/ NM_001018021/ NM_002456 | 41.04 | 86.42 | 0.47 |
| 203108_at | GPRC5A | NM_003979 | 208.08 | 438.12 | 0.47 |
| 213587_s_at | ATP6V0E2L | NM_145230 | 25.27 | 53.41 | 0.47 |
| 218952_at | PCSK1N | NM_013271 | 169.94 | 359.28 | 0.47 |
| 221931_s_at | SEH1L | NM_001013437/ NM_031216 | 43.80 | 92.68 | 0.47 |
| 221989_at | RPL10 | NM_006013/ XM_209178/ XM_209500/ XM_371781/ XM_497357/ XM_926723/ XM_929431/ XM_930080/ XM_931512/ XM_931519/ XM_931525/ XM_931532/ XM_931535/ XM_934704/ XM_934705/ XM_934706/ XM_937850/ XM_939745/ XM_941543/ XM_941661/ XM_942217/ XM_944311/ XM_944319/ XM_944324/ XM_945797/ XM_945798/ | 4.90 | 10.38 | 0.47 |

TABLE 1-continued

The 304 genes (350 Affymetrix probe sets or NCOR2-350) that are differentially expressed in response to N-CoR2 overexpression in HMT3522 T4-2 cells.

| AFFYMETRIX PROBE SET ID | GENE SYMBOL | REFSEQ TRANSCRIPT ID | MEAN INTENSITY (V) | MEAN INTENSITY (N) | RATIO (V/N) |
|---|---|---|---|---|---|
| | | XM_945799/ XM_945800 | | | |
| 205145_s_at | MYL5 | NM_002477/ XM_938923 | 12.55 | 26.56 | 0.47 |
| 201238_s_at | CAPZA2 | NM_006136 | 89.77 | 191.02 | 0.47 |
| 210645_s_at | TTC3 | NM_001001894/ NM_003316 | 24.14 | 51.41 | 0.47 |
| 210136_at | MBP | NM_001025081/ NM_001025090/ NM_001025092/ NM_001025094/ NM_001025098/ NM_001025100/ NM_001025101/ NM_002385 | 8.49 | 18.08 | 0.47 |
| 201358_s_at | COPB | NM_016451 | 142.12 | 304.25 | 0.47 |
| 210511_s_at | INHBA | NM_002192 | 129.36 | 276.98 | 0.47 |
| 201888_s_at | IL13RA1 | NM_001560 | 23.61 | 50.66 | 0.47 |
| 209115_at | UBE1C | NM_003968/ NM_198195/ NM_198197 | 27.53 | 59.10 | 0.47 |
| 217739_s_at | PBEF1 | NM_005746/ NM_182790/ XM_929247 | 30.38 | 65.23 | 0.47 |
| 213361_at | TDRD7 | NM_014290 | 8.68 | 18.65 | 0.47 |
| 210663_s_at | KYNU | NM_001032998/ NM_003937 | 104.25 | 224.59 | 0.46 |
| 204698_at | ISG20 | NM_002201 | 383.20 | 826.64 | 0.46 |
| 204415_at | IFI6 | NM_002038/ NM_022872/ NM_022873 | 34.19 | 73.79 | 0.46 |
| 218053_at | PRPF40A | XM_371575/ XM_931099/ XM_938514/ XM_943711 | 61.31 | 132.43 | 0.46 |
| 207719_x_at | CEP170 | NM_014812 | 10.04 | 21.69 | 0.46 |
| 206295_at | IL18 | NM_001562 | 86.99 | 188.27 | 0.46 |
| 33304_at | ISG20 | NM_002201 | 222.58 | 482.12 | 0.46 |
| 214112_s_at | CXorf40A | NM_001013845/ NM_178124 | 219.43 | 479.14 | 0.46 |
| 205315_s_at | SNTB2 | NM_006750/ NM_130845 | 40.07 | 87.78 | 0.46 |
| 217948_at | — | — | 322.08 | 706.40 | 0.46 |
| 214022_s_at | IFITM1 | NM_003641 | 1869.34 | 4135.74 | 0.45 |
| 211122_s_at | CXCL11 | NM_005409 | 5.81 | 12.87 | 0.45 |
| 212510_at | GPD1L | NM_015141 | 10.17 | 22.53 | 0.45 |
| 205595_at | DSG3 | NM_001944 | 80.07 | 177.64 | 0.45 |
| 202923_s_at | GCLC | NM_001498 | 75.00 | 167.13 | 0.45 |
| 202169_s_at | AASDHPPT | NM_015423 | 11.33 | 25.30 | 0.45 |
| 202351_at | ITGAV | NM_002210 | 228.62 | 510.51 | 0.45 |
| 219356_s_at | CHMP5 | NM_016410 | 108.75 | 242.88 | 0.45 |
| 201864_at | GDI1 | NM_001493 | 160.21 | 358.31 | 0.45 |
| 222266_at | C19orf2 | NM_003796/ NM_134447 | 11.46 | 25.69 | 0.45 |
| 204020_at | PURA | NM_005859 | 89.35 | 200.32 | 0.45 |
| 218086_at | NPDC1 | NM_015392 | 147.25 | 330.55 | 0.45 |
| 209028_s_at | ABI1 | NM_001012750/ NM_001012751/ NM_001012752/ NM_005470 | 48.80 | 109.59 | 0.45 |
| 218237_s_at | SLC38A1 | NM_030674 | 269.77 | 608.07 | 0.44 |
| 202437_s_at | CYP1B1 | NM_000104 | 27.81 | 62.70 | 0.44 |
| 213016_at | — | — | 15.13 | 34.12 | 0.44 |
| 201996_s_at | SPEN | NM_015001 | 32.11 | 72.47 | 0.44 |
| 217388_s_at | KYNU | NM_001032998/ NM_003937 | 280.28 | 634.02 | 0.44 |
| 212640_at | PTPLB | NM_198402 | 202.85 | 459.88 | 0.44 |
| 219010_at | C1orf106 | NM_018265 | 257.64 | 585.64 | 0.44 |
| 219351_at | TRAPPC2 | NM_001011658/ NM_014563 | 31.50 | 71.62 | 0.44 |
| 213083_at | SLC35D2 | NM_007001 | 103.19 | 234.84 | 0.44 |
| 218163_at | MCTS1 | NM_014060 | 228.29 | 521.74 | 0.44 |
| 207941_s_at | RNPC2 | NM_004902/ | 34.40 | 78.71 | 0.44 |

TABLE 1-continued

The 304 genes (350 Affymetrix probe sets or NCOR2-350) that are differentially expressed in response to N-CoR2 overexpression in HMT3522 T4-2 cells.

| AFFYMETRIX PROBE SET ID | GENE SYMBOL | REFSEQ TRANSCRIPT ID | MEAN INTENSITY (V) | MEAN INTENSITY (N) | RATIO (V/N) |
|---|---|---|---|---|---|
| | | NM_184234/ NM_184237/ NM_184241/ NM_184244 | | | |
| 214722_at | NOTCH2NL | NM_203458 | 69.57 | 159.38 | 0.44 |
| 209726_at | CA11 | NM_001217 | 45.82 | 105.08 | 0.44 |
| 203917_at | CXADR | NM_001338 | 31.01 | 71.25 | 0.44 |
| 38043_at | FAM3A | NM_021806 | 29.77 | 68.61 | 0.43 |
| 218986_s_at | FLJ20035 | NM_017631 | 12.73 | 29.34 | 0.43 |
| 222242_s_at | KLK5 | NM_012427 | 11.35 | 26.38 | 0.43 |
| 53991_at | DENND2A | NM_015689 | 8.82 | 20.60 | 0.43 |
| 209289_at | NFIB | NM_005596 | 27.75 | 64.90 | 0.43 |
| 201540_at | FHL1 | NM_001449 | 451.06 | 1059.88 | 0.43 |
| 204097_s_at | RBMX2 | NM_016024 | 9.32 | 21.99 | 0.42 |
| 202602_s_at | HTATSF1 | NM_014500 | 33.73 | 79.70 | 0.42 |
| 204981_at | SLC22A18 | NM_002555/ NM_183233 | 86.64 | 205.14 | 0.42 |
| 200696_s_at | GSN | NM_000177/ NM_198252 | 385.91 | 914.82 | 0.42 |
| 221841_s_at | KLF4 | NM_004235 | 111.47 | 264.55 | 0.42 |
| 205709_s_at | CDS1 | NM_001263 | 18.03 | 42.93 | 0.42 |
| 216942_s_at | CD58 | NM_001779 | 14.54 | 34.65 | 0.42 |
| 213294_at | — | — | 7.66 | 18.29 | 0.42 |
| 212415_at | SEPT6 | NM_015129/ NM_145799/ NM_145800/ NM_145802 | 4.62 | 11.03 | 0.42 |
| 212616_at | CHD9 | NM_025134 | 7.23 | 17.34 | 0.42 |
| 217947_at | CMTM6 | NM_017801 | 206.54 | 498.31 | 0.41 |
| 211612_s_at | IL13RA1 | NM_001560 | 43.45 | 104.96 | 0.41 |
| 212531_at | LCN2 | NM_005564 | 174.02 | 420.45 | 0.41 |
| 201661_s_at | ACSL3 | NM_004457/ NM_203372 | 10.17 | 24.61 | 0.41 |
| 213729_at | PRPF40A | XM_371575/ XM_931099/ XM_938514/ XM_943711 | 6.42 | 15.54 | 0.41 |
| 205220_at | GPR109B | NM_006018 | 266.95 | 645.95 | 0.41 |
| 203186_s_at | S100A4 | NM_002961/ NM_019554 | 94.02 | 227.62 | 0.41 |
| 203821_at | HBEGF | NM_001945 | 403.66 | 977.38 | 0.41 |
| 221766_s_at | FAM46A | NM_017633 | 10.35 | 25.10 | 0.41 |
| 215813_s_at | PTGS1 | NM_000962/ NM_080591 | 31.23 | 76.88 | 0.41 |
| 202277_at | SPTLC1 | NM_006415/ NM_178324 | 44.77 | 110.99 | 0.40 |
| 202829_s_at | SYBL1 | NM_005638 | 15.37 | 38.13 | 0.40 |
| 201887_at | IL13RA1 | NM_001560 | 37.84 | 93.97 | 0.40 |
| 216095_x_at | MTMR1 | NM_003828 | 128.02 | 318.26 | 0.40 |
| 217813_s_at | SPIN | NM_006717 | 23.85 | 59.32 | 0.40 |
| 205428_s_at | CALB2 | NM_001740/ NM_007087/ NM_007088 | 57.31 | 143.13 | 0.40 |
| 204343_at | ABCA3 | NM_001089 | 15.33 | 38.38 | 0.40 |
| 38037_at | HBEGF | NM_001945 | 144.05 | 361.24 | 0.40 |
| 209194_at | CETN2 | NM_004344 | 74.08 | 187.44 | 0.40 |
| 202371_at | TCEAL4 | NM_001006935/ NM_001006936/ NM_001006937/ NM_024863 | 105.84 | 269.43 | 0.39 |
| 206645_s_at | NR0B1 | NM_000475 | 42.07 | 107.59 | 0.39 |
| 221829_s_at | TNPO1 | NM_002270/ NM_153188 | 83.30 | 213.54 | 0.39 |
| 219045_at | RHOF | NM_019034 | 210.67 | 540.25 | 0.39 |
| 211343_s_at | COL13A1 | NM_005203/ NM_080798/ NM_080799/ NM_080800/ NM_080801/ NM_080802/ NM_080803/ NM_080804/ NM_080805/ | 34.51 | 88.75 | 0.39 |

TABLE 1-continued

The 304 genes (350 Affymetrix probe sets or NCOR2-350) that are differentially expressed in response to N-CoR2 overexpression in HMT3522 T4-2 cells.

| AFFYMETRIX PROBE SET ID | GENE SYMBOL | REFSEQ TRANSCRIPT ID | MEAN INTENSITY (V) | MEAN INTENSITY (N) | RATIO (V/N) |
|---|---|---|---|---|---|
| | | NM_080806/ | | | |
| | | NM_080807/ | | | |
| | | NM_080808/ | | | |
| | | NM_080809/ | | | |
| | | NM_080810/ | | | |
| | | NM_080811/ | | | |
| | | NM_080812/ | | | |
| | | NM_080813/ | | | |
| | | NM_080814/ | | | |
| | | NM_080815 | | | |
| 205900_at | KRT1 | NM_006121 | 37.24 | 95.82 | 0.39 |
| 203156_at | AKAP11 | NM_016248/ | 8.20 | 21.24 | 0.39 |
| | | NM_144490 | | | |
| 215245_x_at | FMR1 | NM_002024 | 30.13 | 78.43 | 0.38 |
| 201215_at | PLS3 | NM_005032 | 155.28 | 411.68 | 0.38 |
| 221553_at | RP11-217I1.1 | NM_032121/ XM_927839 | 34.17 | 90.64 | 0.38 |
| 203042_at | LAMP2 | NM_002294/ NM_013995 | 237.56 | 638.66 | 0.37 |
| 201132_at | HNRPH2 | NM_001032393/ NM_019597 | 52.45 | 143.04 | 0.37 |
| 221581_s_at | LAT2 | NM_014146/ NM_022040/ NM_032463 | 59.56 | 163.24 | 0.36 |
| 201865_x_at | NR3C1 | NM_000176/ NM_001018074/ NM_001018075/ NM_001018076/ NM_001018077/ NM_001020825/ NM_001024094 | 120.48 | 332.55 | 0.36 |
| 213593_s_at | TRA2A | NM_013293 | 12.37 | 34.25 | 0.36 |
| 210367_s_at | PTGES | NM_004878 | 88.52 | 246.35 | 0.36 |
| 212007_at | UBXD2 | NM_014607 | 41.95 | 117.00 | 0.36 |
| 205767_at | EREG | NM_001432 | 65.08 | 183.71 | 0.35 |
| 200914_x_at | KTN1 | NM_182926 | 118.02 | 343.43 | 0.34 |
| 210387_at | HIST1H2BG | NM_003518 | 198.74 | 579.17 | 0.34 |
| 202378_s_at | LEPROT | NM_017526 | 78.41 | 228.55 | 0.34 |
| 203780_at | EVA1 | NM_005797/ NM_144765 | 45.59 | 133.29 | 0.34 |
| 202435_s_at | CYP1B1 | NM_000104 | 15.25 | 44.59 | 0.34 |
| 221844_x_at | — | — | 32.98 | 96.74 | 0.34 |
| 212622_at | TMEM41B | NM_015012 | 8.86 | 26.02 | 0.34 |
| 201472_at | VBP1 | NM_003372 | 54.92 | 161.81 | 0.34 |
| 203303_at | DYNLT3 | NM_006520 | 15.03 | 44.35 | 0.34 |
| 204533_at | CXCL10 | NM_001565 | 8.07 | 24.04 | 0.34 |
| 212605_s_at | — | — | 13.86 | 41.36 | 0.34 |
| 214718_at | GATAD1 | NM_021167 | 11.00 | 33.09 | 0.33 |
| 209022_at | STAG2 | NM_006603 | 7.90 | 24.13 | 0.33 |
| 205623_at | ALDH3A1 | NM_000691 | 24.99 | 77.90 | 0.32 |
| 219956_at | GALNT6 | NM_007210 | 47.43 | 147.85 | 0.32 |
| 205128_x_at | PTGS1 | NM_000962/ NM_080591 | 39.76 | 125.00 | 0.32 |
| 202376_at | SERPINA3 | NM_001085 | 62.35 | 196.67 | 0.32 |
| 213229_at | DICER1 | NM_030621/ NM_177438 | 146.36 | 464.53 | 0.32 |
| 212223_at | IDS | NM_000202/ NM_006123 | 58.68 | 186.65 | 0.31 |
| 204584_at | L1CAM | NM_000425/ NM_024003 | 102.94 | 327.45 | 0.31 |
| 219995_s_at | FLJ13841 | NM_024702 | 245.82 | 795.33 | 0.31 |
| 219001_s_at | WDR32 | NM_024345 | 8.09 | 26.25 | 0.31 |
| 208241_at | NRG1 | NM_004495/ NM_013956/ NM_013957/ NM_013958/ NM_013959/ NM_013960/ NM_013961/ NM_013962/ NM_013964 | 5.57 | 18.19 | 0.31 |
| 211671_s_at | NR3C1 | NM_000176/ NM_001018074/ | 78.44 | 263.10 | 0.30 |

TABLE 1-continued

The 304 genes (350 Affymetrix probe sets or NCOR2-350) that are differentially
expressed in response to N-CoR2 overexpression in HMT3522 T4-2 cells.

| AFFYMETRIX PROBE SET ID | GENE SYMBOL | REFSEQ TRANSCRIPT ID | MEAN INTENSITY (V) | MEAN INTENSITY (N) | RATIO (V/N) |
|---|---|---|---|---|---|
| | | NM_001018075/ NM_001018076/ NM_001018077/ NM_001020825/ NM_001024094 | | | |
| 204602_at | DKK1 | NM_012242 | 76.05 | 259.47 | 0.29 |
| 213135_at | TIAM1 | NM_003253 | 7.06 | 24.42 | 0.29 |
| 204881_s_at | UGCG | NM_003358 | 34.89 | 120.86 | 0.29 |
| 206342_x_at | IDS | NM_000202/ NM_006123 | 77.09 | 267.58 | 0.29 |
| 218085_at | CHMP5 | NM_016410 | 23.89 | 84.03 | 0.28 |
| 212414_s_at | SEPT6 | NM_015129/ NM_032569/ NM_145799/ NM_145800/ NM_145802 | 19.17 | 68.28 | 0.28 |
| 215206_at | EXT1 | NM_000127 | 29.69 | 106.70 | 0.28 |
| 205097_at | SLC26A2 | NM_000112 | 23.64 | 85.76 | 0.28 |
| 204976_s_at | AMMECR1 | NM_001025580/ NM_015365 | 9.92 | 36.28 | 0.27 |
| 204351_at | S100P | NM_005980 | 48.68 | 180.28 | 0.27 |
| 217975_at | WBP5 | NM_001006612/ NM_001006613/ NM_001006614/ NM_016303 | 108.30 | 441.28 | 0.25 |
| 205363_at | BBOX1 | NM_003986 | 29.13 | 120.76 | 0.24 |
| 209792_s_at | KLK10 | NM_002776/ NM_145888 | 120.93 | 505.96 | 0.24 |
| 202439_s_at | IDS | NM_000202/ NM_006123 | 64.34 | 270.52 | 0.24 |
| 212221_x_at | IDS | NM_000202/ NM_006123 | 133.36 | 571.11 | 0.23 |
| 200821_at | LAMP2 | NM_002294/ NM_013995 | 81.15 | 347.91 | 0.23 |
| 201917_s_at | SLC25A36 | NM_018155 | 6.22 | 28.72 | 0.22 |
| 205569_at | LAMP3 | NM_014398 | 13.64 | 64.51 | 0.21 |
| 204750_s_at | DSC2 | NM_004949/ NM_024422 | 33.27 | 159.80 | 0.21 |
| 218668_s_at | RAP2C | NM_021183 | 11.22 | 54.25 | 0.21 |
| 205809_s_at | WASL | NM_003941 | 15.28 | 77.44 | 0.20 |
| 201007_at | HADHB | NM_000183 | 1389.06 | 7136.54 | 0.19 |
| 203453_at | SCNN1A | NM_001038 | 14.92 | 142.26 | 0.10 |
| 202411_at | IFI27 | NM_005532 | 13.86 | 155.11 | 0.09 |

Example 2

This example demonstrates that N-CoR2 and HDAC3 expression is prognostic of the clinical outcome in breast cancer patients.

The transcriptional expression levels of N-CoR2, HDAC3, and associated clinical information, including therapeutic outcome and survival, were obtained from several publicly available tumor transcriptome data sets, including 295 patients with primary breast carcinomas (N. Engl. J. Med. 347:1999-2009 (2002)), 50 patients with malignant gliomas (Cancer Res. 63:1602-1607 (2003)), and 60 patients with ovarian carcinomas (J. Clin. Oncol. 22:4700-4710 (2004)). The patient survival data from the ovarian cancer data set was provided by D. Spentzos (Beth Israel Deaconess Medical Center and Harvard Medical School, Boston, Mass.). We searched the probe hybridization ratio (for two-color cDNA arrays) or the probe signal intensity (for Affymetrix arrays) of N-CoR2 (NCOR2) and HDAC3 (HDAC3) in each data set. If NCOR2 was represented by more than one probe set, the one that displayed the highest hybridization intensity in respective array platforms (e.g., 207760_s_at in Affymetrix HG-U133A 2.0 array; 39358_at in Affymetrix HG-U95 array; IMAGE:80772 for cDNA array) were chosen for the analysis.

The patients were grouped into quartiles based on the relative (untransformed) expression levels of N-CoR2 or HDAC3 in respective data sets. For the breast cancer data sets, patients were stratified according to their lymph node (LN), positive or negative, and chemotherapy (CT) status. The probability of remaining relapse-free or overall survival was computed using the method of Kaplan and Meier (J. Am. Stat. Assoc. 53:457-481 (1958)). The curves were plotted and compared using the log-rank test with the software packages SPSS15.0 (SPSS Inc.) and GraphPad Prism 3.02 (GraphPad Software). The log-rank test was used to calculate the P values. Multivariate analysis of survival with the use of the Cox proportional hazard method was performed with the software package SPSS15.0 (SPSS Inc.).

Figure 1B:
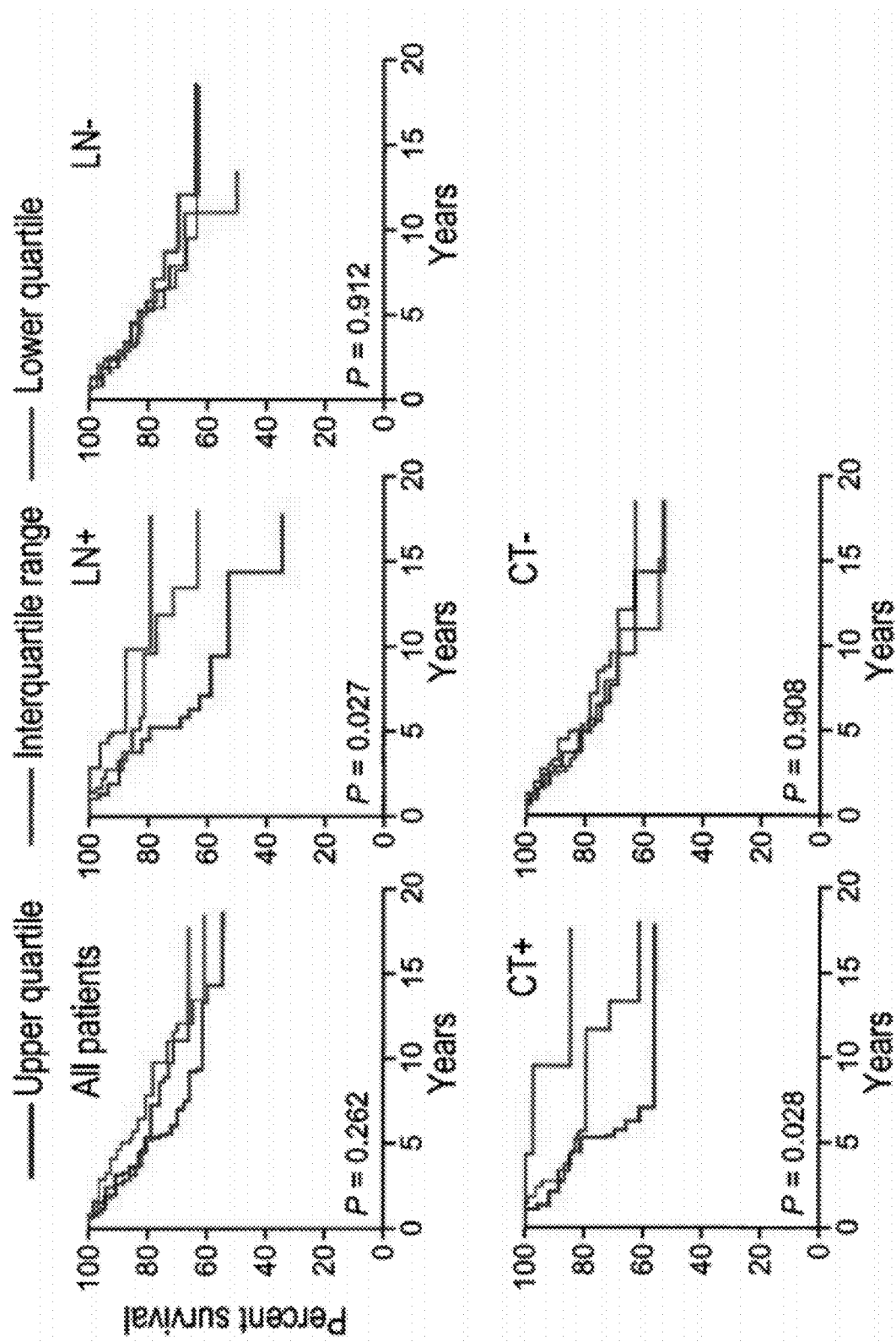

In FIG. 1, a 295 breast cancer patient data set from the Netherlands Cancer Institute (N. Engl. J. Med. 347:1999-2009 (2002)) was divided into the following three groups according to the expression quartiles of N-CoR2: (1) upper quartile, (2) interquartile range, and (3) lower quartile. The probability of remaining free of post-therapeutic disease relapse (FIG. 1A) or overall survival (FIG. 1B) was plotted over a 20-year period of follow-up. The Kaplan-Meier curves shows that patients with the expression levels of N-CoR2 in the upper quartile had significantly higher probability of post-therapeutic disease relapse and mortality than those with expression levels in the lower quartile. The association of N-CoR2 with clinical outcomes was most prominent and significant in patients with LN-positive disease and those who had received adjuvant systemic CT.

Figure 2A:
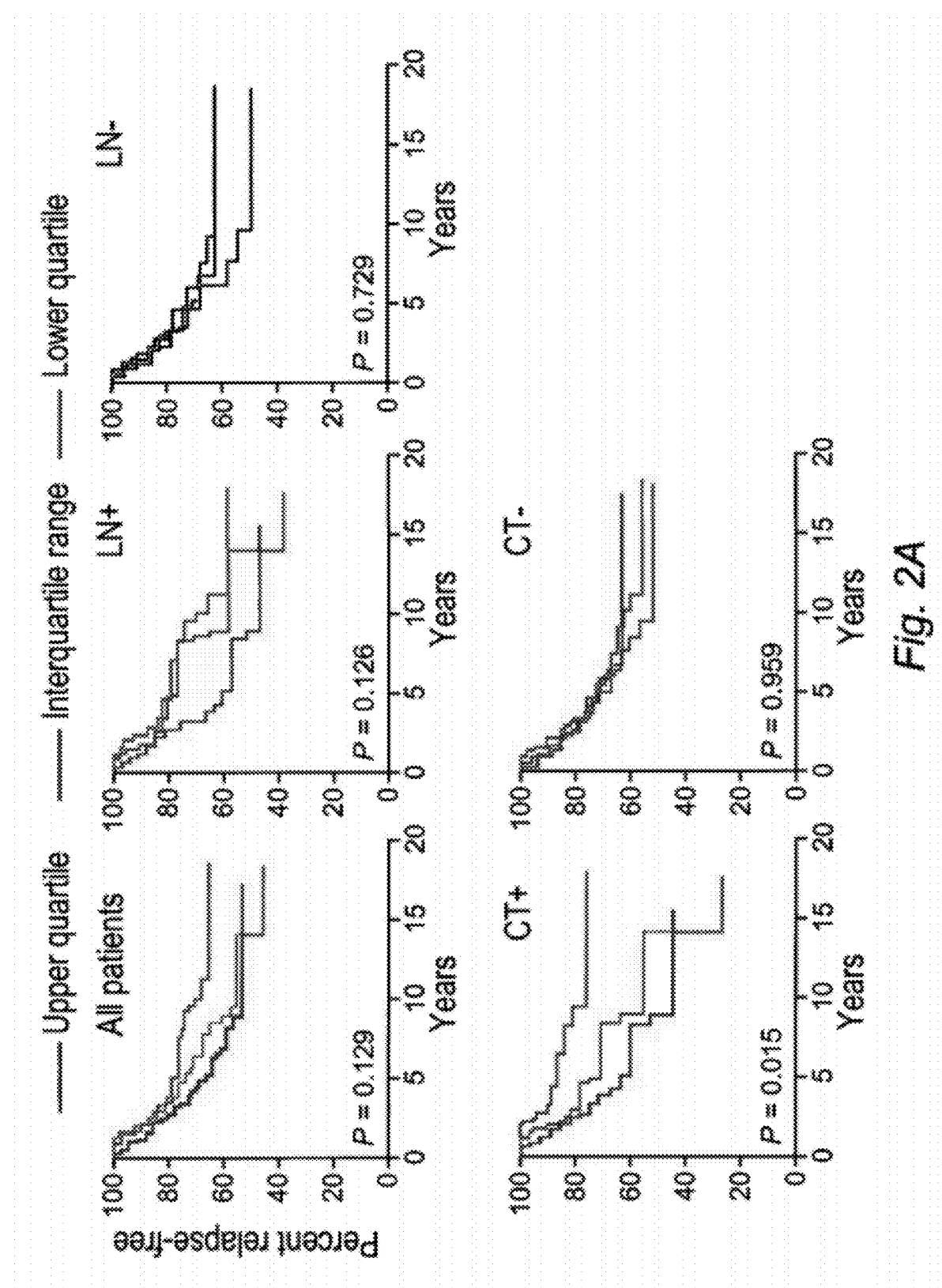
FIG. 2 Kaplain-Meier graphs of the probability that a patient would remain relapse-free (FIG. 2A) or survive (FIG. 2B) as a function of time from diagnosis among 295 breast cancer patients in the Netherlands Cancer Institute data set. The patients were grouped into quartiles according to the expression levels of HDAC3. The patients were further stratified according to their LN status and whether or not they received adjuvant systemic chemotherapy (CT). The patients in each group were stratified according to HDAC3 gene expression quartiles.
Figure 2B:
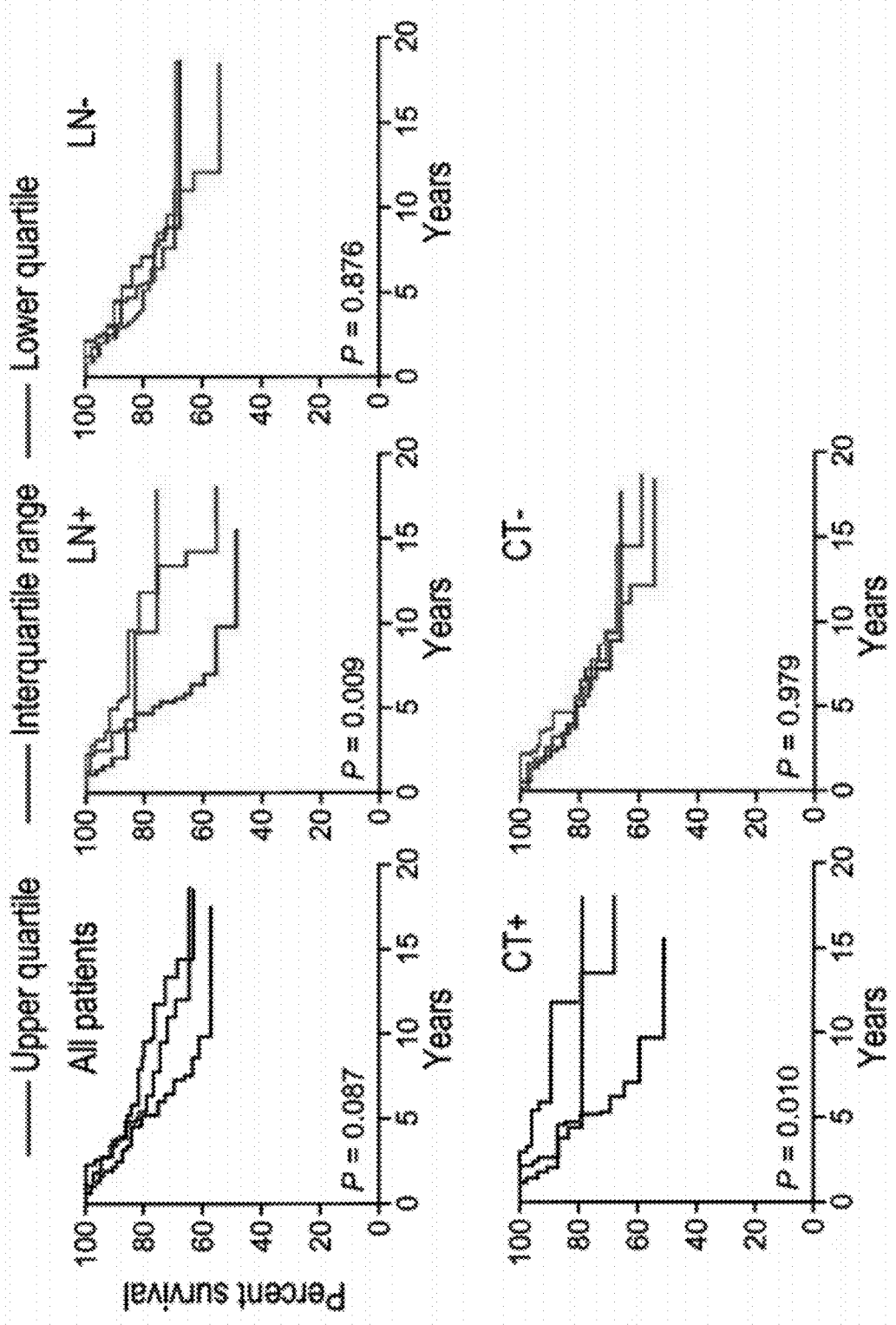

FIG. 2 shows a similar analysis of the clinical outcome of the 295 breast cancer patients in the Netherlands Cancer Institute data set with respect to the expression quartiles of HDAC3. Similar to N-CoR2, the patients with the expression levels of HDAC3 in the upper quartile had significantly higher probability of post-therapeutic disease relapse (FIG. 2A) and mortality (FIG. 2B) than those with expression levels in the lower quartile, and the association was most prominent and significant in patients with LN-positive disease and those who had received adjuvant systemic CT.

Figure 3A:
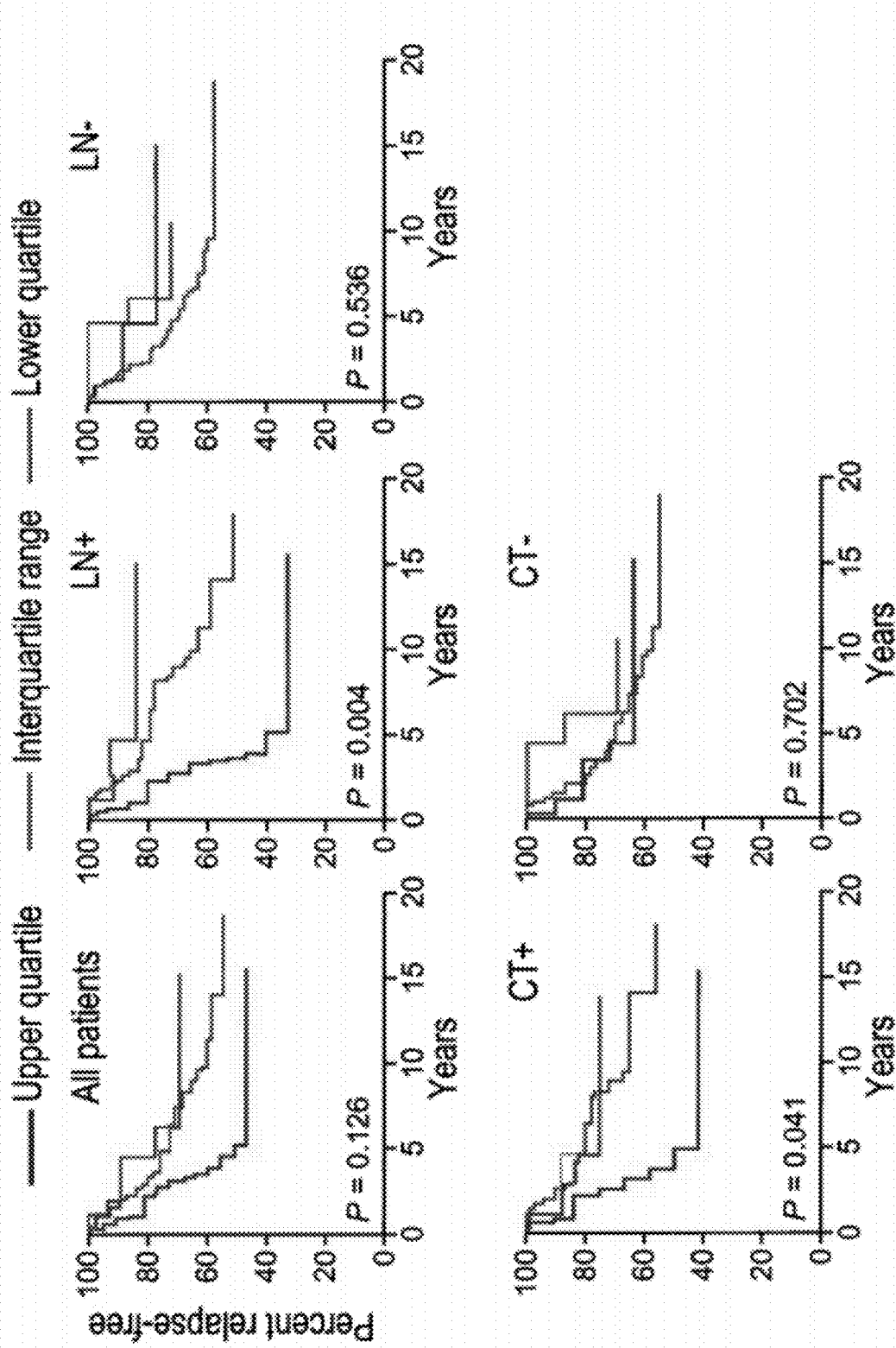
FIG. 3 Kaplain-Meier analysis of the probability that patient would remain relapse-free (FIG. 3A) or survive (FIG. 3B) as a function of time from diagnosis among 295 breast cancer patients in the Netherlands Cancer Institute data set. The patients were divided into quartiles according to the expression levels of N-CoR2 or HDAC3, respectively, and then further grouped according to whether their N-CoR2 and HDAC3 gene expressions both fell into respective upper or lower quartile or the Interquartile range. The patients were further stratified according to their LN status and whether or not they received adjuvant systemic chemotherapy (CT). The patients in each group were stratified according to N-CoR2 and HDAC3 gene expression similarly.
Figure 3B:
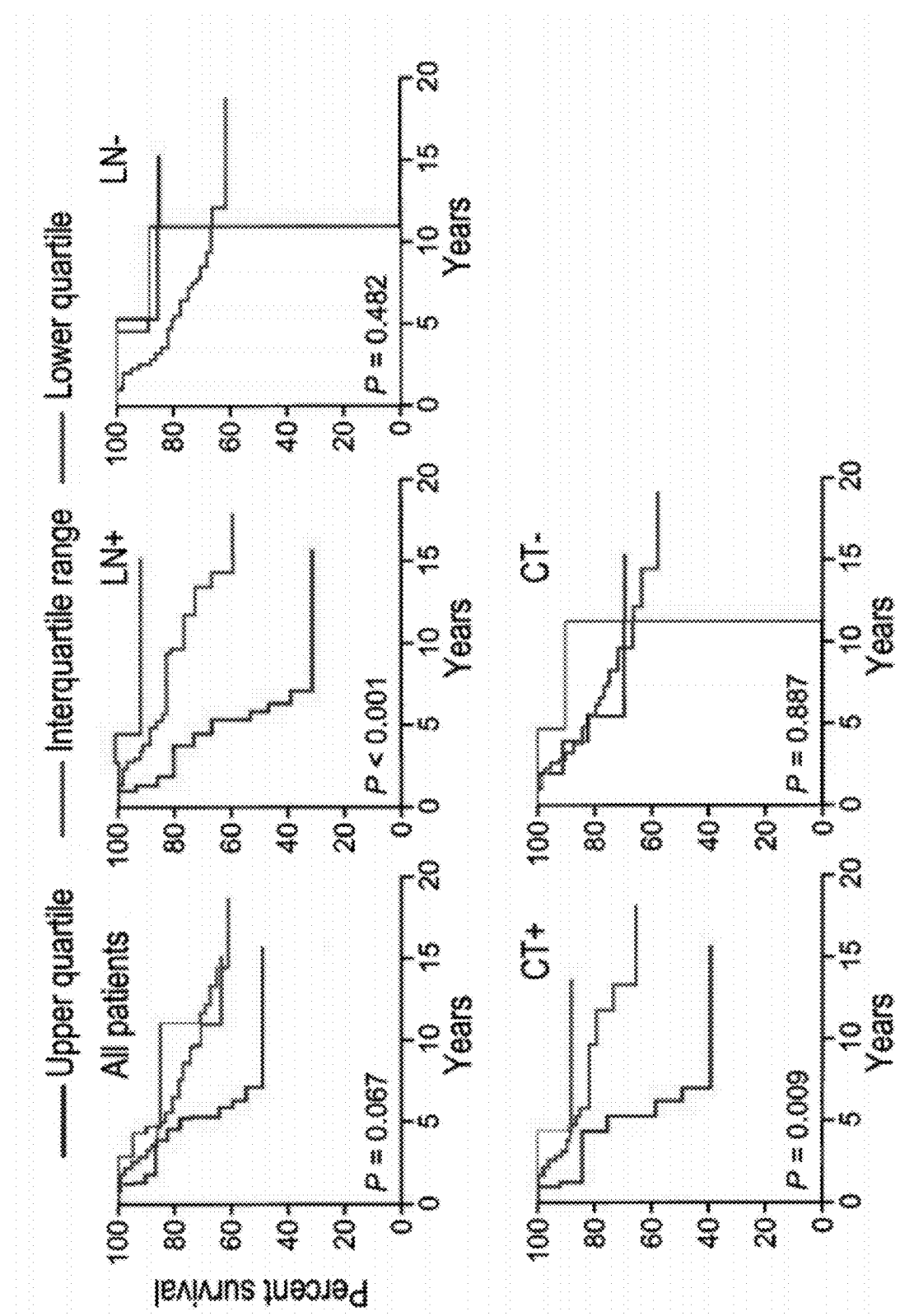

FIG. 3 shows a similar analysis of the clinical outcome of the 295 breast cancer patients of the Netherlands Cancer Institute data set according to whether their expression levels of N-CoR2 and HDAC3 both fall in respective upper or lower quartiles. In patients with LN-positive disease or those who had received adjuvant systemic CT, those with expression levels of both N-CoR2 and HDAC3 in the upper quartiles had remarkably high probabilities of relapse (FIG. 3A) and mortality (FIG. 3B) and around two-thirds of the patients developed disease progression within 5 years. In contrast, the patients expression levels of both N-CoR2 and HDAC3 in the lower quartiles had a low probability of disease relapse or mortality.

Table 2 shows a multivariate Cox proportional-hazards analysis on the association of the expression levels of N-CoR2 and HDAC3 with clinical outcome of the 295 breast cancer patients from the Netherlands Cancer Institute data set who were stratified according to clinical characteristics including age, tumor size, LN and ER status, histological grade, molecular subtypes (Proc. Natl. Acad. Sci. USA 100: 8418-8423 (2003)), and CT status. N-CoR2 but not HDAC3 was an independent predictive factor of the relapse-free and overall survival. The association between N-CoR2 expression and death or relapse was independent of age, tumor size and differentiation. Of all the independent predictive factors, N-CoR2 was the strongest predictor of the likelihood of disease relapse and mortality, with a hazard ratio of 1.96 (P=0.007) and 1.87 (P=0.005), respectively.

TABLE 2

Multivariable Cox proportional-hazards analysis on the association of the expression levels of N—CoR2 and HDAC3 with clinical outcome of the 295 breast cancer patients from the Netherlands Cancer Institute data set who were stratified according to clinical characteristics including age, tumor size, LN and ER status, histological grade, molecular subtypes, and CT status.

| Variable | Death Hazard Ratio (95% CI) | P Value | Relapse Hazard Ratio (95% CI) | P Value |
|---|---|---|---|---|
| N—CoR2 | 1.96 (1.2-3.18) | 0.007 | 1.87 (1.21-2.9) | 0.005 |
| HDAC3 | 1.56 (0.76-3.19) | 0.221 | 0.99 (0.5-1.95) | 0.97 |
| Age (per 10-yr increment) | 0.7 (0.47-1.05) | 0.087 | 0.6 (0.42-0.85) | 0.005 |
| Tumor size (per cm) | 1.26 (0.98-1.63) | 0.07 | 1.26 (1.00-1.57) | 0.047 |
| Tumor grade | | 0.011 | | 0.017 |
| Grade 2 vs. grade 1 | 3.94 (1.35-11.47) | | 2.24 (1.12-4.48) | |
| Grade 3 vs. grade 1 | 5.18 (1.77-15.14) | | 2.81 (1.38-5.7) | |
| Positive LN status vs. negative status | 1.5 (0.75-2.97) | 0.249 | 1.56 (0.86-2.85) | 0.146 |
| Positive ER status vs. negative status | 0.66 (0.33-1.31) | 0.232 | 0.97 (0.52-1.82) | 0.927 |
| Chemotherapy vs. no chemotherapy | 0.59 (0.29-1.23) | 0.16 | 0.54 (0.29-1.02) | 0.056 |
| Hormonal treatment vs. no treatment | 0.83 (0.34-2.06) | 0.693 | 0.7 (0.32-1.53) | 0.372 |
| Mastectomy vs. breast-conserving therapy | 0.97 (0.6-1.57) | 0.886 | 0.9 (0.59-1.38) | 0.628 |
| Molecular subtype | | 0.075 | | 0.182 |
| Normal-like & luminal B vs. luminal A | 1.72 (0.81-3.66) | | 1.47 (0.82-2.62) | |
| Basal & ERBB2+ vs. luminal A | 2.74 (1.15-6.53) | | 1.92 (0.96-3.85) | |

Table 3 shows a multivariate Cox proportional-hazards analysis on the association of the expression levels of N-CoR2 and HDAC3 with clinical outcome of the 110 breast cancer patients who had received adjuvant (postoperative) systemic CT identified from the 293 breast cancer patients of the Netherlands Cancer Institute data set. The patients were stratified according to age, tumor size, LN and ER status, histological grade and molecular subtypes. In this subgroup of the patients, both N-CoR2 and HDAC3 were independent predictive factors of the risk of mortality, while only N-CoR2 was independently associated with death and relapse (P<0.001). Compared with clinical characteristics and molecular classification of breast cancers, N-CoR2 was the strongest predictor of the likelihood of disease relapse and mortality with hazard ratios of 9.64 (P<0.001) and 5.45 (P<0.001), respectively.

TABLE 3

Multivariate Cox proportional-hazards analysis on the association of the expression levels of N—CoR2 and HDAC3 with clinical outcome of the 110 breast cancer patients who had received adjuvant (postoperative) systemic CT.

| Variable | Death Hazard Ratio (95% CI) | P Value | Relapse Hazard Ratio (95% CI) | P Value |
|---|---|---|---|---|
| N—CoR2 | 9.64 (3.27-28.43) | <0.001 | 5.45 (2.31-12.85) | <0.001 |
| HDAC3 | 6.67 (1.67-26.65) | 0.007 | 1.89 (0.5-7.11) | 0.348 |
| Age (per 10-yr increment) | 0.57 (0.24-1.35) | 0.199 | 0.69 (0.38-1.41) | 0.305 |
| Tumor size (per cm) | 1.60 (1.0-2.57) | 0.05 | 1.43 (0.97-1.21) | 0.068 |
| Tumor grade | | 0.12 | | 0.18 |
| Grade 2 vs. grade 1 | 1.82 (0.33-9.96) | | 1.2 (0.38-3.76) | |
| Grade 3 vs. grade 1 | 4.3 (0.84-22.11) | | 2.45 (0.79-7.58) | |
| Positive LN status vs. negative status | 0.46 (0.09-2.28) | 0.339 | 0.85 (0.19-3.87) | 0.831 |
| Positive ER status vs. negative status | 0.09 (0.02-0.41) | 0.002 | 0.23 (0.06-0.85) | 0.027 |
| Hormonal treatment vs. no treatment | 0.24 (0.03-1.91) | 0.176 | 0.53 (0.16-1.82) | 0.315 |
| Mastectomy vs. breast-conserving therapy | 0.81 (0.32-2.04) | 0.653 | 0.81 (0.38-1.75) | 0.591 |
| Molecular subtype | | 0.314 | | 0.53 |
| Normal-like & luminal B vs. luminal A | 3.77 (0.63-22.64) | | 1.59 (0.51-4.95) | |
| Basal & ERBB2+ vs. luminal A | 1.93 (0.3-12.41) | | 0.88 (0.22-3.58) | |

Table 4 shows a multivariate Cox proportional-hazards analysis on the association of the expression levels of N-CoR2 and HDAC3 with clinical outcome of the 185 breast cancer patients who did not received adjuvant (postoperative) systemic CT identified from the 293 breast cancer patients of the Netherlands Cancer Institute database. Unlike the patients who had received adjuvant systemic CT, the molecular subtypes of breast cancers was the strongest predictor of the risk of death (P=0.005) and disease relapse (P=0.025) in the patients who did not receive adjuvant CT, whereas neither N-CoR2 nor HDAC3 was independent predictive factor of clinical outcome in this subgroup of the patients.

Figure 4A:
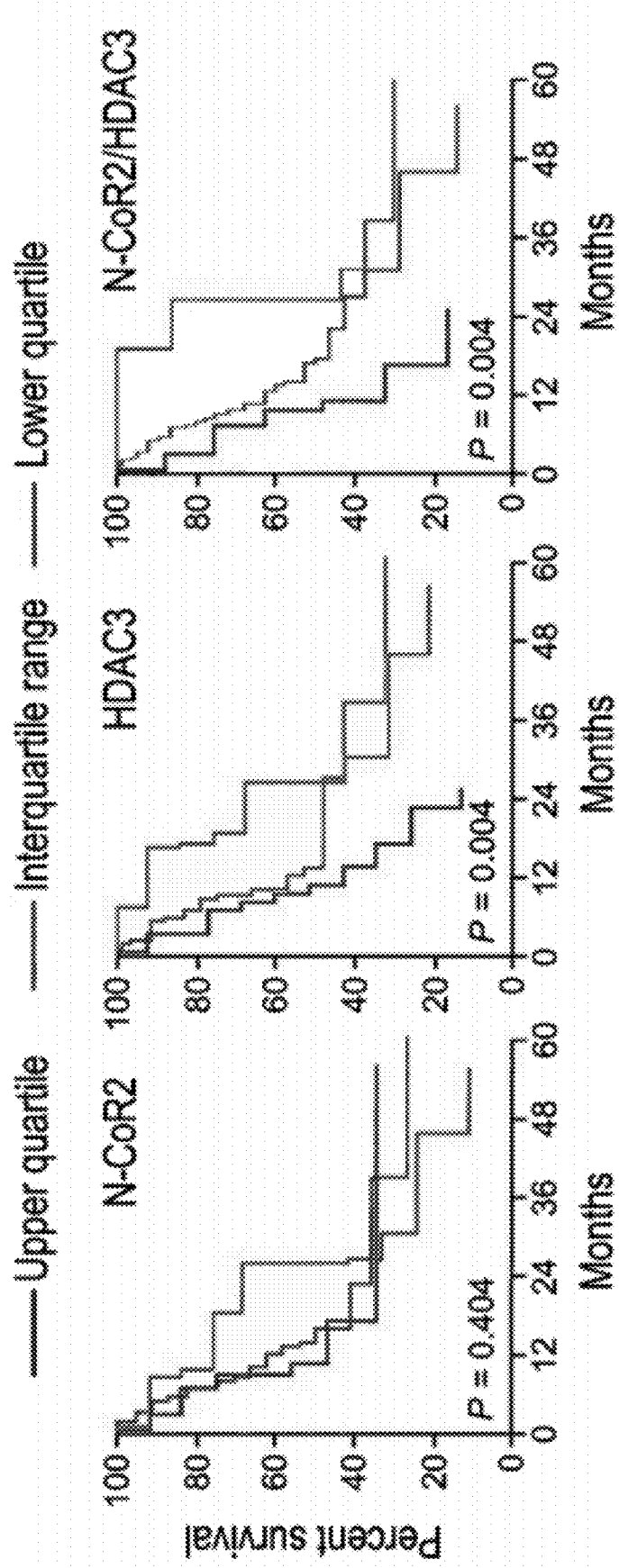
FIG. 4 The probability that patient would remain survive as a function of time from diagnosis among 50 patients with malignant gliomas (FIG. 4A) and 60 patients with ovarian cancers (FIG. 4B). The patients were divided into quartiles according to the expression levels of N-CoR2 or HDAC3, respectively, and then further grouped according to whether their N-CoR2 and HDAC3 gene expressions both fell into respective upper or lower quartile or the Interquartile range. The patients were further stratified according to their LN status and whether or not they received adjuvant systemic chemotherapy (CT). The patients in each group were stratified according to N-CoR2 and HDAC3 gene expression similarly. P values were determined using the log-rank test comparing the upper and lower quartiles or the interquartile range (*).
Figure 4B:
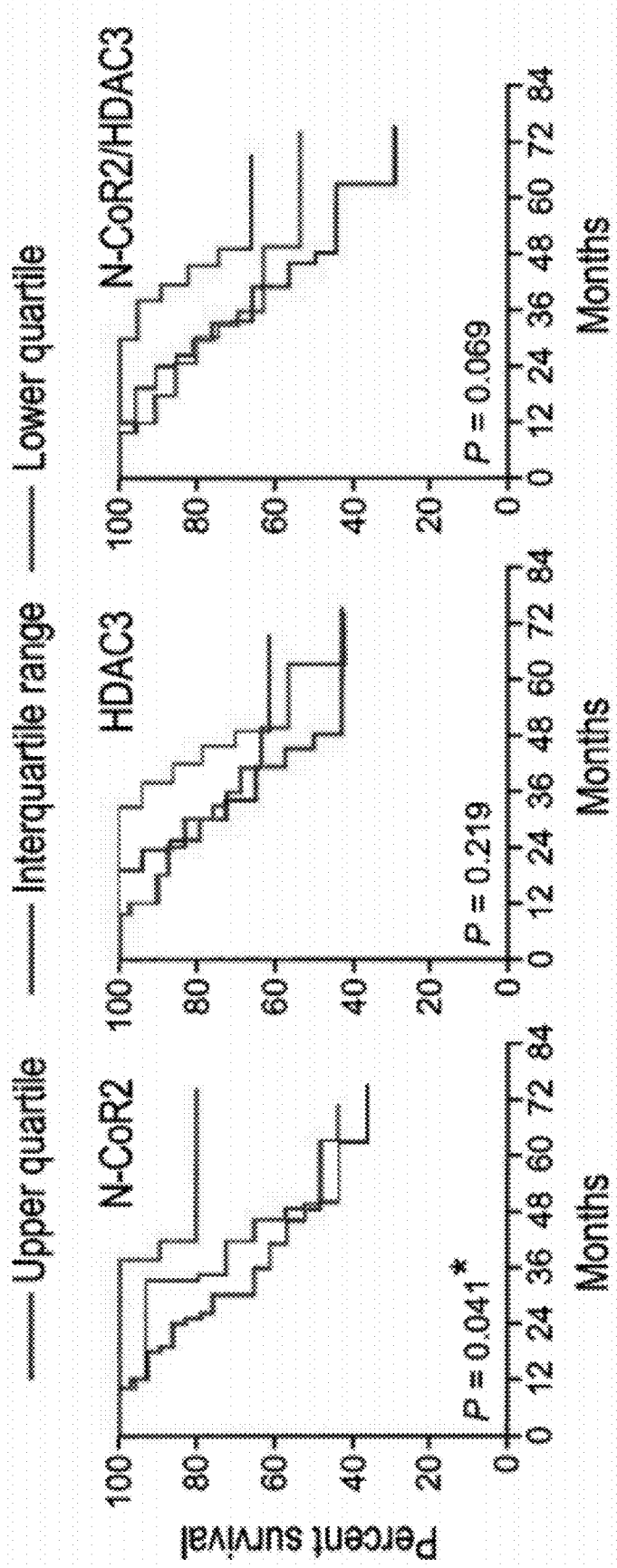

In FIG. 4, 50 patients with malignant gliomas (Cancer Res. 63:1602-1607 (2003)) (FIG. 4A) and 60 patients with ovarian cancers (J. Clin. Oncol. 22:4700-4710 (2004)) (FIG. 4B) were divided into quartiles according to their expression levels of N-CoR2 and/or HDAC3, respectively. Kaplan Meier survival analysis shows that higher N-CoR2 and/or HDAC3 expressions were associated with higher probability of mortality in both types of human malignancies. Tumors stratified according to their expression levels of N-CoR2 and HDAC3 displayed trends of mortality similar to those stratified using the expression levels of N-CoR2 or HDAC3 alone, suggesting

TABLE 4

Multivariate Cox proportional-hazards analysis on the association of the expression levels of N—CoR2 and HDAC3 with clinical outcome of the 185 breast cancer patients who did not received adjuvant (postoperative) systemic CT.

| Variable | Death Hazard Ratio (95% CI) | P Value | Relapse Hazard Ratio (95% CI) | P Value |
|---|---|---|---|---|
| N—CoR2 | 1.12 (0.54-2.31) | 0.761 | 1.25 (0.69-2.28) | 0.46 |
| HDAC3 | 1.15 (0.46-2.88) | 0.761 | 0.92 (0.39-2.15) | 0.841 |
| Age (per 10-yr increment) | 0.71 (0.44-1.16) | 0.177 | 0.58 (0.38-0.91) | 0.018 |
| Tumor size (per cm) | 1.35 (0.94-1.85) | 0.115 | 1.21 (0.89-1.65) | 0.22 |
| Tumor grade | | 0.057 | | 0.047 |
| Grade 2 vs. grade 1 | 5.28 (1.18-23.55) | | 2.81 (1.1-7.15) | |
| Grade 3 vs. grade 1 | 6.25 (1.4-28.0) | | 3.35 (1.27-8.83) | |
| Positive LN status vs. negative status | 1.48 (0.69-3.15) | 0.316 | 1.62 (0.84-3.12) | 0.147 |
| Positive ER status vs. negative status | 1.48 (0.62-3.55) | 0.375 | 1.87 (0.85-4.12) | 0.123 |
| Hormonal treatment vs. no treatment | 1.16 (0.37-3.62) | 0.8 | 0.75 (0.25-2.23) | 0.604 |
| Mastectomy vs. breast-conserving therapy | 1.48 (0.81-2.71) | 0.201 | 1.61 (0.93-2.78) | 0.088 |
| Molecular subtype | | 0.005 | | 0.025 |
| Normal-like & luminal B vs. luminal A | 1.88 (0.76-4.64) | | 1.45 (0.71-2.95) | |
| Basal & ERBB2+ vs. luminal A | 5.65 (1.93-16.52) | | 3.2 (1.35-7.55) | | that N-CoR2 and HDAC3 may play synergistic roles in mediating unfavorable clinical outcome in human malignancies.

Example 3

This example demonstrates that genes whose expressions are associated with N-CoR2 are prognostic classifiers for the response to preoperative combinational chemotherapy in breast cancers.

To further show that the N-CoR2 signature genes are associated with increased resistance to systemic chemotherapy independent of other therapeutic interventions, the tumor transcriptome data set from a cohort of 133 breast cancer patients who received pre-operative (neoadjuvant) combination chemotherapy, including paclitaxel and fluorouracil-doxorubicin-cyclophosphamide, wherein the treatment responses were pathologically defined (J. Clin. Oncol. 24:4236-4244 (2006)), at the M.D. Anderson Cancer Center were analyzed. The patients who did not have residual cancer cells in the breast by pathological examinations following chemotherapy were considered as having clinically beneficial responses (i.e., "responders") and those having residual cancer cells in the breast as "non-responders". Three patients without available information on the post-treatment breast pathological data from the original data set were excluded, leaving a total of 130 cases for the analysis.

As shown in Example 1 and Table 1, a list of 304 N-CoR2-associated genes (represented by 350 Affymetrix probe sets or "NCOR2-350") were identified based on their expression levels (on a $\log_2$ base) significantly different (fold change $\geq 2$ and a cutoff P-value <0.05 by Student's t test) between T4-2-N-CoR2 cells and the vector control cells. These genes were extracted from the gene expression profiles of the 130 patients and their respective probe signal intensity data were median-centered. Average linkage clustering was carried out using the Cluster and TreeView software (Proc. Natl. Acad. Sci. USA 95:14863-14868 (1998)).

We further determined whether expression profiles of genes altered by N-CoR2 in 3D tissue cultures would recapitulate the expression profiles of N-CoR2-regulated genes in tumors, which could be quantified by measuring their similarities to each other. We normalized and median-centered the average expression levels (on a $\log_2$ scale) of NCOR2-350 in T4-2-N-CoR2 cells, the vector control cells and the 130 breast tumors in the M.D. Anderson Cancer Center data set (J. Clin. Oncol. 24:4236-4244 (2006)). We then measured the degree of resemblance between the expression profiles of NCOR2-350 in the 130 breast tumors and those in T4-2 N-CoR2 cells or the vector control cells using Pearson's correlation coefficient, which yielded $r_{NOR2}$ and $r_{vector}$, respectively. Tumors with greater $r_{NCOR2}$ than $r_{vector}$ were considered of having higher transcriptional activities associated with N-CoR2 and a NCOR2-350-based N-CoR2 transcription activity similarity score "$S_{NCOR2-350}$" is used to represent the difference between $r_{NCOR2}$ and $r_{vector}$, $$S_{NCOR2-350} = r_{NCOR2} - r_{vector} \quad \text{(Equation 1)}$$

As shown in Table 5, the breast tumors with higher expression levels of N-CoR2 had an increase in the odds (2.2-fold) of unresponsiveness to pre-operative CT compared with those with lower expression levels. This finding was statistically significant, p=0.029.

TABLE 5

Results from the analysis of N—CoR2 expression in a cohort of 130 patients with breast cancer.

| Predictor | Group | Responder (%) | Non-responder (%) | Odds ratio (95% Confidence Interval) | P value |
|---|---|---|---|---|---|
| N—CoR2 | High | 15 (23.1) | 50 (76.9) | 2.2 (1.0-4.8) | 0.029* |
| | Low | 26 (40) | 39 (60) | 1 | |

*P values were calculated with use of Fisher's exact test.

Figure 5:
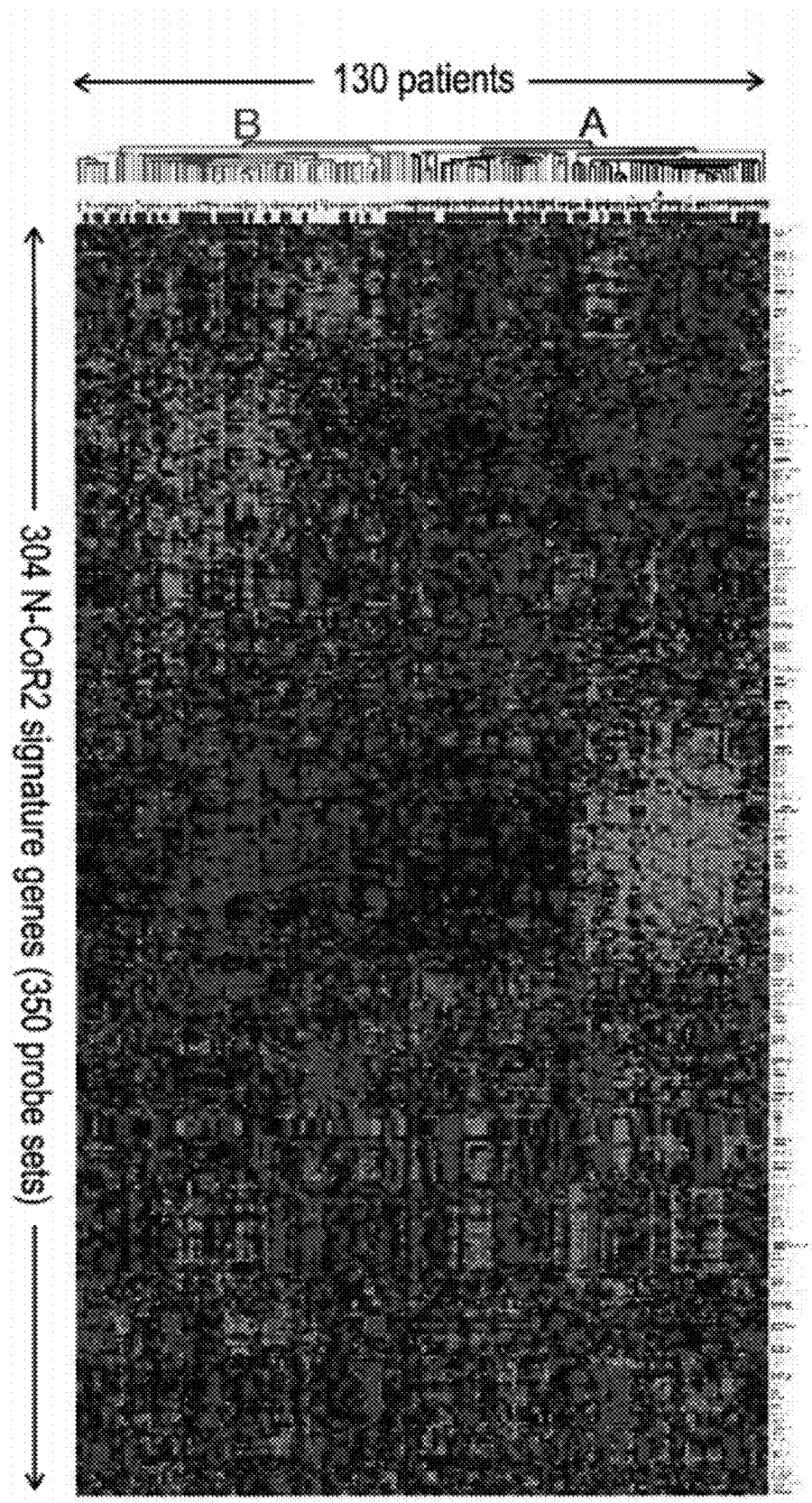
FIG. 5 Classification of the 130 breast carcinomas of the M.D. Anderson Cancer Center datab set into prognostic groups using hierarchical clustering analysis on the 304 N-CoR2-associated genes (represented by 350 Affymetrix probe sets). The tumors were segregated into two predominant subgroups (subgroup A and subgroup B) based on the first bifurcation in the dendrogram.

In FIG. 5, a hierarchical clustering analysis based on the expression pattern of NCOR2-350 segregated the 130 breast carcinomas into two predominant subgroups (subgroup A and subgroup B) based on the first bifurcation in the dendrogram. Table 6 shows that the breast tumors that were allocated in subgroup A by average linkage clustering analysis had a 3.5-fold increase in the odds ratio of unresponsiveness (i.e., nonresponders, represented by black circles) to pre-operative systemic CT than those allocated in subgroup B.

TABLE 6

Results from the analysis of the transcriptional expression of NCOR2-350 in a cohort of 130 patients with breast cancer.

| Predictor | Group | Responder (%) | Non-responder (%) | Odds ratio (95% Confidence Interval) | P value |
|---|---|---|---|---|---|
| Average Lineage Clustering | Subgroup A | 13 (19.1) | 55 (80.9) | 3.5 (1.6-7.6) | 0.001* |
| | Subgroup B | 28 (45.2) | 34 (54.8) | 1 | |

*P values were calculated with use of Fisher's exact test.

Figure 6:
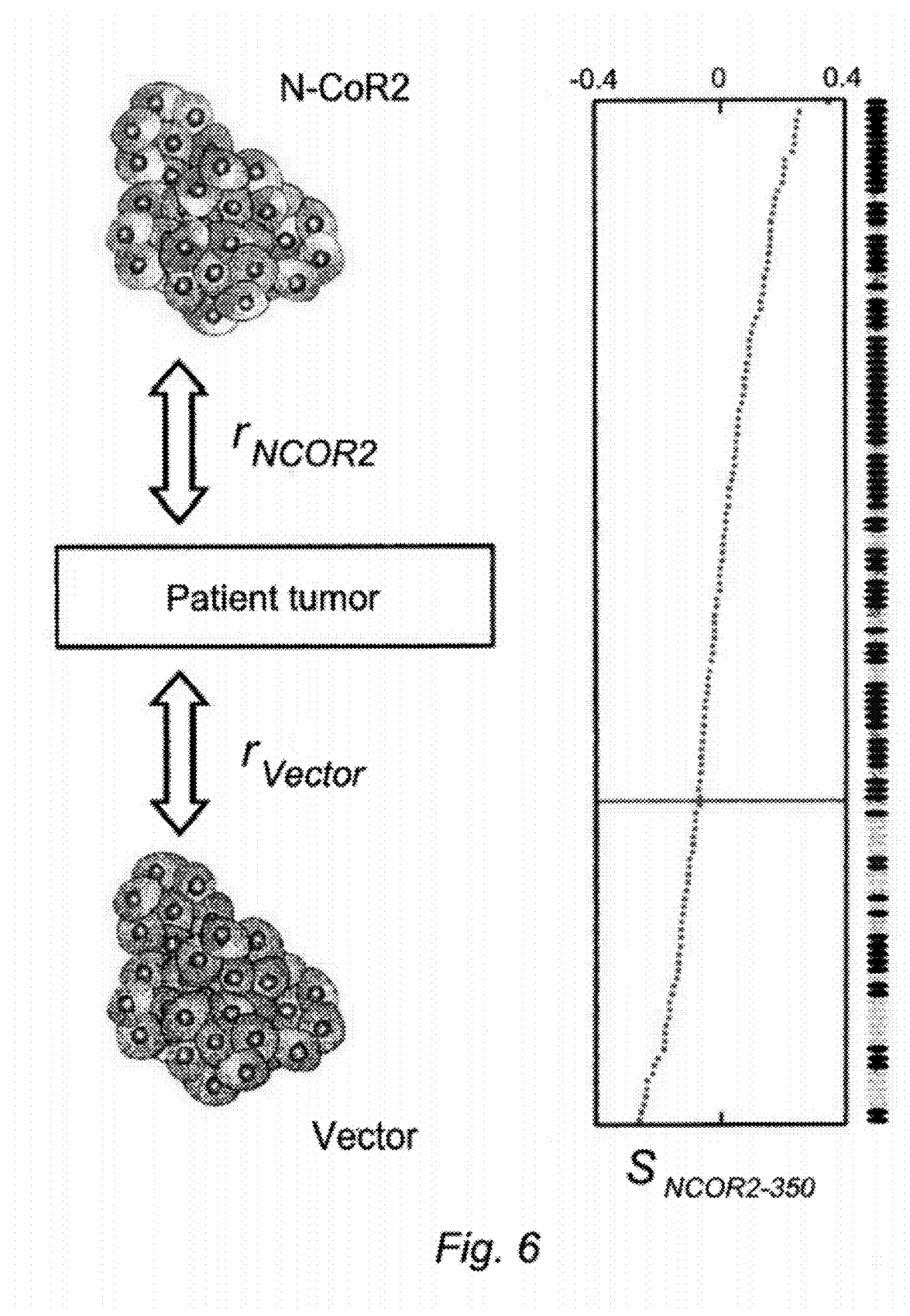
FIG. 6 Classification of the 130 breast carcinomas of the M.D. Anderson Cancer Center data set into treatment response groups using $S_{NCOR2-350}$ as a measure of the N-CoR2-associated transcriptional activities in breast cancer cells. Shown in the left panel is schematic representation of the derivation of $r_{NCOR2}$ and $r_{vector}$ by calculating the Pearson's correlation coefficient of the expression profile of NCOR2-350 between a patient tumor and T4-2-N-CoR2 cells ($r_{NcoR2}$) or the vector control cells ($r_{vector}$). $S_{NCOR2-350}$ is used to represent the difference between $r_{NCOR2}$ and $r_{vector}$. Shown in the right panel is the distribution of $S_{NCOR2-350}$ among the 130 breast carcinomas. The solid line represents a cut-off value of $S_{NCOR2-350}$ that best discriminates among nonresponders (black circles) and responders (yellow circles) as determined by the area under the ROC curve.

In FIG. 6 $S_{NCOR2-350}$ was used as a measure of the N-CoR2-associated transcriptional activities in breast cancer cells. Shown in the left panel is a schematic representation of the derivation of $r_{NCOR2}$, $r_{vector}$ and $S_{NCOR2-350}$. The 130 patient breast tumors in the M.D. Anderson Cancer Center data set are sorted descendingly according to their respective $S_{NCOR2-350}$ and a cut-off value of −0.0698 (red line) was determined to best discriminate among nonresponders (represented by black circles) and responders (represented by yellow circles) to neoadjuvant chemotherapy using the area under the receiver operating characteristic (ROC) curve. Said ROC curve as used herein refers to a graphical display of the false-positive rate and the true-positive rate from multiple classification rules (J. Natl. Cancer Inst. 95:511-515 (2003)). The tumors with $S_{NCOR2}$ values higher than this cut-off value had higher correlations with respect to the expressions of NCOR2-350 with T4-2-N-CoR2 cells and lower correlations with the vector control cells. On the contrary, the tumors with $S_{NCOR2}$ values lower than this cut-off value had lower correlations with respect to the expression of NCOR2-350 with T4-2-N-CoR2 cells and higher correlations with the vector control cells.

As shown in Table 7, the breast tumors with $S_{NCOR2-350}$ values higher than said cut-off value had a 6.0-fold higher odds ratio of unresponsiveness to neoadjuvant chemotherapy compared with those with lower $S_{NCOR2-350}$ values (p=<0.001).

TABLE 7

$S_{NCOR2}$ analysis of the transcriptional profile of NCOR2-350 in a cohort of 130 patients with breast cancer.

| Predictor | Group | Responder (%) | Non-responder (%) | Odds ratio (95% Confidence Interval) | P value |
|---|---|---|---|---|---|
| $S_{NCOR2-350}$ | High | 17 (19.1) | 72 (80.9) | 6.0 (2.5-14.7) | <0.001* |
| | Low | 24 (58.5) | 17 (41.5) | 1 | |

*P values were calculated with use of Fisher's exact test.

As shown in Table 8, the likelihood of unresponding to pre-operative CT of the 130 breast cancer patients of the M.D. Anderson Cancer Center data set was analyzed using a logistic regression model including age, tumor size, nuclear grade, LN, ER and HER2 status as predictors. Of all the clinical characteristics, only ER status (P=0.003) and age (P=0.037) are significantly predictors. Patient stratification by hierarchical clustering analysis based on NCOR2-350 was also an independent predictor of the likelihood of resistance to pre-operative CT with an odds ratio of 2.71 (P=0.038). In Table 9, a similar logistic regression model including $S_{NCOR2-350}$ and clinicopathological variables of the patients shows that $S_{NCOR2}$ also independently provides a strong prognostic measure of the likelihood of unresponsiveness to pre-operative CT (Odds ratio 6.47; P<0.001).

TABLE 8

Analysis of prognostic methods in a cohort of 130 breast cancer patients.

| Variable | Odds Ratio (95% Confidence Interval) | P value |
|---|---|---|
| Hierarchical clustering based on NCOR2-350 (subgroup A vs. subgroup B) | 2.71 (1.06-6.96) | 0.038 |
| Age (per 10-yr increment) | 1.60 (1.00-1.01) | 0.037 |
| Tumor size (≧5 cm vs. <5 cm) | 1.71 (0.64-4.54) | 0.284 |
| Tumor grade (≧ grade 3 vs. < grade 3) | 1.23 (0.42-3.63) | 0.71 |
| Positive LN status vs. negative status | 0.37 (0.13-1.05) | 0.061 |
| Positive ER status vs. negative status | 4.46 (1.66-12.01) | 0.003 |
| Positive HER2 vs. negative HER2 | 0.49 (0.18-1.33) | 0.162 |

TABLE 9

Analysis of prognostic methods in a cohort of 130 breast cancer patients.

| Variable | Odds Ratio (95% Confidence Interval) | P value |
|---|---|---|
| $S_{NCOR2-350}$ (higher vs. lower than the cut-of value) | 6.47 (2.36-17.79) | <0.001 |
| Age (per 10-yr increment) | 1.05 (1.0-1.09) | 0.05 |
| Tumor size (≧5 cm vs. <5 cm) | 2.28 (0.8-6.51) | 0.125 |
| Tumor grade (≧ grade 3 vs. < grade 3) | 1.14 (0.37-3.51) | 0.825 |
| Positive LN status vs. negative status | 0.33 (0.11-0.99) | 0.049 |
| Positive ER status vs. negative status | 3.79 (1.37-10.47) | 0.01 |
| Positive HER2 vs. negative HER2 | 0.3 (0.1-0.88) | 0.029 |

Table 10 shows that N-CoR2 expression, hierarchical clustering of 130 breast carcinomas based on NCOR2-350 and $S_{NCOR2-350}$ provide a prognostic measure of resistant tumors with high specificities and positive predictive values and relatively lower negative predictive values. The overall accuracy of prediction made by NCOR-350 is higher than those by the expression level of N-CoR2 or hierarchical clustering classification.

TABLE 10

Analysis of prognostic methods in a cohort of 130 breast cancer patients.

| | Predictor | | |
|---|---|---|---|
| | N—CoR2 | Average Linkage Clustering based on NCOR2-350 | $S_{NCOR2-350}$ |
| Overall accuracy | 58.5 (50.0-66.9)* | 63.8 (55.6-63.8) | 73.8 (66.3-81.4) |
| Sensitivity | 56.2 (49.8-61.9) | 61.8 (55.4-67.2) | 80.9 (74.8-86.3) |
| Specificity | 63.4 (49.5-75.9) | 68.3 (54.5-80.1) | 58.5 (45.3-70.2) |
| Positive predictive value | 76.9 (68.2-84.8) | 80.9 (72.5-88.0) | 80.9 (74.8-86.3) |
| Negative predictive value | 40.0 (31.2-47.9) | 45.2 (36.0-53.0) | 58.5 (45.3-70.2) |

*Data in parenthesis are 95% confidence intervals.

Example 4

This example demonstrates that biomarkers associated with N-CoR2 are prognostic markers for the response to preoperative combinational chemotherapy in breast cancers.

As shown in Example 1 and Table 1, overexpression of N-CoR2 in neoplastic HMT3522 T4-2 breast epithelial cells is associated with significant alterations in the transcription of 304 genes (NCOR2-350) that are involved in diverse biological processes. It's thus likely that breast tumors can be further optimally classified with respect to their response to death stimuli or cytotoxic anti-cancer therapy by a small subset of genes in NCOR2-350. To this end, we used a robust three-step supervised classification method (Nature 415:530-536 (2002)), with some modifications. First, we calculated the correlation between the treatment response categories (i.e., responders or non-responders) and the expression levels (on a $\log_2$ scale) of NCOR2-350 across the 130 breast tumors in the M.D. Anderson Cancer Center data set (J. Clin. Oncol. 24:4236-4244 (2006)) using Pearson's correlation coefficient. We then selected the probe sets with a correlation coefficient greater than 0.2 or less than −0.2, which represent those significantly associated with treatment outcome, and found a list of 93 gene probes that fulfilled this criterion. Second, to identify an optimal set of reporter gene probes with the highest performance, the 93 gene probes are ranked descendingly according to their respective correlation with the treatment response. Starting from the set containing the top 3 probes, we repeatedly added 1 more probe each time from the top of the descendingly ranked probe sets until all of them were used. The resultant 91 sets of reporter probes were then respectively used as classifiers for the prediction of the likelihood of not responding to neoadjuvant chemotherapy whose performances were then estimated in a leave-one-out cross-validation. Specifically, for each of the 91 classifiers, one of the 130 breast tumors was taken out at one time and the average expression levels of the probes in the classifier in the non-responders from the remaining 129 tumor samples were used as an "average non-responder profile (ANP)". Likewise, the average expression levels of the probes in the responders from the remaining 129 tumor samples were used as an "average responder profile (ARP)". The treatment outcome of the left out sample was then predicted according to the respective level of its Person's correlation coefficient with the ANP and the ARP of the remaining 129 samples. The entire cross-validation procedure was repeated 130 times until each of the 130 samples was left out once. Cross-validated performance was assessed by observed accuracy, sensitivity and specificity.

Figure 7:
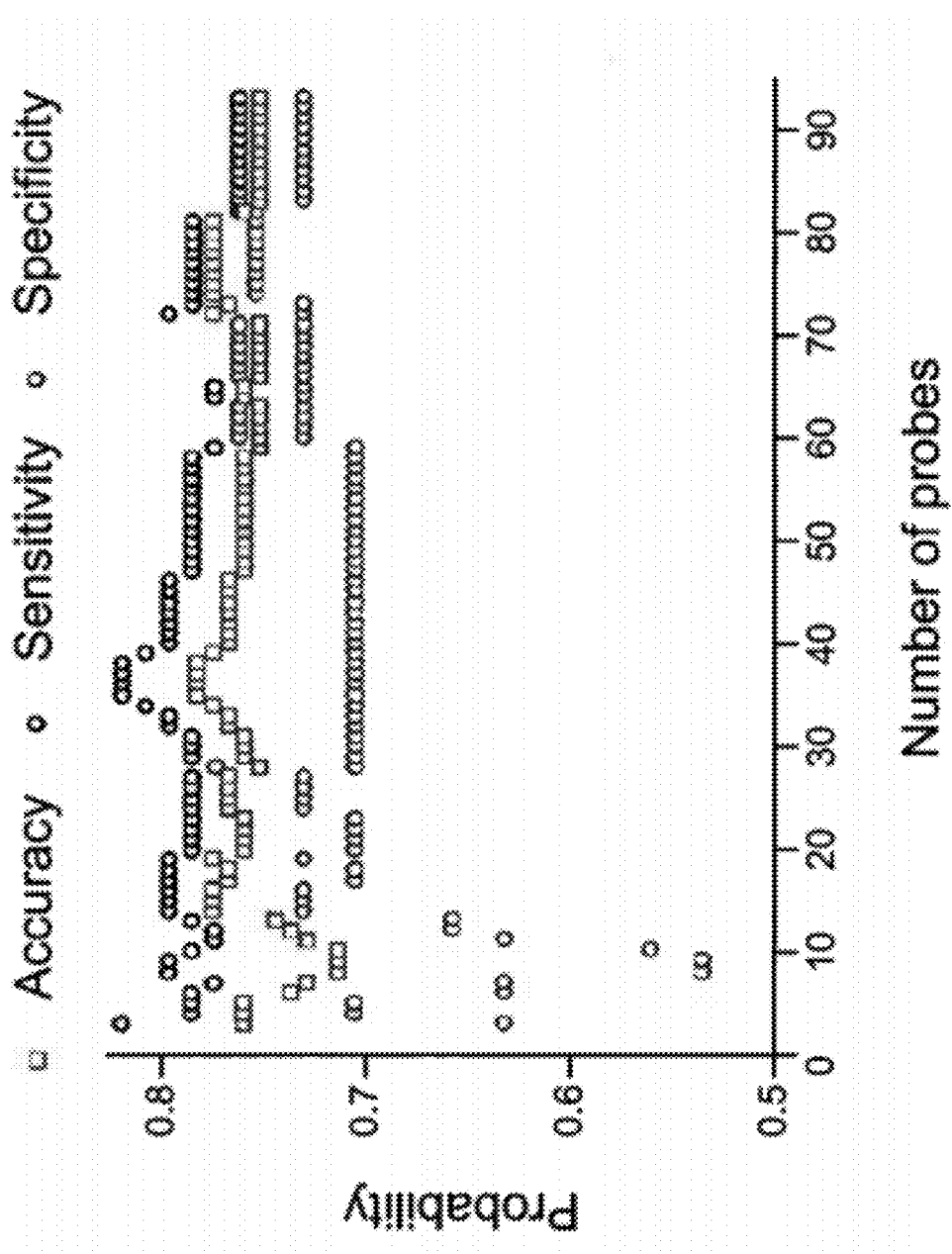
FIG. 7 The accuracy, sensitivity and specificity for the prediction of the likelihood of not responding to neoadjuvant chemotherapy of the 91 classifiers identified from the 93 top ranked genes in NCOR2-350 that correlate with treatment outcome of breast carcinomas in the M.D. Anderson Cancer Center data set (Pearson's correlation coefficient $\geq 0.2$ or $\leq -0.2$). The optimal prediction is reached when a set of 38 top ranked probes are used as a classifier.

As shown in FIG. 7, the prediction reaches its maximum when 38 probes from the top of the ranked probe list were used as the classifier. The 38 probe sets representing 35 genes (Table 11) constitute the best performed N-CoR2-based CT response classifier and is designated hereinafter as "NCOR2-38".

TABLE 11

The 35 genes (38 probe sets) in NCOR2-38. The probe sets are ranked descendingly accordingly to their correlations with the treatment response categories (1, non-responder; 0, responder) of the 130 breast cancers in the M.D. Anderson Cancer Center data set.

| AFFYMETRIX PROBE SET ID | GENE SYMBOL | REFSEQ TRANSCRIPT ID | DESCRIPTION | PEARSON'S CORRELATION COEFFICIENT |
|---|---|---|---|---|
| 203963_at | CA12 | NM_001218/ NM_206925 | carbonic anhydrase XII | 0.4500 |
| 204508_s_at | CA12 | NM_001218/ NM_206925 | carbonic anhydrase XII | 0.4282 |
| 210735_s_at | CA12 | NM_001218/ NM_206925 | carbonic anhydrase XII | 0.4001 |
| 203303_at | DYNLT3 | NM_006520 | dynein, light chain, Tctex-type 3 | 0.3603 |
| 204686_at | IRS1 | NM_005544 | insulin receptor substrate 1 | 0.3528 |
| 209194_at | CETN2 | NM_004344 | centrin, EF-hand protein, 2 | 0.3337 |
| 203453_at | SCNN1A | NM_001038 | sodium channel, nonvoltage-gated 1 alpha | 0.3334 |
| 204343_at | ABCA3 | NM_001089 | ATP-binding cassette, sub-family A (ABC1), member 3 | 0.3334 |
| 202376_at | SERPINA3 | NM_001085 | serpin peptidase inhibitor, clade A (alpha-1 antiproteinase, antitrypsin), member 3 | 0.3171 |
| 202371_at | TCEAL4 | NM_001006935/ NM_001006936/ NM_001006937/ NM_024863 | transcription elongation factor A (SII)-like 4 | 0.3097 |
| 201132_at | HNRPH2 | NM_001032393/ NM_019597 | heterogeneous nuclear ribonucleoprotein H2 (H') | 0.3097 |
| 201150_s_at | TIMP3 | NM_000362 | TIMP metallopeptidase inhibitor 3 | 0.3050 |
| 212510_at | GPD1L | NM_015141 | glycerol-3-phosphate dehydrogenase 1-like | 0.3015 |
| 217202_s_at | GLUL | NM_001033044/ NM_001033056/ NM_002065 | glutamate-ammonia ligase | 0.2976 |
| 204768_s_at | FEN1 | NM_004111 | flap structure-specific endonuclease 1 | −0.2946 |
| 212949_at | BRRN1 | NM_015341 | barren homolog 1 | −0.2977 |
| 204533_at | CXCL10 | NM_001565 | chemokine (C—X—C motif) ligand 10 | −0.2978 |
| 202037_s_at | SFRP1 | NM_003012 | secreted frizzled-related protein 1 | −0.2993 |
| 218009_s_at | PRC1 | NM_003981/ NM_199413/ NM_199414 | protein regulator of cytokinesis 1 | −0.2993 |
| 207719_x_at | CEP170 | NM_014812 | centrosomal protein 170 kDa | −0.3058 |
| 221436_s_at | CDCA3 | NM_031299 | cell division cycle associated 3 | −0.3071 |
| 218755_at | KIF20A | NM_005733 | kinesin family member 20A | −0.3086 |
| 212022_s_at | MKI67 | NM_002417 | antigen identified by monoclonal antibody Ki-67 | −0.3147 |
| 211519_s_at | KIF2C | NM_006845 | kinesin family member 2C | −0.3227 |
| 221004_s_at | ITM2C | NM_001012514/ NM_001012516/ NM_030926 | integral membrane protein 2C | −0.3310 |
| 215253_s_at | DSCR1 | NM_004414/ NM_203417/ NM_203418 | Down syndrome critical region gene 1 | −0.3443 |
| 211122_s_at | CXCL11 | NM_005409 | chemokine (C—X—C motif) ligand 11 | −0.3462 |
| 202870_s_at | CDC20 | NM_001255 | CDC20 cell division cycle 20 homolog | −0.3466 |
| 212190_at | SERPINE2 | NM_006216 | serpin peptidase inhibitor, clade E, member 2 | −0.3493 |
| 204033_at | TRIP13 | NM_004237 | thyroid hormone receptor interactor 13 | −0.3582 |
| 210052_s_at | TPX2 | NM_012112 | TPX2, microtubule-associated, homolog | −0.3800 |
| 209408_at | KIF2C | NM_006845 | kinesin family member 2C | −0.3832 |
| 201755_at | MCM5 | NM_006739 | MCM5 minichromosome maintenance deficient 5 | −0.3866 |
| 204750_s_at | DSC2 | NM_004949/ NM_024422 | desmocollin 2 | −0.3921 |

TABLE 11-continued

The 35 genes (38 probe sets) in NCOR2-38. The probe sets are ranked descendingly accordingly to their correlations with the treatment response categories (1, nonresponder; 0, responder) of the 130 breast cancers in the M.D. Anderson Cancer Center data set.

| AFFYMETRIX PROBE SET ID | GENE SYMBOL | REFSEQ TRANSCRIPT ID | DESCRIPTION | PEARSON'S CORRELATION COEFFICIENT |
| --- | --- | --- | --- | --- |
| 204962_s_at | CENPA | NM_001809 | centromere protein A, 17 kDa | −0.4233 |
| 202240_at | PLK1 | NM_005030 | polo-like kinase 1 | −0.4274 |
| 201555_at | MCM3 | NM_002388 | MCM3 minichromosome maintenance deficient 3 | −0.4331 |
| 218726_at | HJURP | NM_018410 | Holliday junction recognition protein | −0.4346 |

To predict the chemotherapy responsiveness of the 130 breast tumor using NCOR2-38, we calculated the Pearson's correlation coefficient of expression of the 38 gene probes between the left out breast tumor and the ANP of the remaining tumor samples (designated as "$r_{ANP}$"). A cut-off value of 0.7528, which yielded a lowest rate of type 1 and type 2 errors, was determined using the area under the receiver operating characteristic (ROC) curve (J. Natl. Cancer Inst. 95:511-515 (2003)).

Figure 8:
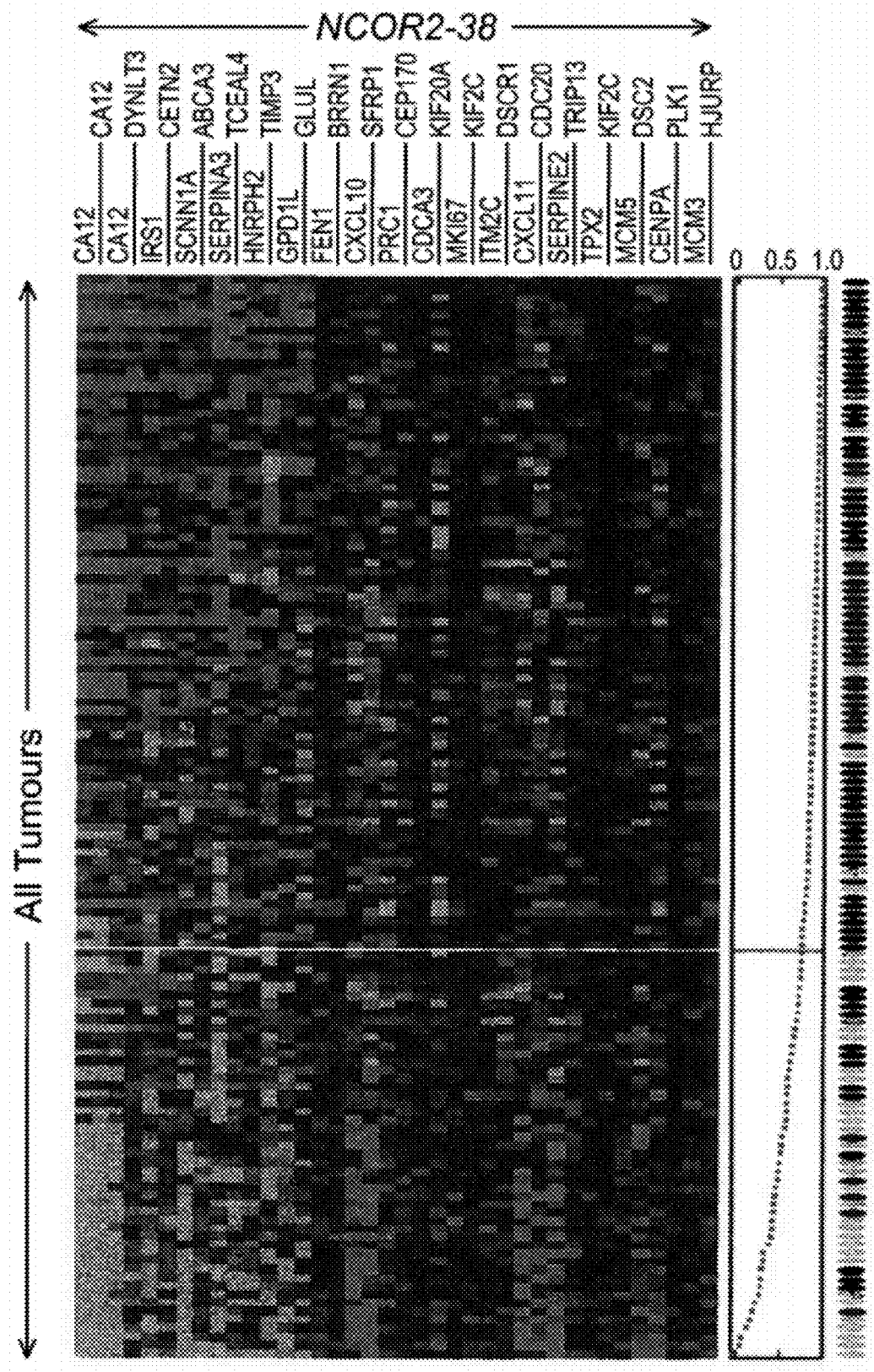
FIG. 8 The expression profile of the gene probes in NCOR2-38 from the 130 breast tumors in the M.D. Anderson Cancer Center data set. The tumors are ranked descendingly according to $r_{ANP}$ (right panel) and those with correlation coefficients higher than a cut-off value (solid line) is assigned to the non-responder group while that with a correlation coefficient lower than the cut-off value is assigned to the responder group. Yellow circles, responders; black circles, non-responders.

FIG. 8 shows the expression profile of the gene probes in NCOR2-38 from the 130 breast tumors in the M.D. Anderson Cancer Center data set. The tumors are ranked according to $r_{ANP}$ and those with correlation coefficients higher than said cut-off value is assigned to the non-responder group while that with a correlation coefficient lower than the cut-off value is assigned to the responder group.

The absence of estrogen receptor (ER) is associated with high response rates to neoadjuvant chemotherapy for breast cancer. Consistently, using a logistic regression model including all available clinical variables in the M.D. Anderson Cancer Center data set, the presence of ER is the strongest and independent predictor of the likelihood of not responding to NACT with an odds ratio of 5.6 (P<0.001). To further verify that N-CoR2-associated transcriptional activity is associated with NACT responsiveness independently of the ER status, we applied the above mentioned multi-step classification procedure to the transcriptome of a subgroup of 80 ER-positive tumors in the data set and thereby identified a 42-probe set best performed multi-gene classifier, designated as "NCOR2-42", for the prediction of the likelihood of CT resistance in this subgroup of tumors. Likewise, we identified another 45-probe set classifier (designated as "NCOR2-45") that best predicts poor response to neoadjuvant chemotherapy in a subgroup of 50 ER-negative tumors.

Table 12 and Table 13 shows the identity of the 41 genes (42 probe sets) and the 40 genes (45 probe sets) in NCOR2-42 and NCOR2-45, respectively.

TABLE 12

The 41 genes (42 probe sets) in NCOR2-42. The probe sets are ranked descendingly accordingly to their correlations with the treatment response categories (1, nonresponder; 0, responder) of the 80 ER-positive breast tumors in the M.D. Anderson Cancer Center data set.

| AFFYMETRIX PROBE SET ID | GENE SYMBOL | REFSEQ TRANSCRIPT ID | DESCRIPTION | PEARSON'S CORRELATION COEFFICIENT |
| --- | --- | --- | --- | --- |
| 202240_at | PLK1 | NM_005030 | polo-like kinase 1 | 0.4211 |
| 201555_at | MCM3 | NM_002388 | minichromosome maintenance deficient 3 | 0.4021 |
| 212531_at | LCN2 | NM_005564 | lipocalin 2 | 0.3909 |
| 212022_s_at | MKI67 | NM_002417 | antigen identified by monoclonal antibody Ki-67 | 0.3901 |
| 204962_s_at | CENPA | NM_001809 | centromere protein A | 0.3888 |
| 215942_s_at | GTSE1 | NM_016426 | G-2 and S-phase expressed 1 | 0.3782 |
| 218726_at | HJURP | NM_018410 | Holliday junction recognition protein | 0.3516 |
| 209408_at | KIF2C | NM_006845 | kinesin family member 2C | 0.3283 |
| 209136_s_at | USP10 | NM_005153 | ubiquitin specific peptidase 10 | 0.3228 |
| 204768_s_at | FEN1 | NM_004111 | flap structure specific endonuclease 1 | 0.3195 |
| 218365_s_at | DARS2 | NM_018122 | aspartyl-tRNA synthetase 2 | 0.3137 |
| 203976_s_at | CHAF1A | NM_005483 | chromatin assembly factor 1, subunit A | 0.2989 |
| 210052_s_at | TPX2 | NM_012112 | microtubule associated, homolog | 0.2949 |
| 211519_s_at | KIF2C | NM_006845 | kinesin family member 2C | 0.2937 |
| 218009_s_at | PRC1 | NM_003981/ NM_199413/ NM_199414 | protein regulator of cytokinesis 1 | 0.2827 |
| 203798_s_at | VSNL1 | NM_003385 | visinin-like 1 | 0.2811 |
| 202954_at | UBE2C | NM_007019/ NM_181799/ | ubiquitin-conjugating enzyme E2C | 0.2809 |

TABLE 12-continued

The 41 genes (42 probe sets) in NCOR2-42. The probe sets are ranked descendingly accordingly to their correlations with the treatment response categories (1, nonresponder; 0, responder) of the 80 ER-positive breast tumors in the M.D. Anderson Cancer Center data set.

| AFFYMETRIX PROBE SET ID | GENE SYMBOL | REFSEQ TRANSCRIPT ID | DESCRIPTION | PEARSON'S CORRELATION COEFFICIENT |
| --- | --- | --- | --- | --- |
| 201774_s_at | CNAP1 | NM_181800/ NM_181801/ NM_181802/ NM_181803 NM_014865 | chromosome condensation-related SMC-associated protein 1 | 0.2781 |
| 204033_at | TRIP13 | NM_004237 | thyroid hormone receptor interactor 13 | 0.2772 |
| 221436_s_at | CDCA3 | NM_031299 | cell division cycle associated 3 | 0.2766 |
| 218755_at | KIF20A | NM_005733 | kinesin family member 20A | 0.2757 |
| 202870_s_at | CDC20 | NM_001255 | cell division cycle 20 homolog | 0.2750 |
| 204750_s_at | DSC2 | NM_004949/ NM_024422 | desmocollin 2 | 0.2747 |
| 203145_at | SPAG5 | NM_006461 | sperm associated antigen 5 | 0.2637 |
| 219010_at | C1orf106 | NM_018265 | chromosome 1 open reading frame 106 | 0.2563 |
| 202095_s_at | BIRC5 | NM_001012270/ NM_001012271/ NM_001168 | baculoviral IAP repeat-containing 5 | 0.2459 |
| 203967_at | CDC6 | NM_001254 | cell division cycle 6 homolog | 0.2453 |
| 201755_at | MCM5 | NM_006739 | minichromosome maintenance deficient 5 | 0.2403 |
| 214710_s_at | CCNB1 | NM_031966 | cyclin B1 | 0.2292 |
| 217010_s_at | CDC25C | NM_001790/ NM_022809 | cell division cycle 25C | 0.2250 |
| 214336_s_at | COPA | NM_004371 | coatomer protein complex, subunit alpha | 0.2214 |
| 200994_at | IPO7 | NM_006391 | Importin 7 | −0.2171 |
| 209028_s_at | ABI1 | NM_001012750/ NM_001012751/ NM_001012752/ NM_005470 | abl-interactor 1 | −0.2251 |
| 209194_at | CETN2 | NM_004344 | centrin, EF-hand protein, 2 | −0.2401 |
| 209115_at | UBE1C | NM_003968/ NM_198195/ NM_198197 | ubiquitin-activating enzyme E1C | −0.2434 |
| 200900_s_at | M6PR | NM_002355 | mannose-6-phosphate receptor | −0.2464 |
| 203303_at | DYNLT3 | NM_006520 | dynein, light chain, Tctex-type 3 | −0.2498 |
| 210756_s_at | NOTCH2 | NM_024408 | Notch homolog 2 | −0.2548 |
| 213229_at | DICER1 | NM_030621/ NM_177438 | Dicer1 | −0.2656 |
| 202378_s_at | LEPROT | NM_017526 | leptin receptor overlapping transcript | −0.2664 |
| 203963_at | CA12 | NM_001218/ NM_206925 | carbonic anhydrase XII | −0.2699 |
| 201132_at | HNRPH2 | NM_001032393/ NM_019597 | heterogeneous nuclear ribonucleoprotein H2 | −0.2934 |

TABLE 13

The 40 genes (45 probe sets) in NCOR2-45. The probe sets are ranked descendingly accordingly to their correlations with the treatment response categories (1, nonresponder; 0, responder) of the 50 ER-negative breast tumors in the M.D. Anderson Cancer Center data set.

| AFFYMETRIX PROBE SET ID | GENE SYMBOL | REF SEQ TRANSCRIPT ID | DESCRIPTION | PEARSON'S CORRELATION COEFFICIENT |
| --- | --- | --- | --- | --- |
| 201801_s_at | SLC29A1 | NM_004955 | solute carrier family 29, member 1 | 0.4428 |
| 201555_at | MCM3 | NM_002388 | minichromosome maintenance deficient 3 | 0.3258 |

TABLE 13-continued

The 40 genes (45 probe sets) in NCOR2-45. The probe sets are ranked descendingly accordingly to their correlations with the treatment response categories (1, nonresponder; 0, responder) of the 50 ER-negative breast tumors in the M.D. Anderson Cancer Center data set.

| AFFYMETRIX PROBE SET ID | GENE SYMBOL | REF SEQ TRANSCRIPT ID | DESCRIPTION | PEARSON'S CORRELATION COEFFICIENT |
|---|---|---|---|---|
| 215253_s_at | DSCR1 | NM_004414/ NM_203417/ NM_203418 | Down syndrome critical region gene 1 | 0.3211 |
| 212372_at | MYH10 | NM_005964 | myosin, heavy polypeptide 10 | 0.3195 |
| 205097_at | SLC26A2 | NM_000112 | solute carrier family 26, member 2 | 0.3029 |
| 221931_s_at | SEH1L | NM_001013437/ NM_031216 | SEH1-like | 0.2873 |
| 218726_at | HJURP | NM_018410 | Holliday junction recognition protein | 0.2703 |
| 213135_at | TIAM1 | NM_003253 | T-cell lymphoma invasion and metastasis 1 | 0.2584 |
| 208351_s_at | MAPK1 | NM_002745/ NM_138957 | mitogen-activated protein kinase 1 | 0.2508 |
| 58916_at | KCTD14 | NM_023930 | potassium channel tetramerisation domain containing 14 | 0.2503 |
| 201755_at | MCM5 | NM_006739 | minichromosome maintenance deficient 5 | 0.2463 |
| 201830_s_at | NET1 | NM_005863 | neuroepithelial cell transforming gene 1 | 0.2460 |
| 207719_x_at | CEP170 | NM_014812 | centrosomal protein 170 kDa | 0.2454 |
| 214686_at | ZNF266 | NM_006631/ NM_198058 | zinc finger protein 266 | 0.2446 |
| 203247_s_at | ZNF24 | NM_006965 | zinc finger protein 24 | 0.2374 |
| 210052_s_at | TPX2 | NM_012112 | microtubule associated, homolog | 0.2373 |
| 210136_at | MBP | NM_001025081/ NM_001025090/ NM_001025092/ NM_001025094/ NM_001025098/ NM_001025100/ NM_001025101/ NM_002385 | myelin basic protein | 0.2366 |
| 215177_s_at | ITGA6 | NM_000210 | integrin, alpha 6 | 0.2361 |
| 221568_s_at | LIN7C | NM_018362 | lin-7 homolog C | 0.2322 |
| 202037_s_at | SFRP1 | NM_003012 | secreted frizzled-related protein 1 | 0.2311 |
| 212605_s_at | | | | 0.2296 |
| 221029_s_at | WNT5B | NM_030775/ NM_032642 | wingless-type MMTV integration site family, member 5B | −0.2338 |
| 204508_s_at | CA12 | NM_001218/ NM_206925 | carbonic anhydrase XII | −0.2349 |
| 204351_at | S100P | NM_005980 | S100 calcium binding protein P | −0.2355 |
| 217739_s_at | PBEF1 | NM_005746/ NM_182790/ XM_929247 | pre-B-cell colony enhancing factor 1 | −0.2355 |
| 38037_at | HBEGF | NM_001945 | heparin-binding EGF-like growth factor | −0.2439 |
| 202376_at | SERPINA3 | NM_001085 | serpin peptidase inhibitor, clade A, member 3 | −0.2484 |
| 205709_s_at | CDS1 | NM_001263 | CDP-diacylglycerol synthase 1 | −0.2524 |
| 205767_at | EREG | NM_001432 | epiregulin | −0.2558 |
| 203780_at | EVA1 | NM_005797/ NM_144765 | epithelial V-like antigen 1 | −0.2622 |
| 203453_at | SCNN1A | NM_001038 | sodium channel, nonvoltage-gated 1 alpha | −0.2659 |
| 209098_s_at | JAG1 | NM_000214 | jagged 1 | −0.2662 |
| 201888_s_at | IL13RA1 | NM_001560 | interleukin 13 receptor, alpha 1 | −0.2670 |
| 217202_s_at | GLUL | NM_001033044/ NM_001033056/ NM_002065 | glutamate-ammonia ligase | −0.2689 |
| 201887_at | IL13RA1 | NM_001560 | interleukin 13 receptor, alpha 1 | −0.2748 |

TABLE 13-continued

The 40 genes (45 probe sets) in NCOR2-45. The probe sets are ranked descendingly accordingly to their correlations with the treatment response categories (1, nonresponder; 0, responder) of the 50 ER-negative breast tumors in the M.D. Anderson Cancer Center data set.

| AFFYMETRIX PROBE SET ID | GENE SYMBOL | REF SEQ TRANSCRIPT ID | DESCRIPTION | PEARSON'S CORRELATION COEFFICIENT |
|---|---|---|---|---|
| 210663_s_at | KYNU | NM_001032998/ NM_003937 | Kynureninase | −0.3118 |
| 202351_at | ITGAV | NM_002210 | integrin, alpha V | −0.3184 |
| 203925_at | GCLM | NM_002061 | glutamate cysteine ligase, modifier subunit | −0.3202 |
| 205623_at | ALDH3A1 | NM_000691 | aldehyde dehydrogenase 3 family, memberA1 | −0.3265 |
| 209624_s_at | MCCC2 | NM_022132 | methylcrotonoyl-Coenzyme A carboxylase 2 | −0.3294 |
| 217388_s_at | KYNU | NM_001032998/ NM_003937 | Kynureninase | −0.3325 |
| 38043_at | FAM3A | NM_021806 | family with sequence similarity 3, member A | −0.3397 |
| 211612_s_at | IL13RA1 | NM_001560 | interleukin 13 receptor, alpha 1 | −0.3613 |
| 202435_s_at | CYP1B1 | NM_000104 | cytochrome P450, family 1, subfamily B, polypeptide 1 | −0.3668 |
| 202437_s_at | CYP1B1 | NM_000104 | cytochrome P450, family 1, subfamily B, polypeptide 1 | −0.3800 |

FIG. 9 shows the expression profile of the gene probes in NCOR2-42 from the 80 ER-positive breast tumors and the gene probes in NCOR2-45 from the 50 ER-negative breast tumors in the M.D. Anderson Cancer Center data set. In each subset, the tumors are ranked according to $r_{ANP}$ and a cut-off value that yields a lowest rate of type 1 and type 2 errors is determined using the area under the ROC curve. The tumors with correlation coefficients higher than said cut-off value is assigned to the non-responder group while that with a correlation coefficient lower than the cut-off value is assigned to the responder group.

Table 14 shows the results of logistic regression models including standard clinicopathological variables and N-CoR2-based multigene classifiers (NCOR2-38, NCOR2-42 or NCOR2-45) for the prediction of the likelihood of unresponding to neoadjuvant chemotherapy in the 130 breast tumors in the M.D. Anderson Cancer Center data set. Compared with clinicopathological variables including the ER status, tumor stratification by the cut-off value of $r_{ANP}$ calculated based on NCOR2-38 is the only independent treatment predictor (odds ratio 8.5, P<0.001) for all the 130 tumors. Similarly, tumor stratification based on NCOR2-42 or NCOR2-45 is the only independent predictor for treatment response in ER-positive or ER-negative tumors, respectively. These results lend strong support to the essential role of the N-CoR2-related transcription activity in the chemotherapy responsiveness of breast cancer in humans.

TABLE 14

Multivariate analysis for the likelihood of not responding to pre-operative CT according to N—CoR2-related multigene classifiers and clinicopathological variables

| VARIABLE | ODDS RATIO (95% CI) | P VALUE |
|---|---|---|
| All tumors | | |
| Higher vs. lower $r_{ANP}$ | 8.5 (2.7-26.7) | <0.001 |
| Age (per 10-yr increment) | 1.0 (1.0-1.1) | 0.08 |
| Tumor size (≧5 cm vs. <5 cm) | 0.6 (0.2-1.6) | 0.268 |
| Tumor grade (≧ grade 3 vs. < grade 3) | 0.6 (0.2-2.1) | 0.456 |
| Positive LN status vs. negative status | 2.1 (0.7-6.1) | 0.193 |
| Positive ER status vs. negative status | 0.5 (0.2-1.6) | 0.25 |
| Positive HER2 vs. negative HER2 | 2.5 (0.8-7.3) | 0.104 |
| ER-positive | | |
| Higher vs. lower $r_{ANP}$ | 15.6 (3.1-79.9) | <0.001 |
| Age (per 10-yr increment) | 1.1 (1.0-1.1) | 0.155 |
| Tumor size (≧5 cm vs. <5 cm) | 1.5 (0.3-6.2) | 0.61 |
| Tumor grade (≧ grade 3 vs. < grade 3) | 0.4 (0.1-2.0) | 0.264 |
| Positive LN status vs. negative status | 3.4 (0.7-17.0) | 0.133 |
| Positive HER2 vs. negative HER2 | 2.5 (0.4-14.3) | 0.3 |
| ER-negative | | |
| Higher vs. lower $r_{ANP}$ | 6.6 (1.4-29.7) | 0.015 |
| Age (per 10-yr increment) | 1.1 (1.0-1.2) | 0.054 |
| Tumor size (≧5 cm vs. <5 cm) | 0.2 (0.0-1.1) | 0.069 |
| Tumor grade (≧ grade 3 vs. < grade 3) | 2.4 (0.3-19.5) | 0.409 |
| Positive LN status vs. negative status | 5.0 (0.7-34.5) | 0.101 |
| Positive HER2 vs. negative HER2 | 2.4 (0.5-10.8) | 0.257 |

The analysis included the 130 patients with breast cancer, including 80 ER+ and 50 ER− tumors, in the M.D. Anderson Cancer Center data set. The tumors were segregated into subgroups according to a cut-off value of rANP determined based on NCOR2-38 (for all tumors), NCOR2-42 (for ER-positive tumors) or NCOR2-45 (for ER-negative tumors) or clinicopathological variables. Age was modeled as a continuous variable. CI denotes 95% confidence interval.

NCOR2-38 represents a set of N-CoR2-associated genes that optimally classifies breast tumors according to their responsiveness to death stimuli or cytotoxic anti-cancer therapy. To further verify that NCOR2-38 defines the relationship between N-CoR2-associated transcriptional activities and chemotherapy responsiveness of human breast carcinomas, we normalize and median-center the average expression levels (on a $\log_2$ scale) of NCOR2-38 in T4-2-N-CoR2 cells, the vector control cells and the 130 breast tumors in the M.D. Anderson Cancer Center data set (J. Clin. Oncol. 24:4236-4244 (2006)). We then measure the degree of resemblance between the expression profiles of NCOR2-38 in the 130 breast tumors and those in T4-2 N-CoR2 cells or the vector control cells using Pearson's correlation coefficient, which yields $r_{NCOR2}$ and $r_{vector}$, respectively. Similar to Equation 1 in Example 3, a NCOR2-38-based N-CoR2 transcription activity similarity score "$S_{NCOR2-38}$" is used to represent the similarity between the transcriptional profile of genes in NCOR2-38 between T4-2-N-CoR2 cells and those of the breast tumors, $$S_{NCOR2-38} = r_{NCOR2} - r_{vector} \quad \text{(Equation 2)}$$

Similar similarity algorithms are used to calculate $S_{NCOR2-42}$ and $S_{NCOR2-45}$, which respectively represent the similarity between the transcriptional profiles of genes in NCOR2-42 or NCOR2-45 and those of the ER-positive or ER-negative breast tumors.

Figure 10:
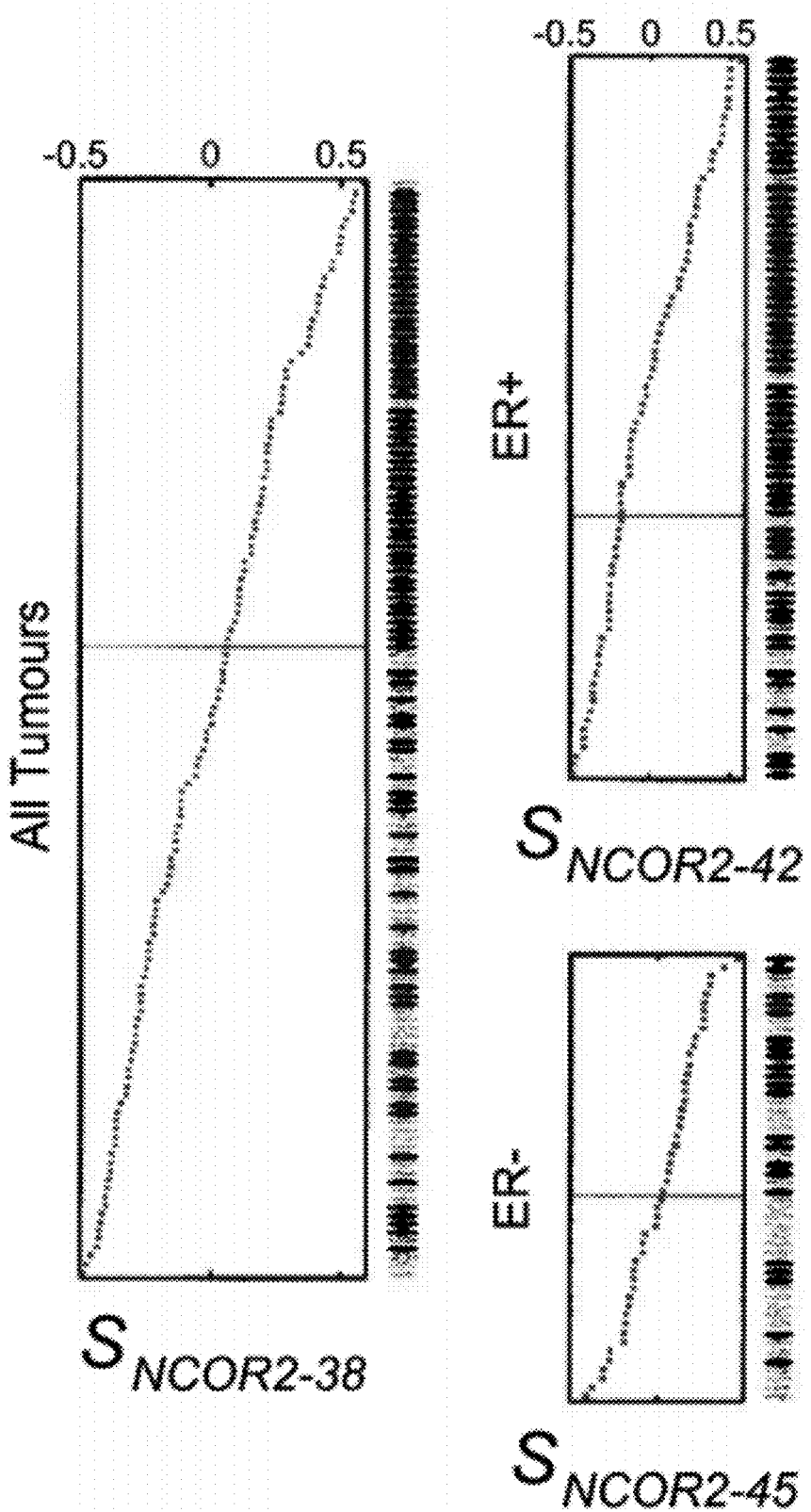
FIG. 10 Classification of the breast carcinomas of the M.D. Anderson Cancer Center data set into treatment response groups using N-CoR2-related genomic classifiers optimized for each tumor subsets. Shown in the left panel is the distribution of $S_{NCOR2-38}$ among the 130 breast carcinomas. Shown in the right panels are the distributions of $S_{NCOR2-42}$ and $S_{NCOR2-45}$ among the 80 ER-positive and the 50 ER-negative breast carcinomas, respectively. The solid lines represent the cut-off values of each classifier that best discriminate among nonresponders (black circles) and responders (yellow circles) as determined by the areas under the ROC curves.

In FIG. 10, $S_{NCOR2-38}$ is used as a measure of the transcriptional activities of the genes of NCOR2-38 in breast cancer cells. The 130 patient breast tumors in the M.D. Anderson Cancer Center data set are sorted descendingly according to their respective $S_{NCOR2-38}$ and a cut-off value of 0.0547 (red line) is determined to best discriminate among nonresponders (represented by black circles) and responders (represented by yellow circles) to pre-operative chemotherapy using the area under the ROC curve (left panel). Likewise, the 80 ER-positive tumors and the 50 ER-negative tumors are classified based on optimized cut-off values of $S_{NCOR2-42}$ or $S_{NCOR2-45}$, respectively (right panels).

As shown in Table 15, the likelihood of unresponding to neoadjuvant CT of the 130 breast cancer patients of the M.D. Anderson Cancer Center data set was analyzed using a logistic regression model including $S_{NCOR2-38}$, age, tumor size, nuclear grade, LN, ER and HER2 status as predictors. Compared with standard clinicopathological variables of breast cancer, $S_{NCOR2-38}$ provides the strongest prognostic measure of the likelihood of unresponsiveness to pre-operative CT (Odds ratio 21.35; P<0.001). Similar logistic regression models including $S_{NCOR2-42}$ or $S_{NCOR2-45}$ and standard clinicopathological variables of breast cancer reveal that both N-CoR2-related genomic classifiers are the strongest predictors of the likelihood of unresponding to pre-operative CT in the 80 ER-positive and the 50 ER-negative breast tumors, respectively.

TABLE 15

Multivariate analysis for the likelihood of unresponding to pre-operative CT according to $S_{NCOR2}$ and clinicopathological variables

| VARIABLE | ODDS RATIO (95% CI) | P VALUE |
|---|---|---|
| All (n = 130) | | |
| High $S_{NCOR2}$ vs. low $S_{NCOR2}$ | 21.35 (4.42-103.11) | <0.001 |
| Age (per 10-yr increment) | 1.06 (1.0-1.11) | 0.027 |
| Tumor size (≧5 cm vs. <5 cm) | 1.86 (0.66-5.23) | 0.243 |
| Tumor grade (≧ grade 3 vs. < grade 3) | 1.15 (0.35-3.75) | 0.818 |
| Positive LN status vs. negative status | 0.56 (0.18-1.77) | 0.326 |
| Positive ER status vs. negative status | 2.81 (0.97-8.1) | 0.056 |
| Positive HER2 vs. negative HER2 | 0.68 (0.23-1.96) | 0.471 |
| ER+ (n = 80) | | |
| High $S_{NCOR2}$ vs. low $S_{NCOR2}$ | 25.38 (3.90-164.97) | 0.001 |
| Age (per 10-yr increment) | 1.02 (0.96-1.09) | 0.496 |
| Tumor size (≧5 cm vs. <5 cm) | 0.37 (0.08-1.78) | 0.216 |
| Tumor grade (≧ grade 3 vs. < grade 3) | 1.99 (0.44-9.10) | 0.376 |
| Positive LN status vs. negative status | 0.23 (0.04-1.35) | 0.103 |
| Positive HER2 vs. negative HER2 | 0.19 (0.03-1.15) | 0.07 |
| ER− (n = 50) | | |
| High $S_{NCOR2}$ vs. low $S_{NCOR2}$ | 16.67 (2.44-114.14) | 0.004 |
| Age (per 10-yr increment) | 1.06 (0.98-1.16) | 0.149 |
| Tumor size (≧5 cm vs. <5 cm) | 9.21 (1.38-61.47) | 0.022 |
| Tumor grade (≧ grade 3 vs. < grade 3) | 0.84 (0.06-11.03) | 0.894 |
| Positive LN status vs. negative status | 0.22 (0.03-1.65) | 0.141 |
| Positive HER2 vs. negative HER2 | 0.20 (0.03-1.26) | 0.086 |

The analysis included the 130 patients with breast cancers who received NACT in the MDACC data set. Age was modeled as a continuous variable. CI denotes 95% confidence interval.

Figure 11:
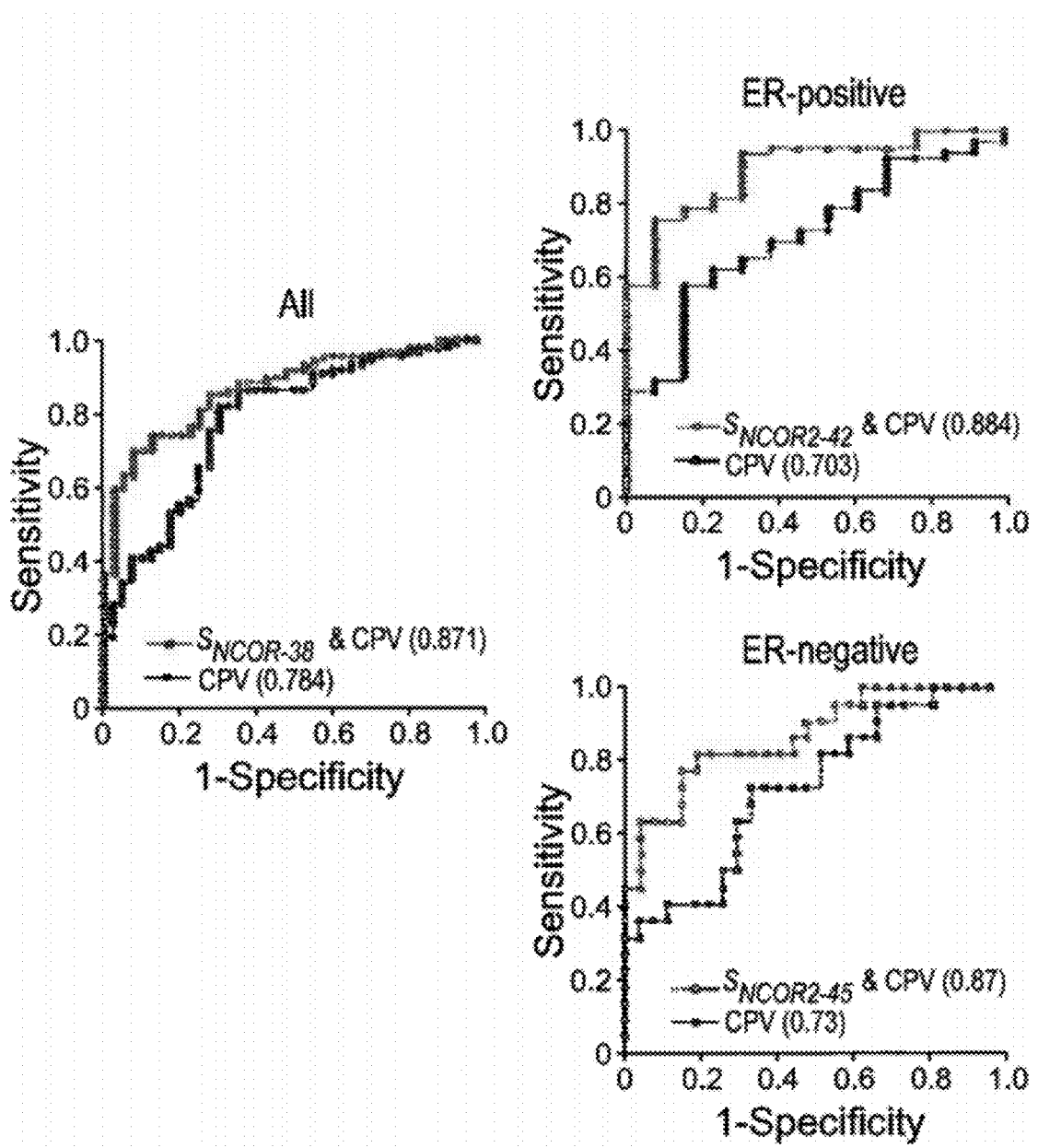
FIG. 11 The ROC curves of the prediction of poor response to pre-operative CT by models based on clinicopathological variables (CPV) or a combination of clinicopathological variables and $S_{NCOR-38}$ (for all tumors in the M.D. Anderson data set), $S_{NCOR2-42}$ (for ER positive tumors) or $S_{NCOR2-45}$ (for ER-negative tumors). Area under each curve is shown in parentheses. The P values indicate the statistical significance of the differences in the correlated areas under the ROC curves of different models using a non-parametric bootstrapping method applied on 1000 bootstrap samples.

FIG. 11 shows the ROC curves of the prediction of poor response to pre-operative CT by models based on clinicopathological variables or a combination of clinicopathological variables and $S_{NCOR-38}$ (for all tumors in the M.D. Anderson data set), $S_{NCOR2-42}$ (for ER-positive tumors) or $S_{NCOR2-45}$ (for ER-negative tumors). The performances of different models were compared using the correlated areas under the ROC curves and statistical significance was tested using a non-parametric bootstrapping method applied on 1000 bootstrap samples (Biometrics 44:837-845 (1988)). Inclusion of N-CoR2-based treatment outcome classifiers in the multivariate models markedly (p<0.05) increased the prediction accuracy, as measured by the areas under the ROC curves (parenthesis), compared with the model using clinicopathological variables alone.

Example 5

This example demonstrates an increase in the sensitivity of breast cancer cells to death stimuli and anti-cancer therapy by downregulation of N-CoR2 or HDAC3.

In order to investigate whether N-CoR2 and/or HDAC3 contribute to the resistance to death stimuli in breast epithelial cells and to determine if these cells can be sensitized by reducing N-CoR2 and/or HDAC3 expression, retroviral-mediated RNA interference (RNAi) was employed to stably downregulate N-CoR2 or HDAC3 expression in breast epithelial cells using siRNA oligonucleotide sequences (5'-AAGGGTATCATCACCGCTGTG-3' (SEQ ID NO:1) for N-CoR2 and 5'-AAGATGCTGAACCATGCACCT-3' (SEQ ID NO:2) for HDAC3) (Mol. Cell. Biol. 23:5122-5131 (2003)). The oligonucleotides specifying the small hairpin RNAs (shRNAs) were subcloned from pSilencer-H1 into pLZRS-MFG-CMV-Neo-U6, a recombinant self-inactivating retroviral vector constructed from the backbone of an MFG provirus (Proc. Natl. Acad. Sci. USA 85:6460-6464 (1988); Proc. Natl. Acad. Sci. USA 90:3539-3543 (1993)), which directs the expression of shRNA under the control of the U6 promoter. Amphotropic retrovirus was produced in Phoenix ampho cells (provided by Professor G. Nolan, Stanford Medical Center) with packaging vectors pCgp and pVSVG to boost viral titer. S1 cells or T4-2 cells, maintained in monolayer cultures, were then spin infected with retrovirus carrying the various RNAi constructs and infected cell populations were selected using 300 μg/ml G418 (Invitrogen). The effect of shRNA-dependent knockdown of N-CoR2 or HDAC3 expressions was verified by real-time PCR (RT-PCR) and immunoblotting.

Non-neoplastic HMT3522 S1 breast epithelial cells or neoplastic HMT3522 T4-2 cells were embedded (8.5×10⁵/ml) within reconstituted basement membrane (rBM) gel (Matrigel, BD Biosciences) in chamber slides (Lab-Tek chamber slides, Nunc) according to the procedures described in U.S. Pat. No. 6,123,941 and Nat. Method. 4:359-365 (2007). The three dimensional cultures were maintained for 12 days before induction of cell death. Phenotypic reversion of HMT3522 T4-2 cells in three dimensional rBM cultures was performed using an epidermal growth factor receptor (EGFR) specific tyrosine kinase inhibitor tyrphostin AG 1478 (100 nM) (Calbiochem), as previously described (Proc. Natl. Acad. Sci. USA 95:14821-14826 (1998))

Apoptotic cell death of the breast epithelial cells cultured in three dimensional rBM was initiated by treatment with recombinant, purified human tumor necrosis factor-related apoptosis-inducing ligand (TRAIL) peptides (BIOMOL) or Paclitaxel (Sigma-Aldrich) as described (Cancer Cell 2:205-216 (2002)). DNA damage-induced cell death was initiated by ionizing radiation (IR) using a Mark I Cesium 137 irradiator (JL Shepherd & Associates).

Percent cell death induced by TRAIL or Paclitaxel was quantified using detection of active caspase 3 (Cell Signaling) by indirect immunofluorescence as described (J. Cell Biol. 163:1397-1407 (2003)). Percent cell death induced by IR was quantified using Live/Dead Viability/Cytotoxicity Assay (Molecular Probes). For both methods, cells were counterstained with 4',6-diamidino-2-phenylindole (DAPI) to label cell nuclei present at different focal planes in the 3D architectures. Percent death was calculated as cells positive for ethidium bromide or active caspase 3 expressed as a percentage of the total number of cells scored by the nuclear staining.

For the comparison of cell growth rates, cells were seeded on culture plastics and the cell number was determined at indicated time points. Population doublings were calculated as ln (cell number at day n/cell number at day 0)/ln 2. Data were shown as mean±SEM of triplicate experiments.

To compare the three dimensional acinar morphogenetic capacity of breast epithelial cells, HTM3522 S1 cells stably transfected with N-CoR2 shRNA or control shRNA were grown in 3D rBM as described above for 10 days. To illustrate the basal surfaces and the intercellular junctions of the polarized acinar structures, the cultures were directly fixed with 2% paraformaldehyde and then incubated with primary antibodies toward β4-integrin and β-catenin, followed by FITC-(green) or Texas red-(red) conjugated secondary antibodies, respectively. Phase contrast images or immunofluorescence images were taken using a scanning confocal laser (model 2000-MP, Bio-Rad Laboratories) attached to a fluorescence microscope (model Eclipse TE-300, Nikon).

For immunoblot analysis, cell colonies (S1 acini or T4-2 cellular aggregates) in 3D rBM were isolated using ice-cold PBS/EDTA. Total cell lysates from monolayered cells or isolated colonies were prepared in Laemmli lysing buffer containing protease inhibitors and immunoblot analysis was performed as described (Exp. Cell Res. 298:122-132 (2004)).

Figure 13:
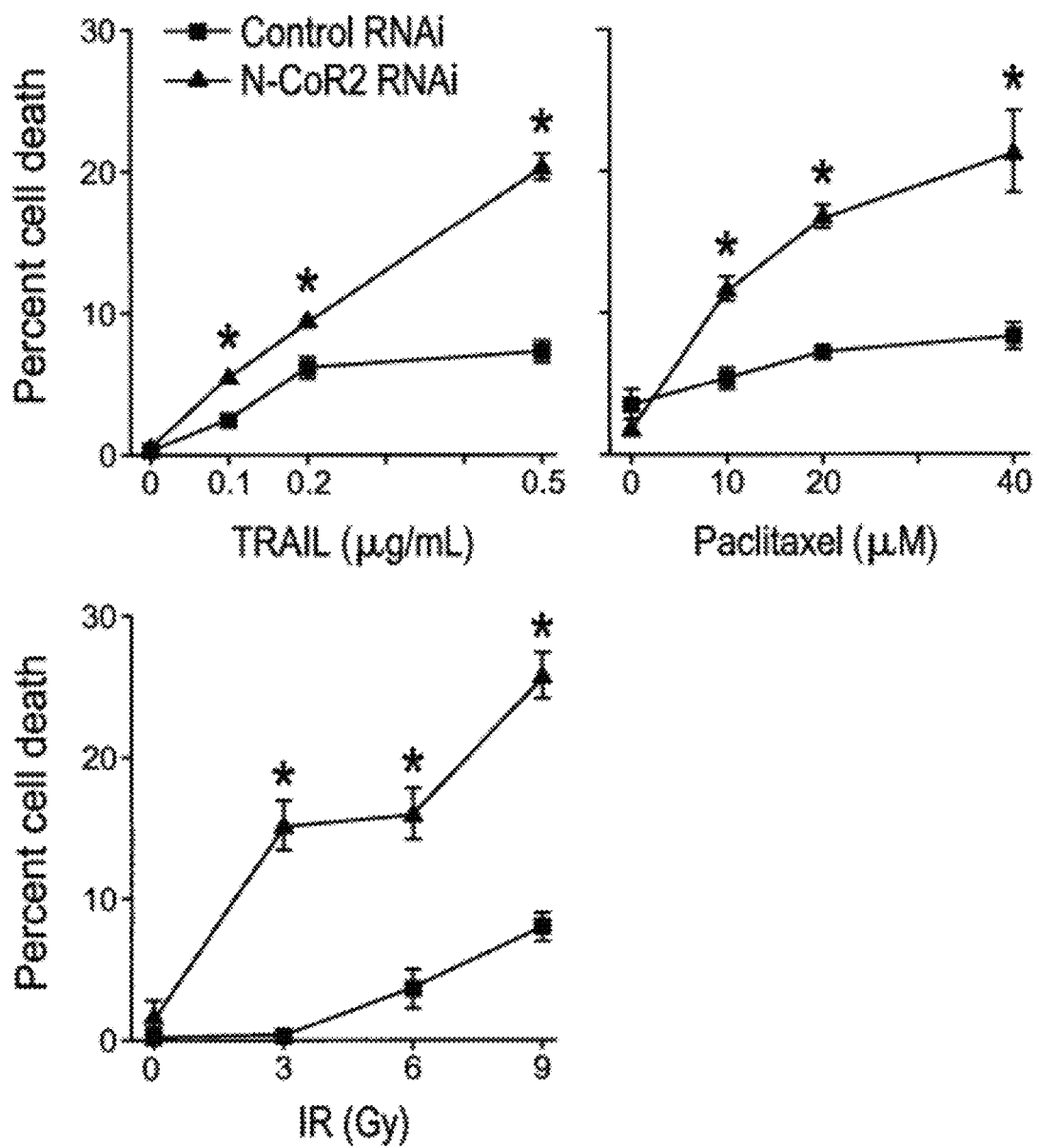
FIG. 13 Death sensitivity of HMT3522 S1 cells with stable downregulation of N-CoR2 expression and their control cells cultured as 3D acini to TRAIL, Paclitaxel and IR treatments.

FIG. 12 shows that stable downregulation of N-CoR2 expression by RNAi in HMT3522 S1 cells does not significantly alter their growth on culture plastics or the integrity and polarization of acini in 3D rBM, compared with cells stably transfected with control shRNA. However, as shown in FIG. 13, downregulation of N-CoR2 rendered the HMT3522 S1 cell acini much more sensitive to multiple death stimuli, including the death receptor ligand TRAIL, the cytotoxic drug Paclitaxel, and IR, than the acini formed by control cells across a wide range of drug concentrations or IR doses.

Figure 14:
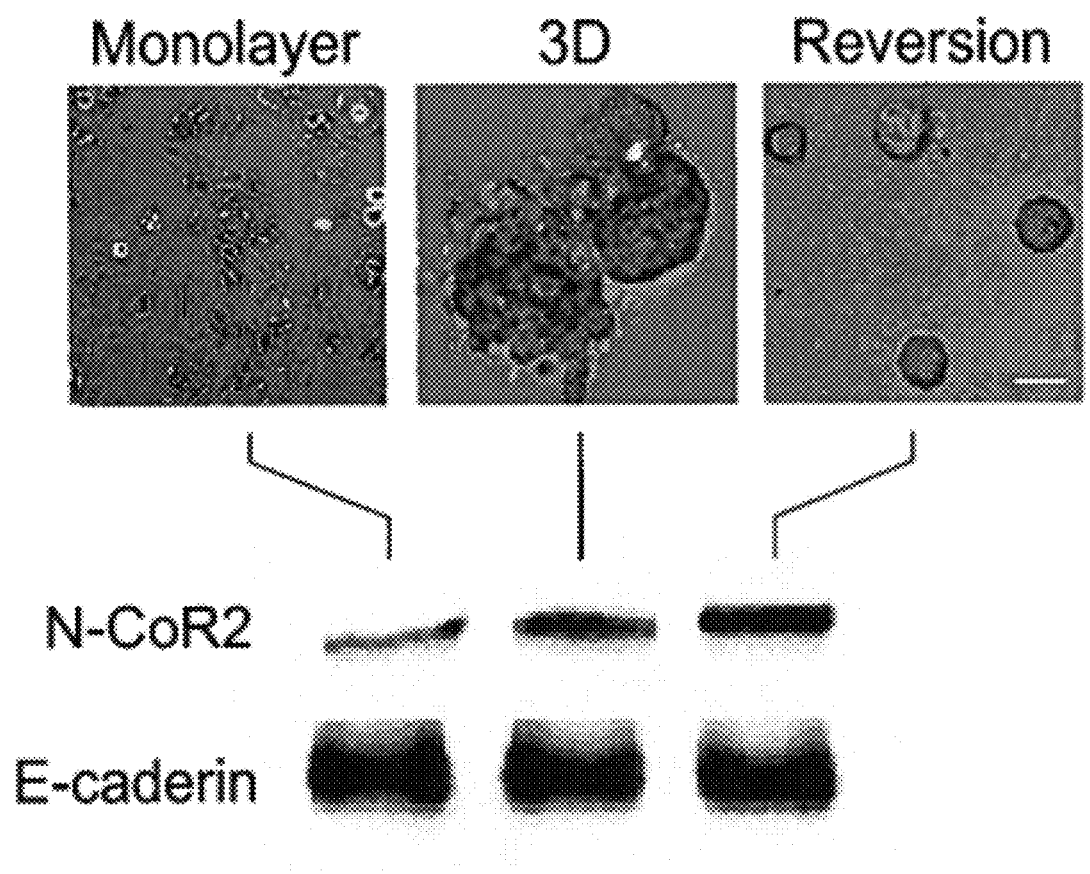
FIG. 14 Phase-contrast images and N-CoR2 protein expression of HMT3522 T4-2 cells cultured as 2D monolayers, 3D disorganized and reverted (rev) acinus-like architectures. Bar, 100 µm.

In FIG. 14, the neoplastic HMT3522 T4-2 cells grew as disorganized cellular aggregates in 3D rBM. Inhibiting EGFR activity by inclusion of an EGFR inhibitor tyrphostin AG 1478 resulted in the phenotypic reversion of the cellular aggregates into organized spheroid-like structures, which was consistent with previous results (Proc. Natl. Acad. Sci. USA 95:14821-14826 (1998); Cancer Cell 2:205-216 (2002)). Compared with HMT3522 T4-2 cells that were grown as cell monolayer on culture plastics, the protein abundance of N-CoR2 increased slightly when the same cells were grown as disorganized cellular aggregates in 3D rBM. Structural reversion of HMT3522 T4-2 cellular aggregates into organized spheroids by EGFR inhibition was accompanied with a further increase in the protein abundance of N-CoR2.

Figure 15:
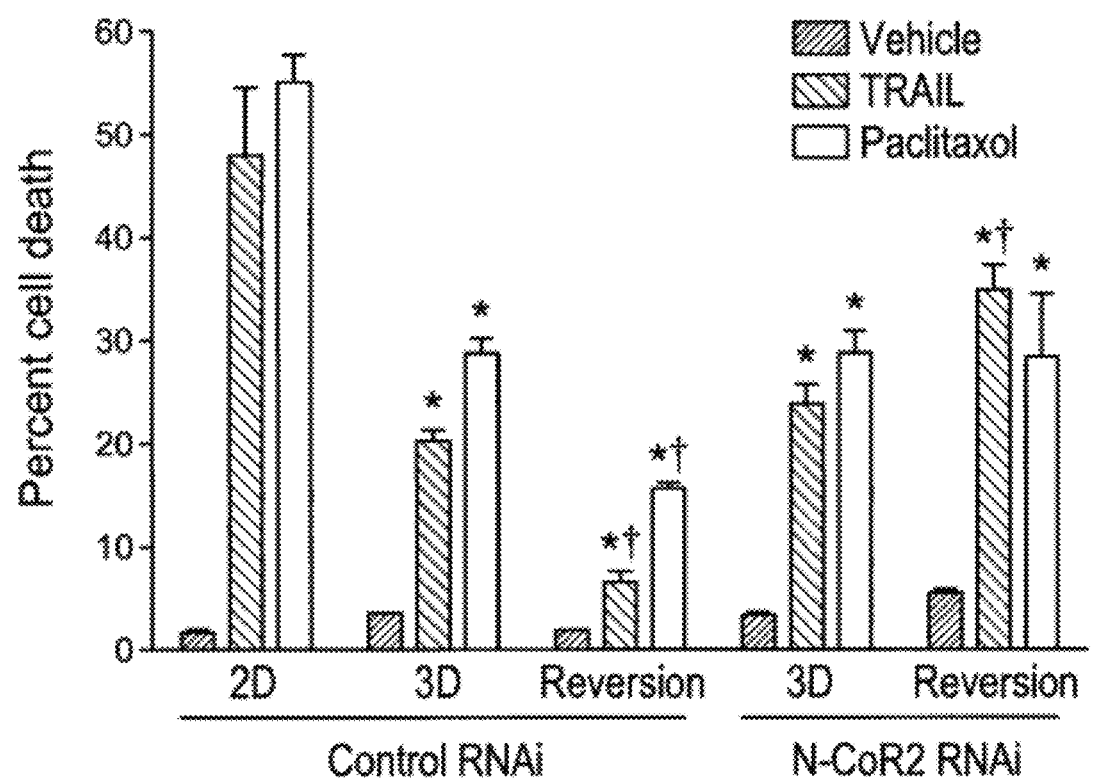
FIG. 15 Death sensitivities of HMT3522 T4-2 cells with stable downregulation of N-CoR2 and their control cells to TRAIL (1.0 µg/mL) or Paclitaxel (20 µM) in different culture models as detailed in FIG. 14. P<0.05, compared with control RNAi in 2D* or 3D†.

As shown in FIG. 15, HMT3522 T4-2 cells cultured in 3D rBM displayed decreased sensitivity (i.e., increased resistance) to different death stimuli, including TRAIL and Paclitaxel treatments. Structurally reverted HMT3522 T4-2 spheroids displayed a further decrease in the sensitivity to TRAIL and Paclitaxel treatments. The increased resistance of the spheroidal structures to death stimuli was completely reversed by downregulation of N-CoR2 expression, suggesting that N-CoR2 also mediates architecture-dependent death resistance in neoplastic breast epithelial cells.

Figure 16:
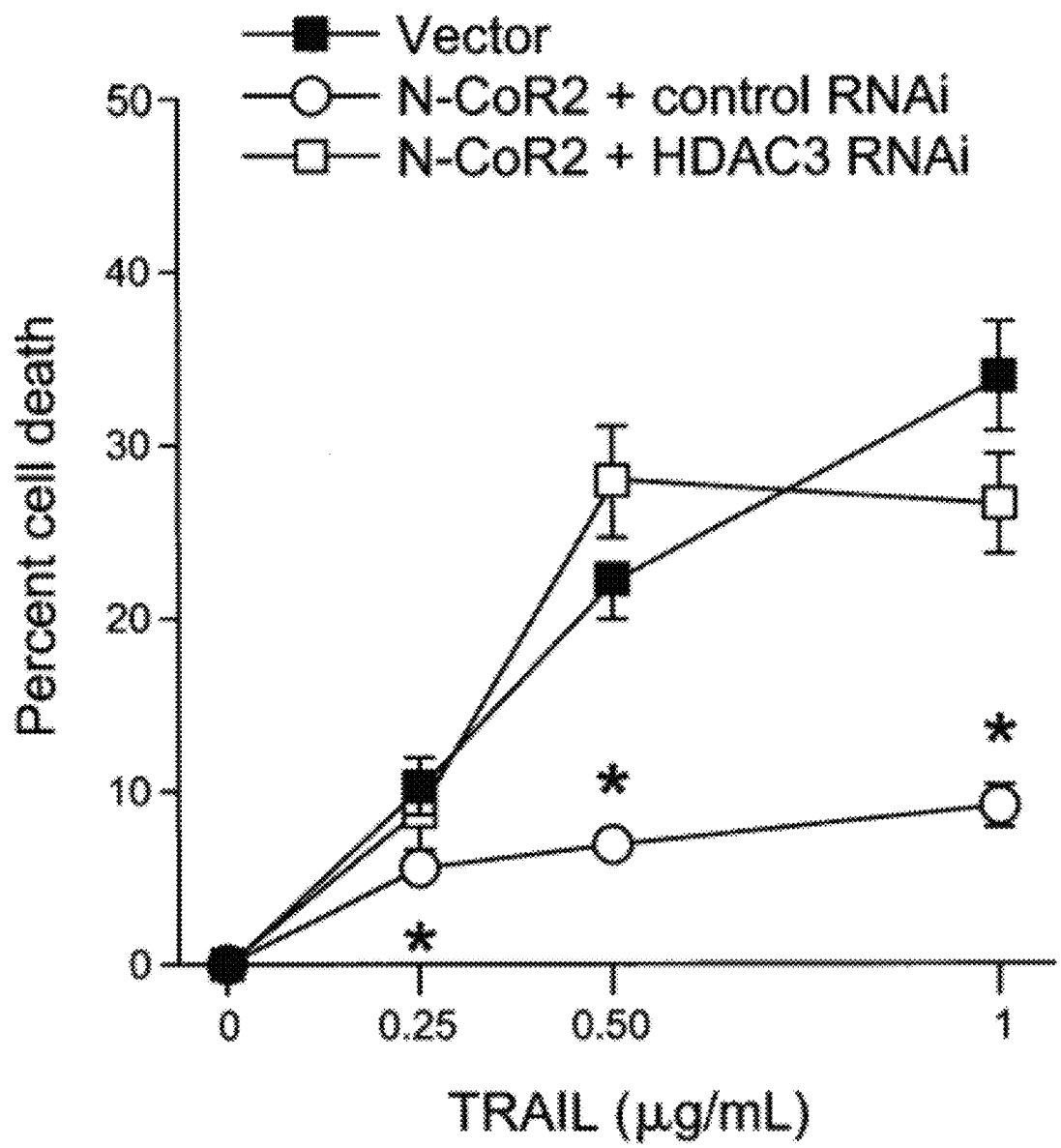
FIG. 16 Death sensitivities of HMT3522 T4-2 cells with stable overexpression of N-CoR2, the vector control cells and those with stable downregulation of HDAC3 to TRAIL treatments. *P<0.05, compared with vector control cells.

FIG. 16 shows that stable overexpression of N-CoR2 in HMT3522 T4-2 cells by retrovirus-mediated gene transduction render them markedly resistant to TRAIL treatments. However, when HDAC3 expression was simultaneously downregulated by retrovirus-mediated RNAi in the N-CoR2-overexpressed cells, their sensitivity to the TRAIL treatment could be restored to an extent comparable to that of vehicle-treated cells, suggesting that the ability of N-CoR2 to suppress cell death is HDAC3-dependent and the death resistance can be reversed by HDAC3 downregulation.

The results of this example show that multidrug resistant breast cancer cells can be sensitized by the downregulation of N-CoR2 and/or HDAC3 gene expression. In this fashion, multidrug resistant tumors should also be sensitized in vivo by these and equivalent methods.

Example 6

This example demonstrates that cancer cells can be sensitized to death stimuli and anticancer therapy by abrogating the N-CoR2-dependent activation of HDAC3.

The nuclear deacetylase activity of HDAC3 requires its stoichiometric interaction with N-CoR2. It has been shown previously that mutation of the lysine 449 residue on N-CoR2 to alanine does not influence the interaction between N-CoR2 and HDAC3 but abolishes the activation of HDAC3 (Proc. Natl. Acad. Sci. USA 102:6009-6014 (2005)). Based on this finding, to abrogate the N-CoR2-dependent activation of HDAC3, the lysine 449 residue on N-CoR2 was mutated to alanine using the QuickChange Site-Directed Mutagenesis kit (Stratagene) using pMFG-tet-HA-EGFP-NCOR2 as a template. The retroviral construct carrying N-CoR2 (K449A) then was stably incorporated into the genomic DNA of HMT3522 T4-2 cells by retrovirus-mediated gene transduction as described in Example 1. The resultant HMT3522 T4-2 N-CoR2 (K449A) cells were maintained and propagated on collagen I-coated culture dishes as described in Example 1.

To confirm the ability of the mutant N-CoR2 (K449A) to abrogate the deacetylase activity of HDAC3, HEK 293 cells were transduced with retroviral constructs inducibly expressing myc-tagged N-CoR2, N-CoR2 (K449A), or a control EGFP construct (pLZRS-MFG-tet-myc(4)-EGFP-N-CoR2, pLZRS-MFG-tet-myc(4)-EGFP-N-CoR2 (K449A), or pLZRS-MFG-tet-myc(4)-EGFP). Cells were treated with 1 µg/mL of doxycycline for 16 hours to induce expressions of myc tagged proteins and nuclear protein extracts were prepared as described previously (Nucleic Acid Res. 11:1475-1489 (1983)). Nuclear lysates was transferred and incubated at 4° C. for 3 hours with 50 µL of equilibrated protein G agarose beads (Invitrogen) and 5 μg of purified hybridoma mouse anti-myc antibody. Beads were washed with wash buffer (diluent buffer with 0.5 M KCl) three times and with diluent once. Washed conjugated beads were used in the Fluor de Lys™ Assay System (BioMol) per kit instructions to determine HDAC activity associated with the immunoprecipitation. Fluorescence was determined using a Spectra Max M5 fluorimetric plate reader (Molecular Devices). The HDAC activity assay was performed with or without 5 μM of the HDAC inhibitor trichostatin A (TSA) (as a negative control). Results were repeated in quadruplicate. P<0.05, compared with vector* or N-CoR2†.

To examine the interaction between the wild-type or mutant N-CoR2 and HDAC3, nuclear lysates from HEK 293 cells stably expressing myc-tagged N-CoR2, N-CoR2 (K449A), or empty vector were immunoprecipitated with the anti-myc antibody as described above. The precipitates were then analyzed by Western blot using anti-myc or anti-HDAC3 antibody (Santa Cruz). Lamin B1 was used as nuclear loading control.

HMT3522 T4-2 cells stably overexpressing the mutant N-CoR2 (K449A) were embedded within rBM gel and cultured for 5 days, after which the 3D culture was treated with recombinant, purified human TRAIL peptides (BIOMOL). Percent cell death induced by TRAIL was quantified using detection of active caspase 3 as described in Example 4.

Figure 17:
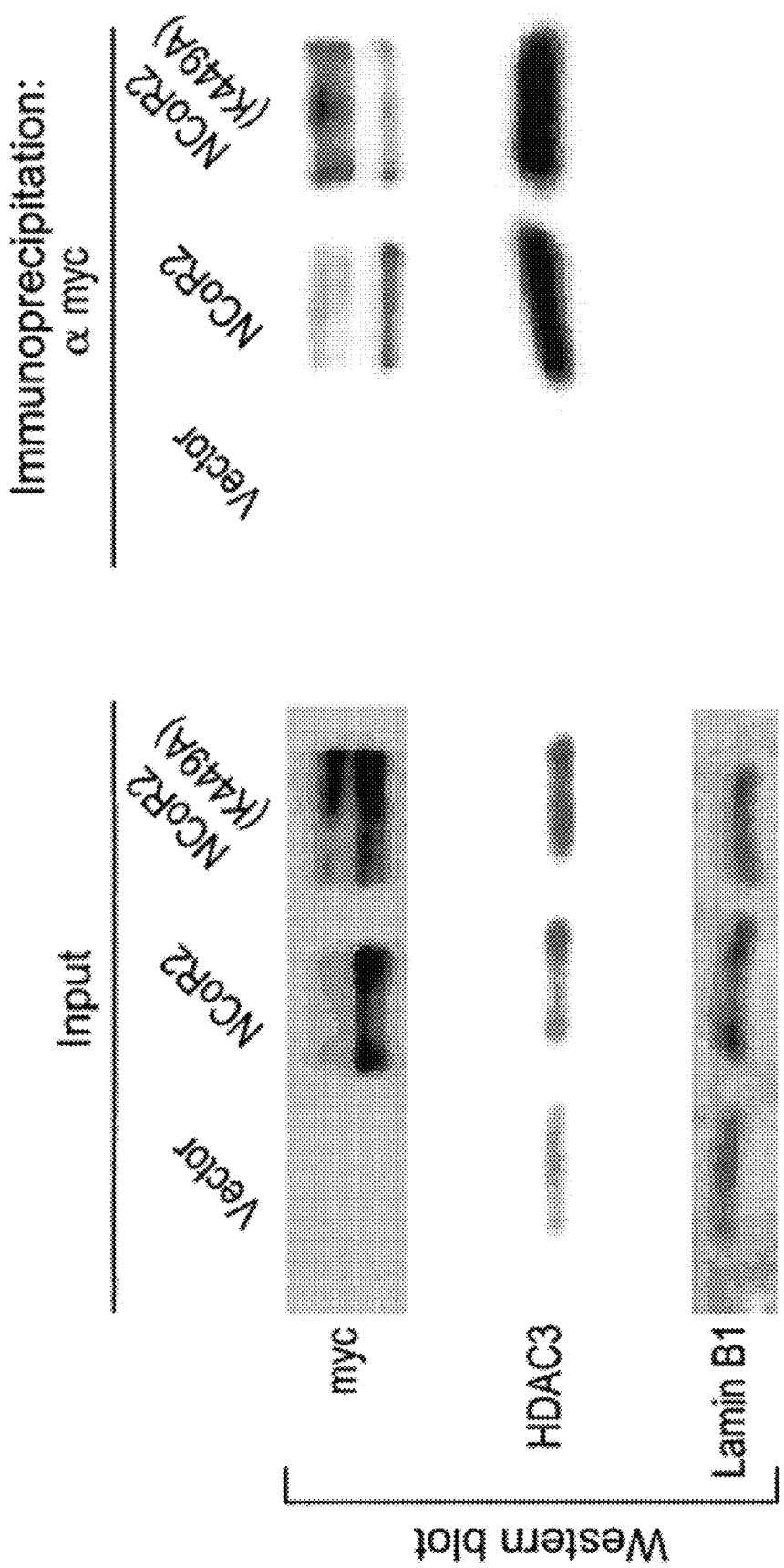
FIG. 17 Nuclear lysates from HEK 293 cells stably expressing myc-tagged N-CoR2, N-CoR2 (K449A) or empty vector were immunoprecipitated with the anti-myc antibody. The precipitates were analyzed by Western blot using anti-myc or anti-HDAC3 antibody. Lamin B1 was used as nuclear loading control.

FIG. 17 shows that the mutant N-CoR2 (K449A) protein, when transfected into cells, retained the ability to bind to HDACs3 in the cell nuclear extracts similar to the wild type N-CoR2 protein.

Figure 18:
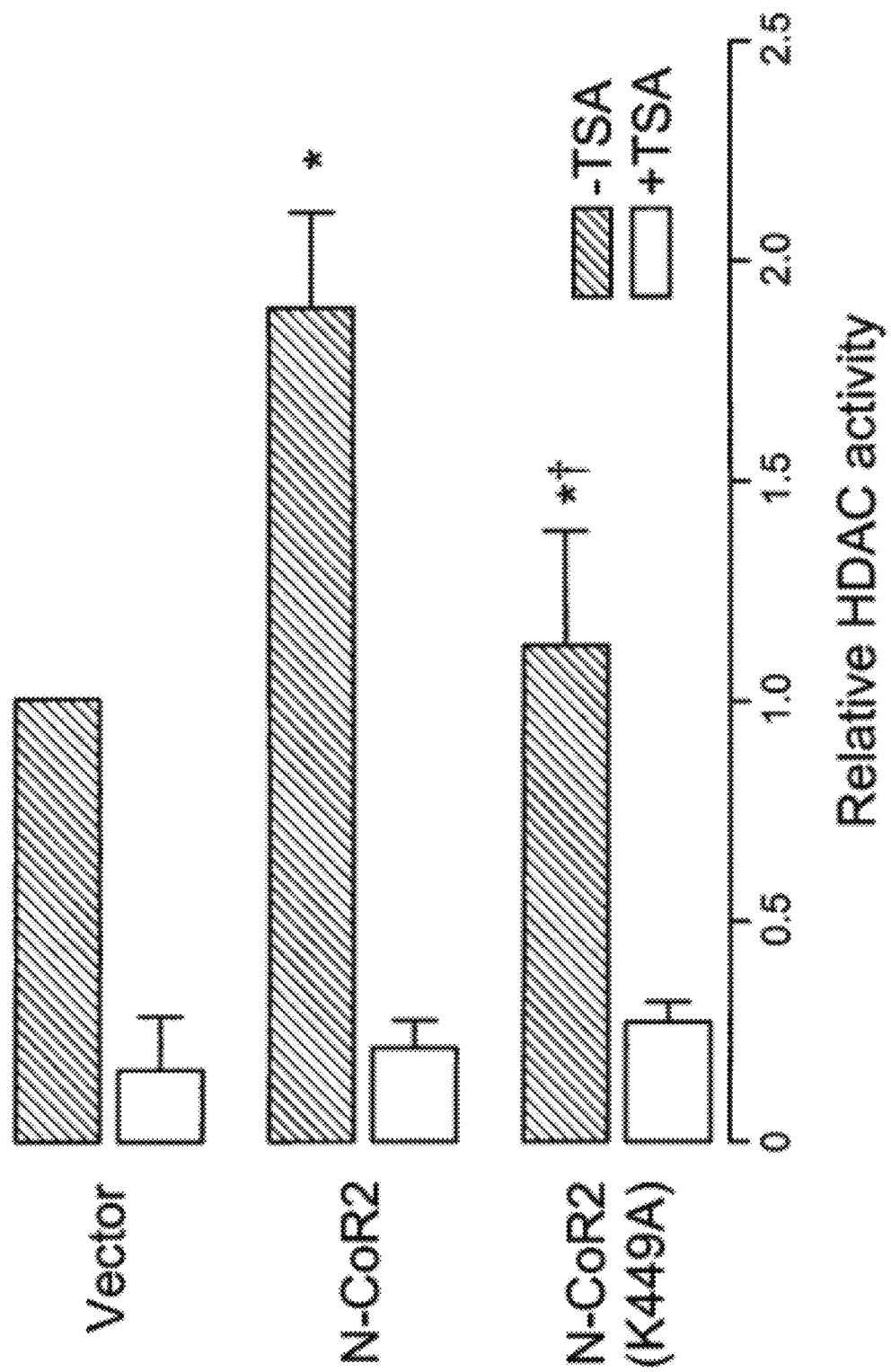
FIG. 18 Myc-immunoprecipitated N-CoR2, N-CoR2 (K449A) or empty vector complexes from nuclear extracts of HEK 293 cells were analyzed for HDAC activity using a fluorimetric activity assay with or without 5 µM of the HDAC inhibitor TSA. Results were repeated in quadruplicate. P<0.05, compared with vector* or N-CoR2†.

As shown in FIG. 18, the overexpression of wild type N-CoR2 protein in cells significantly enhanced the deacetylase activity of the immunoprecipitated HDAC3 from the nuclear extracts. Conversely, the overexpressed mutant N-CoR2 (K449A) protein failed to do so, as such, the deacetylase activity of HDAC3 remained unaltered compared with the wild-type protein.

Figure 19:
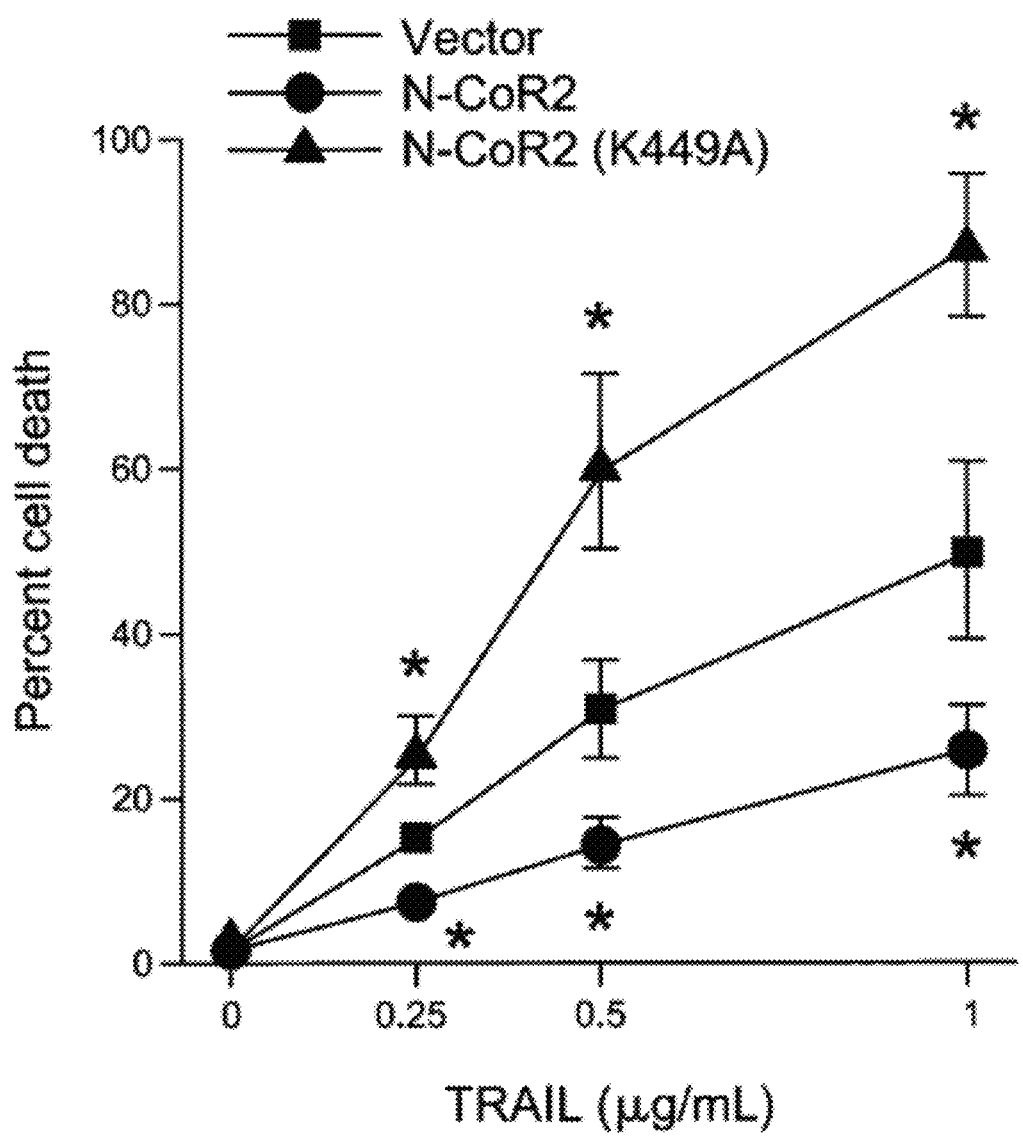
FIG. 19 Death sensitivities of HMT3522 T4-2 cells with stable overexpression of wild-type N-CoR2, N-CoR2 (K449A) or the control vector to TRAIL treatments. Data are mean±SEM of triplicate experiments; *P<0.05, compared with vector.

As shown in FIG. 19, stable overexpression of wild-type N-CoR2 in HMT3522 T4-2 cells rendered them less sensitive to death induction by TRAIL treatments. However, when the mutant N-CoR2 (K449A) was transduced into HMT3522 T4-2 cells, they were rendered hypersensitive to death induction to an extent even greater than that of the vector control cells. This result shows that the deacetylase activity of HDAC3 is crucial to the N-CoR2-mediated death resistance in breast epithelial cells. Thus, targeting the interaction between N-CoR2 and HDAC3 is a valid approach to sensitize neoplastic cells to death stimuli and anticancer treatments.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of diagnosing a treatment resistant tumor in a subject, the method comprising the steps of:
    (a) analyzing a tumor sample from the subject with an assay that specifically detects N-CoR2 and MK167;
    (b) determining whether or not N-CoR2 and MK167 are differentially expressed (over or under expressed); and
    (c) determining if the differential expression correlates with a multi drug resistance signature, thereby providing a diagnosis for a treatment resistant tumor.

2. The method of claim 1, wherein the assay detects nucleic acid.

3. The method of claim 2, wherein the assay comprises a technique selected from the group consisting of mass spectroscopy, PCR, RT-PCR, microarray hybridization, thermal cycle sequencing, capillary array sequencing, and solid phase sequencing.

4. The method of claim 1, wherein the assay comprises a reagent that binds to a nucleic acid.

5. The method of claim 4, wherein the reagent is a nucleic acid.

6. The method of claim 1, wherein the method comprises microarray hybridization.

7. A method of providing a prognosis for a malignant tumor after treatments, the method comprising the steps of:
   (a) analyzing a tumor sample from a subject with an assay that specifically detects N-CoR2 and MK167;
   (b) determining whether or not N-CoR2 and MK167 are differentially expressed (over or under expressed); and
   (c) determining if the differential expression correlates with a multi drug resistance signature, thereby providing a prognosis for a malignant tumor.

8. The method of claim 7, wherein the assay comprises microarray hybridization, RT-PCR, protein microarray or any assay described in claim 3.

9. A method of providing a prognosis for the response of a malignant tumor to preoperative anti-tumor therapeutics, the method comprising the steps of:
   (a) analyzing a tumor sample from the subject with an assay that specifically detects N-CoR2 and MK167;
   (b) determining whether or not N-CoR2 and MK167 are differentially expressed (over or under expressed); and
   (c) determining if the differential expression correlates with a multidrug resistance signature, thereby providing a prognosis for the response of a tumor to preoperative anti-tumor therapeutics.

10. The method of claim 9, wherein said anti-tumor therapeutics comprises chemotherapy, immunotherapy and/or radiation therapy.

11. The method of claim 9, wherein the assay comprises microarray hybridization, RT-PCR, protein microarray or any assay described in claim 3.

12. The method of claim 11, wherein the tumor is a breast tumor.

13. A method of providing a prognosis for the response of a malignant breast tumor to preoperative anti-tumor therapeutics, the method comprising the steps of:
   (a) analyzing a tumor sample from the subject with an assay that specifically detects N-CoR2 and MK167;
   (b) determining whether or not N-CoR2 and MK167 are differentially expressed (over or under expressed); and
   (c) determining if the differential expression correlates with a multidrug resistance signature, thereby providing a prognosis for the response of a tumor to preoperative anti-tumor therapeutics.

14. A method of diagnosing a treatment resistant tumor in a subject, the method comprising the steps of:
   (a) analyzing a tumor sample from the subject with an assay that specifically detects MK167;
   (b) determining whether or not MK167 is differentially expressed (over or under expressed); and
   (c) determining if the differential expression correlates with a multi drug resistance signature, thereby providing a diagnosis for a treatment resistant tumor.

15. The method of claim 14, wherein the assay detects nucleic acid.

16. The method of claim 15, wherein the assay comprises a technique selected from the group consisting of mass spectroscopy, PCR, RT-PCR, microarray hybridization, thermal cycle sequencing, capillary array sequencing, and solid phase sequencing.

17. The method of claim 14, wherein the assay comprises a reagent that binds to a nucleic acid.

18. The method of claim 17, wherein the reagent is a nucleic acid.

19. The method of claim 14, wherein the method comprises microarray hybridization.

20. A method of providing a prognosis for a malignant tumor after treatments, the method comprising the steps of:
   (a) analyzing a tumor sample from a subject with an assay that specifically detects MK167;
   (b) determining whether or not MK167 is differentially expressed (over or under expressed); and
   (c) determining if the differential expression correlates with a multi drug resistance signature, thereby providing a prognosis for a malignant tumor.

21. The method of claim 20, wherein the assay comprises microarray hybridization, RT-PCR, protein microarray or any assay described in claim 16.

22. A method of providing a prognosis for the response of a malignant tumor to preoperative anti-tumor therapeutics, the method comprising the steps of:
   (a) analyzing a tumor sample from the subject with an assay that specifically detects MK167;
   (b) determining whether or not MK167 is differentially expressed (over or under expressed); and
   (c) determining if the differential expression correlates with a multidrug resistance signature, thereby providing a prognosis for the response of a tumor to preoperative anti-tumor therapeutics.

23. The method of claim 22, wherein said anti-tumor therapeutics comprises chemotherapy, immunotherapy and/or radiation therapy.

24. The method of claim 22, wherein the assay comprises microarray hybridization, RT-PCR, protein microarray or any assay described in claim 3.

25. The method of claim 24, wherein the tumor is a breast tumor.

\* \* \* \* \*

UNITED STATES PATENT AND TRADEMARK OFFICE
CERTIFICATE OF CORRECTION

| | | |
|---|---|---|
| PATENT NO. | : 8,257,928 B2 | Page 1 of 1 |
| APPLICATION NO. | : 13/227279 | |
| DATED | : September 4, 2012 | |
| INVENTOR(S) | : Valerie M. Weaver et al. | |

It is certified that error appears in the above-identified patent and that said Letters Patent is hereby corrected as shown below:

IN THE SPECIFICATION

In Col. 1, at lines 19-22, please amend the paragraph below as follows:

~~This invention was made in part with Governmental support under grant no. CA078731 awarded by the National Institute of Health. The Government has rights in this invention.~~

This invention was made with Government support under Grant No. CA078731 awarded by the National Institutes of Health. The Government has certain rights in the invention.

Signed and Sealed this
Twenty-ninth Day of October, 2013

Teresa Stanek Rea
*Deputy Director of the United States Patent and Trademark Office*

```
                         SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: siRNA oligonucleotide sequence for nuclear
      corepressor 2, nucear receptor co-repressor 2 (N-CoR2, NCOR2),
      silencing meditator for retinoid and thyroid hormone receptors
      (SMRT, SMRTE, SMRTE-tau), CTG26, TNRC14, TRAC1

<400> SEQUENCE: 1
aagggtatca tcaccgctgt                                              20

<210> SEQ ID NO 2
<211> LENGTH: 21
<212> TYPE: DNA
<213> ORGANISM: Artificial Sequence
<220> FEATURE:
<223> OTHER INFORMATION: siRNA oligonucleotide sequence for class I
      histone deacetylase 3 (HDAC3)

<400> SEQUENCE: 2
aagatgctga accatgcacc t                                            21
```